(12) United States Patent
Wesley et al.

(10) Patent No.: US 9,314,082 B2
(45) Date of Patent: Apr. 19, 2016

(54) SYSTEM AND METHOD FOR EXTRACTION OF HAIR FOLLICLE

(71) Applicant: PiloFocus, Inc., New York, NY (US)

(72) Inventors: Carlos K. Wesley, New York, NY (US); Trevor K. Lewis, Lehi, UT (US)

(73) Assignee: PiloFocus, Inc., New York, NY (US)

( * ) Notice: Subject to any disclaimer, the term of this patent is extended or adjusted under 35 U.S.C. 154(b) by 0 days.

(21) Appl. No.: 14/272,990

(22) Filed: May 8, 2014

(65) Prior Publication Data

US 2014/0236181 A1 Aug. 21, 2014

Related U.S. Application Data

(63) Continuation-in-part of application No. 13/654,252, filed on Oct. 17, 2012, now Pat. No. 8,998,931, and a continuation-in-part of application No. 13/496,905, filed on Apr. 30, 2012.

(Continued)

(51) Int. Cl.
*A61B 17/50* (2006.01)
*A45D 26/00* (2006.01)
(Continued)

(52) U.S. Cl.
CPC ...... *A45D 26/0057* (2013.01); *A61B 17/32002* (2013.01); *A61B 17/320016* (2013.01);
(Continued)

(58) Field of Classification Search
CPC .............................................. A61B 2017/00752
USPC .......... 606/133, 116, 117, 191, 131, 323, 327
See application file for complete search history.

(56) References Cited

U.S. PATENT DOCUMENTS

| 4,476,864 A | 10/1984 | Tezel |
| 4,763,669 A | 8/1988 | Jaeger |

(Continued)

FOREIGN PATENT DOCUMENTS

| EP | 1642541 A1 | 4/2006 |
| GB | 2021467 A | 12/1979 |

(Continued)

OTHER PUBLICATIONS

Invitation to Pay Additional Fees and, Where Applicable, Protest Fee for corresponding International Application No. PCT/US2014/037358, dated Sep. 4, 2014 (6 pages).

(Continued)

*Primary Examiner* — Jonathan W Miles
*Assistant Examiner* — Chima Igboko
(74) *Attorney, Agent, or Firm* — Craig Buschmann; Ryan L. Marshall; Brinks Gilson & Lione

(57) ABSTRACT

Systems and methods for extracting hair follicle from underneath an external surface of the skin are provided. The systems may include a first member and a counter pressure device. The first member may define a first bore and may have a longitudinal axis. A portion of the first member may be configured to be moved below an external surface of a skin. The first member may be configured to translate at least in a first direction along the longitudinal axis through a tissue and rotate about the longitudinal axis. The counter pressure device may be configured to interface with at least the external surface of the skin such that the tissue is disposed between the first member and the counter pressure device. The translation and rotation of the first member may result in cutting at least a portion of the tissue.

14 Claims, 45 Drawing Sheets

Related U.S. Application Data

(60) Provisional application No. 61/821,098, filed on May 8, 2013, provisional application No. 61/673,143, filed on Jul. 18, 2012, provisional application No. 61/243,271, filed on Sep. 17, 2009.

(51) Int. Cl.
| | |
|---|---|
| *A61B 17/32* | (2006.01) |
| *A61B 17/3205* | (2006.01) |
| *A61B 19/00* | (2006.01) |
| *A61F 2/10* | (2006.01) |
| *A61B 17/3209* | (2006.01) |
| *A61B 17/00* | (2006.01) |

(52) U.S. Cl.
CPC ........... *A61B17/32053* (2013.01); *A61B 19/26* (2013.01); *A61B 17/32093* (2013.01); *A61B 2017/00752* (2013.01); *A61B 2017/32004* (2013.01); *A61B 2019/5276* (2013.01); *A61B 2217/005* (2013.01); *A61F 2/10* (2013.01)

(56) References Cited

U.S. PATENT DOCUMENTS

| | | | |
|---|---|---|---|
| 5,133,360 A | 7/1992 | Spears | |
| 5,133,722 A | 7/1992 | Avrahami et al. | |
| 5,135,531 A | 8/1992 | Shiber | |
| 5,368,014 A | 11/1994 | Anapliotis et al. | |
| 5,391,166 A | 2/1995 | Eggers | |
| 5,439,475 A | 8/1995 | Bennett | |
| 5,445,615 A * | 8/1995 | Yoon | A61B 17/3423 128/DIG. 26 |
| 5,472,439 A | 12/1995 | Hurd | |
| 5,478,351 A | 12/1995 | Meade et al. | |
| 5,535,759 A | 7/1996 | Wilk | |
| 5,601,601 A | 2/1997 | Tal et al. | |
| 5,618,303 A | 4/1997 | Marlow et al. | |
| 5,630,782 A | 5/1997 | Adair | |
| 5,665,100 A | 9/1997 | Yoon | |
| 5,676,678 A | 10/1997 | Schad | |
| 5,676,680 A | 10/1997 | Lim | |
| 5,782,851 A | 7/1998 | Rassman | |
| 5,782,853 A | 7/1998 | Zeevi | |
| 5,788,651 A * | 8/1998 | Weilandt | A61B 10/0266 600/567 |
| 5,792,163 A | 8/1998 | Hitzig | |
| 5,817,120 A | 10/1998 | Rassman | |
| 5,823,971 A | 10/1998 | Robinson et al. | |
| 5,827,297 A | 10/1998 | Boudjema | |
| 5,895,403 A | 4/1999 | Collinsworth | |
| 5,922,000 A | 7/1999 | Chodorow | |
| 5,984,936 A | 11/1999 | Mangubat | |
| 6,027,512 A | 2/2000 | Bridges | |
| 6,059,719 A | 5/2000 | Yamamoto et al. | |
| 6,352,503 B1 | 3/2002 | Matsui et al. | |
| 6,419,627 B1 | 7/2002 | Ben Nun | |
| 6,500,170 B2 * | 12/2002 | Palmer | A61B 17/3417 604/164.04 |
| 6,544,259 B1 | 4/2003 | Tsaliovich | |
| 6,572,625 B1 | 6/2003 | Rassman | |
| 6,585,746 B2 | 7/2003 | Gildenberg | |
| 6,620,158 B2 | 9/2003 | Ronci | |
| 7,130,717 B2 | 10/2006 | Gildenberg | |
| 7,156,856 B2 | 1/2007 | Feller | |
| 7,261,721 B2 | 8/2007 | Feller | |
| 7,329,252 B1 | 2/2008 | Yamazaki et al. | |
| 7,517,321 B2 | 4/2009 | McCullough et al. | |
| 7,621,933 B2 | 11/2009 | Bodduluri | |
| 7,621,934 B2 | 11/2009 | Bodduluri | |
| 7,627,157 B2 | 12/2009 | Qureshi | |
| 7,727,164 B2 | 6/2010 | Cicenas et al. | |
| 7,806,121 B2 | 10/2010 | Bodduluri | |
| RE42,381 E | 5/2011 | Gildenberg | |
| RE42,437 E | 6/2011 | Gildenberg | |
| RE42,438 E | 6/2011 | Gildenberg | |
| 7,962,192 B2 | 6/2011 | Bodduluri | |
| 8,048,090 B2 | 11/2011 | Qureshi | |
| 8,066,717 B2 | 11/2011 | DuBois | |
| 8,104,480 B2 | 1/2012 | Bodduluri | |
| 8,128,639 B2 | 3/2012 | Tippett | |
| 8,133,237 B2 | 3/2012 | Oostman, Jr. | |
| 8,133,247 B2 | 3/2012 | Bodduluri et al. | |
| 8,317,804 B1 | 11/2012 | Rassman et al. | |
| 8,454,627 B2 | 6/2013 | Bodduluri et al. | |
| 8,690,894 B2 | 4/2014 | Bodduluri et al. | |
| 2002/0042623 A1 * | 4/2002 | Blatter | A61B 17/0643 606/167 |
| 2002/0103500 A1 | 8/2002 | Gildenberg | |
| 2003/0040706 A1 * | 2/2003 | Kuracina | A61B 5/1405 604/116 |
| 2003/0097143 A1 | 5/2003 | Mittelstaedt | |
| 2003/0097144 A1 | 5/2003 | Lee | |
| 2003/0120298 A1 | 6/2003 | Gildenberg | |
| 2003/0212415 A1 | 11/2003 | Karasiuk | |
| 2003/0233114 A1 | 12/2003 | Merboth | |
| 2004/0049206 A1 | 3/2004 | Rassman | |
| 2004/0092924 A1 | 5/2004 | Vasa | |
| 2004/0097973 A1 | 5/2004 | Loshakove et al. | |
| 2005/0049622 A1 | 3/2005 | Mittelstaeot | |
| 2005/0177142 A1 | 8/2005 | Jay | |
| 2005/0216035 A1 | 9/2005 | Kraus et al. | |
| 2005/0267506 A1 | 12/2005 | Harris | |
| 2006/0142741 A1 | 6/2006 | Jay | |
| 2006/0161179 A1 * | 7/2006 | Kachenmeister | A61B 17/32053 606/133 |
| 2006/0178677 A1 | 8/2006 | Brinson | |
| 2006/0200040 A1 | 9/2006 | Weikel et al. | |
| 2006/0259102 A1 | 11/2006 | Slatkine | |
| 2007/0078466 A1 | 4/2007 | Bodduluri | |
| 2007/0078473 A1 * | 4/2007 | Bodduluri | A61B 17/32053 606/167 |
| 2007/0106307 A1 | 5/2007 | Bodduluri | |
| 2007/0122387 A1 | 5/2007 | Cochran | |
| 2007/0128172 A1 | 6/2007 | Yoshizato | |
| 2007/0156164 A1 | 7/2007 | Cole | |
| 2007/0213741 A1 | 9/2007 | Cole | |
| 2007/0255293 A1 | 11/2007 | Corre | |
| 2007/0293884 A9 | 12/2007 | Cole | |
| 2007/0299387 A1 * | 12/2007 | Williams | A61B 1/00052 604/22 |
| 2008/0033410 A1 * | 2/2008 | Rastegar | A61B 18/20 606/9 |
| 2008/0033455 A1 | 2/2008 | Rassman | |
| 2008/0051805 A1 * | 2/2008 | Pinchuk | A61B 17/3468 606/133 |
| 2008/0051806 A1 | 2/2008 | Cole | |
| 2008/0091225 A1 | 4/2008 | Cole et al. | |
| 2008/0097458 A1 * | 4/2008 | Donahoe | A61B 17/862 606/104 |
| 2008/0177287 A1 | 7/2008 | Rassman | |
| 2008/0186496 A1 | 8/2008 | Leveque | |
| 2008/0200861 A1 * | 8/2008 | Shalev | A61Q 9/04 604/20 |
| 2008/0215039 A1 * | 9/2008 | Slatkine | A61B 17/205 606/9 |
| 2008/0234602 A1 * | 9/2008 | Oostman | A61B 10/0266 600/564 |
| 2008/0234697 A1 | 9/2008 | DuBois | |
| 2008/0234698 A1 * | 9/2008 | Oostman | A61B 10/0266 606/133 |
| 2009/0005765 A1 * | 1/2009 | Oostman, Jr. | A61B 17/32053 606/9 |
| 2009/0012536 A1 | 1/2009 | Rassman et al. | |
| 2009/0052738 A1 | 2/2009 | Qureshi | |
| 2009/0088776 A1 | 4/2009 | Harris | |
| 2009/0240261 A1 | 9/2009 | Drews | |
| 2009/0306498 A1 | 12/2009 | Bodduluri | |
| 2009/0306680 A1 | 12/2009 | Qureshi | |
| 2010/0080415 A1 | 4/2010 | Qureshi | |
| 2010/0080417 A1 | 4/2010 | Qureshi | |
| 2010/0082042 A1 | 4/2010 | Drews | |
| 2010/0125287 A1 | 5/2010 | Cole | |
| 2010/0166719 A1 | 7/2010 | Yoshizato | |

(56) References Cited

U.S. PATENT DOCUMENTS

| | | |
|---|---|---|
| 2010/0217236 A1 | 8/2010 | Gill |
| 2010/0262129 A1 | 10/2010 | Roy |
| 2011/0046639 A1 | 2/2011 | Giotis |
| 2011/0060321 A1 | 3/2011 | Chandler |
| 2011/0160746 A1 | 6/2011 | Umar |
| 2011/0178533 A1 | 7/2011 | Oostman |
| 2011/0224693 A1 | 9/2011 | Bodduluri |
| 2011/0245845 A1* | 10/2011 | Oostman, Jr. .... A61B 17/32053 606/133 |
| 2011/0319921 A1 | 12/2011 | Giotis |
| 2012/0010631 A1 | 1/2012 | DuBois |
| 2012/0039516 A1 | 2/2012 | Qureshi |
| 2012/0041430 A1 | 2/2012 | Anderson |
| 2012/0041451 A1 | 2/2012 | Bodduluri |
| 2012/0215231 A1 | 8/2012 | Wesley |
| 2013/0190776 A1 | 7/2013 | Zhang et al. |
| 2013/0226213 A1 | 8/2013 | Kim et al. |
| 2013/0304090 A1 | 11/2013 | Oostman et al. |
| 2013/0340260 A1* | 12/2013 | Sueyoshi .......... A45D 26/0057 30/123 |

FOREIGN PATENT DOCUMENTS

| | | |
|---|---|---|
| JP | 59-114511 | 7/1984 |
| JP | 64-080335 | 3/1989 |
| JP | 03-086315 | 4/1991 |
| JP | 09-215656 | 8/1997 |
| JP | 2000-014631 A | 1/2000 |
| JP | 2000-037348 A | 2/2000 |
| JP | 2001-511393 A | 8/2001 |
| JP | 2008-502437 A | 1/2008 |
| JP | 2011-516169 A | 5/2011 |
| KR | 2007-0037577 A | 4/2007 |
| WO | WO 99/05997 A1 | 2/1999 |
| WO | WO 01/35125 A1 | 5/2001 |
| WO | WO 2005/109799 A2 | 11/2005 |
| WO | WO 2007/041267 A2 | 4/2007 |
| WO | WO 2007/087463 A2 | 8/2007 |
| WO | WO 2008/024954 A2 | 2/2008 |
| WO | WO 2008/027829 A2 | 3/2008 |
| WO | WO 2009/083741 A1 | 7/2009 |
| WO | WO 2009/123635 A1 | 10/2009 |
| WO | WO 2009/146068 A1 | 12/2009 |
| WO | WO 2010/039413 A1 | 4/2010 |
| WO | WO 2010/041089 A1 | 4/2010 |
| WO | WO 2010/057018 A2 | 5/2010 |
| WO | WO 2010/131270 A1 | 11/2010 |
| WO | WO 2011/035125 A1 | 3/2011 |
| WO | WO 2011/082130 A2 | 7/2011 |
| WO | WO 2011/123218 A1 | 10/2011 |
| WO | WO 2013/059349 A1 | 4/2013 |
| WO | WO 2014/182941 A1 | 11/2014 |

OTHER PUBLICATIONS

International Search Report and Written Opinion for corresponding International Application No. PCT/US2014/037358, dated Oct. 27, 2014 (15 pages).
Final Office Action for related U.S. Appl. No. 13/496,905 with related technology, dated Nov. 28, 2014 (17 pages).
Second Office Action for corresponding Chinese Application No. 201080052239.3, dated Nov. 19, 2014 (15 pages).
Chinese Office Action (English Translation) for related Chinese Application No. 201080052239.3, entered Apr. 11, 2014 (9 pages).
International Preliminary Report on Patentability for International Application No. PCT/US2012/060653, dated Apr. 22, 2014 (8 pages).
Japanese Office Action (English Translation) for related Japanese Application No. 2012-529930, entered Apr. 15, 2014 (6 pages).
Third Office Action, and English language translation thereof, in Chinese Application No. 201080052239.3, dated Jul. 1, 2015, 17 pages.
Patent Examination Report No. 1 for Australian Application No. 2014203223, dated Apr. 30, 2015 (3 pages).
Office Action with English translation for related South Korean Application No. 10-2012-7009817, dated Dec. 14, 2015 (13 pages).
Notification of Reasons for Rejection with English translation for related Japanese Application No. 2014-537187, dated Jan. 5, 2016 (4 pages).

* cited by examiner (C-C)

(D-D)

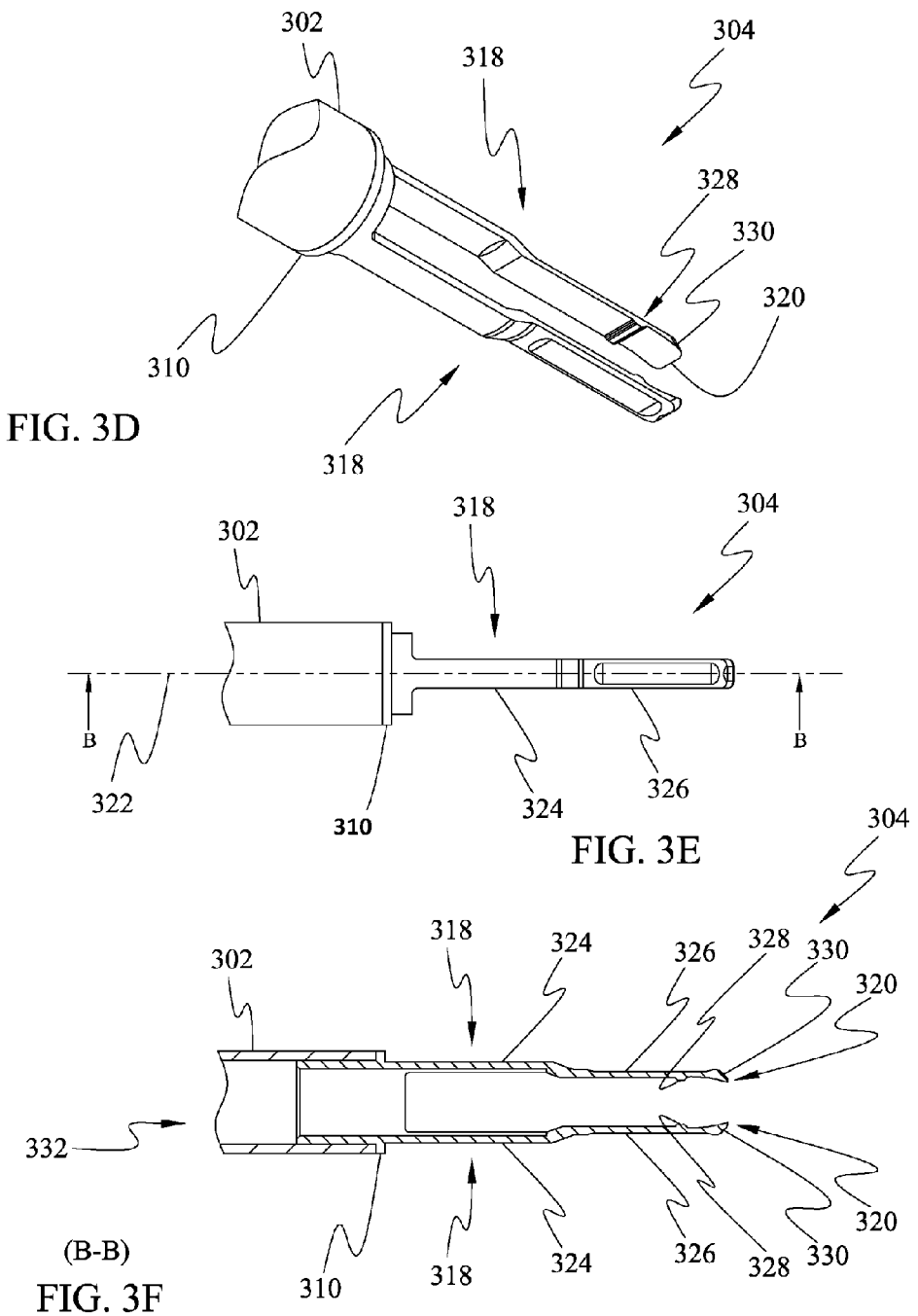

(A-A)

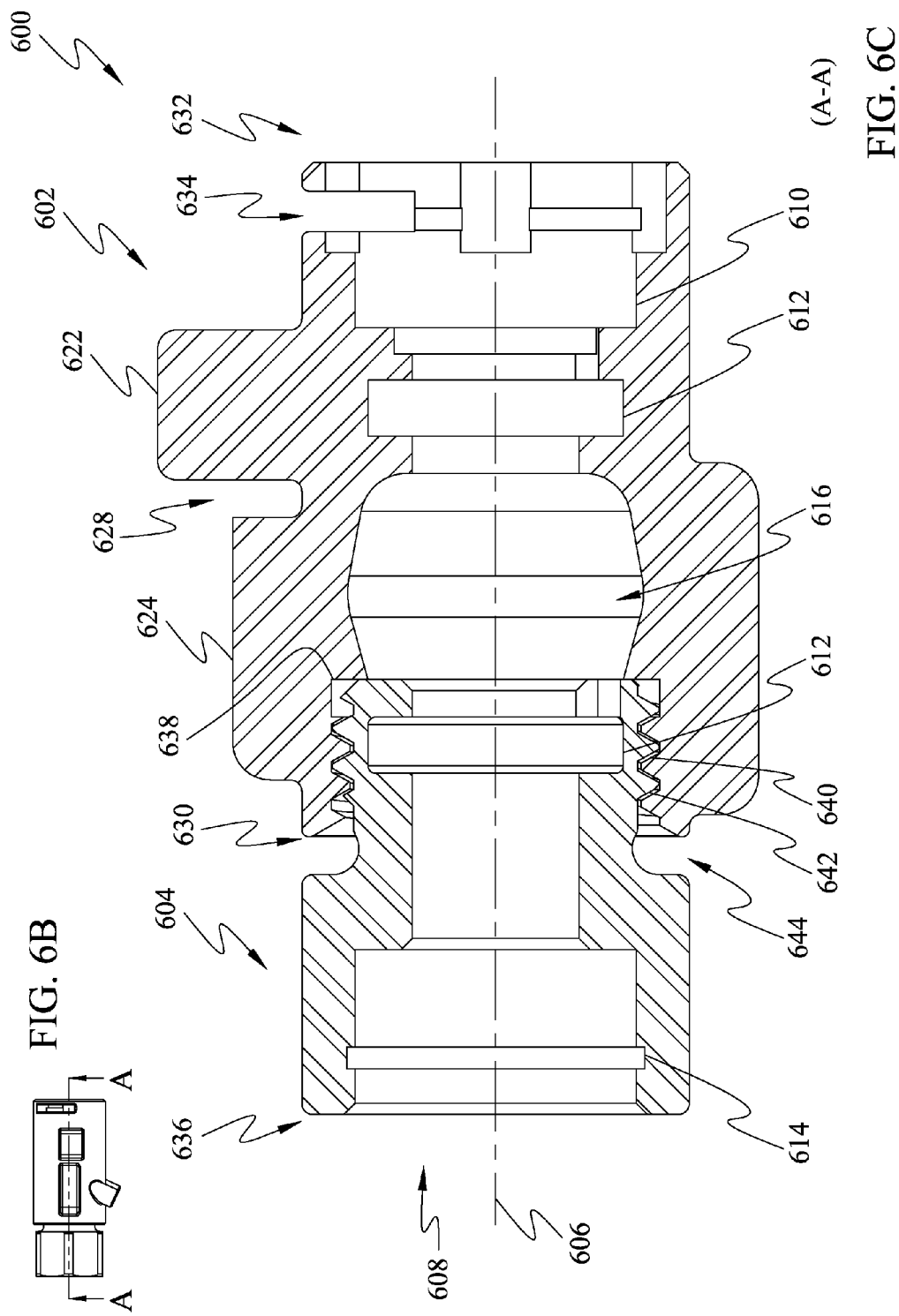

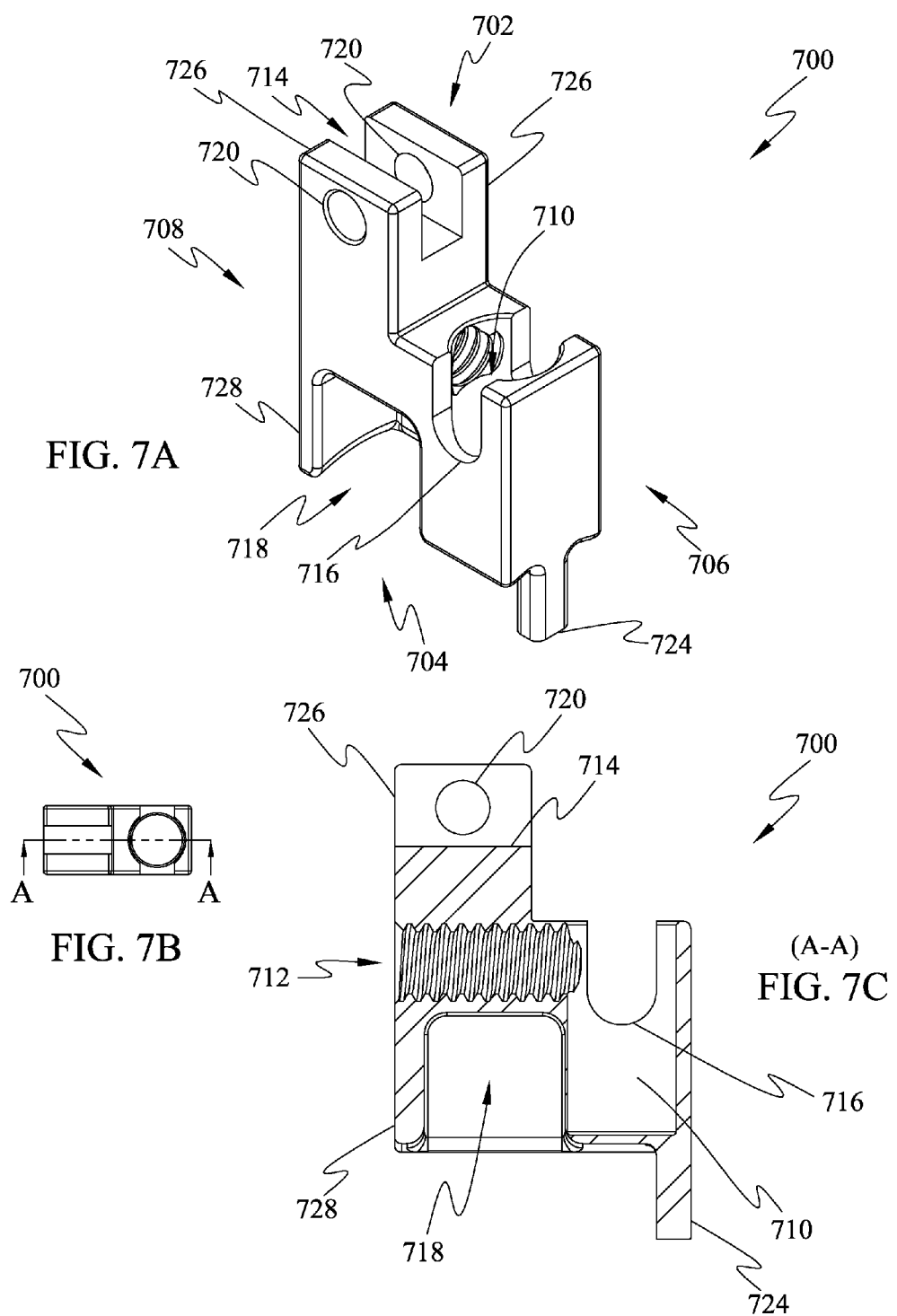

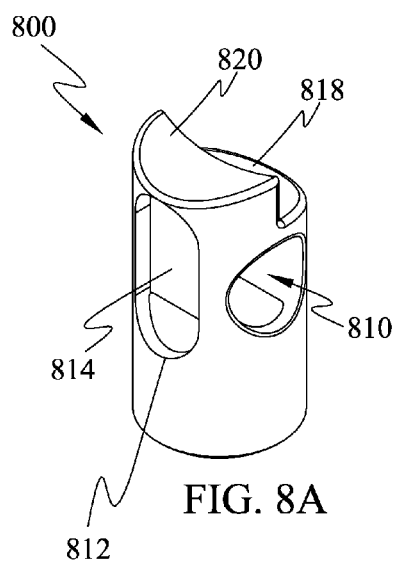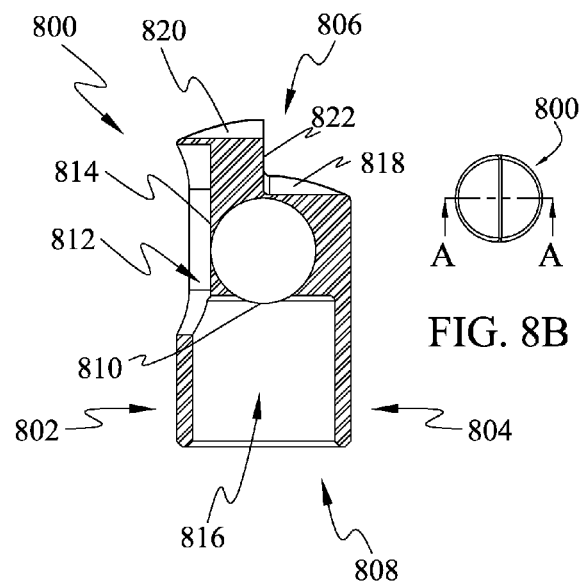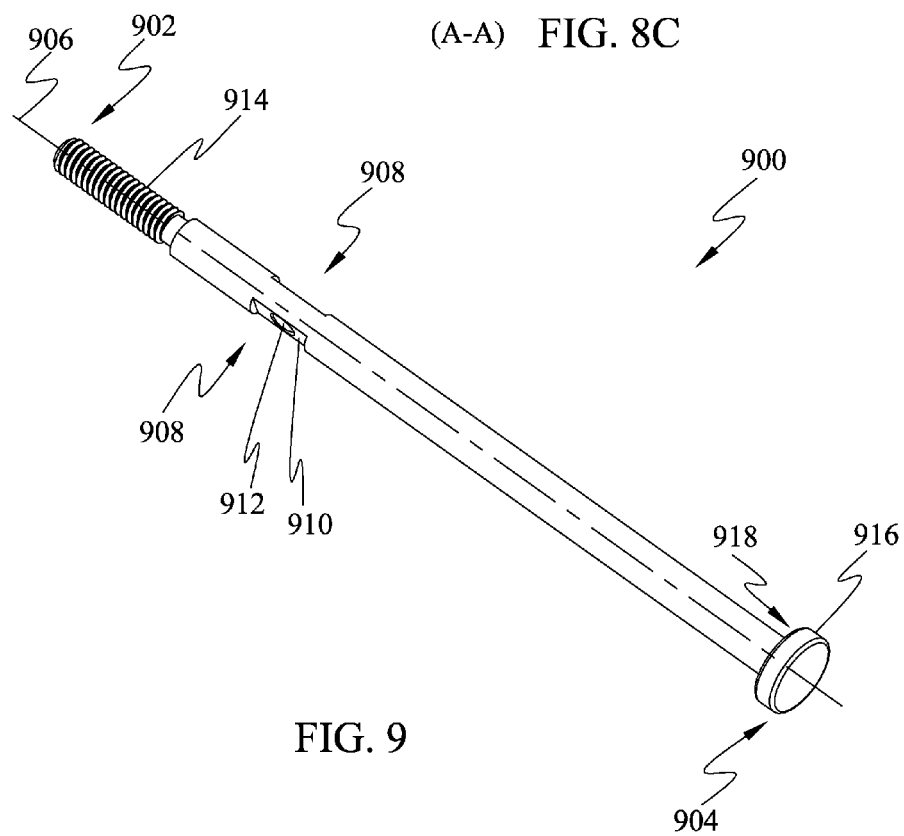

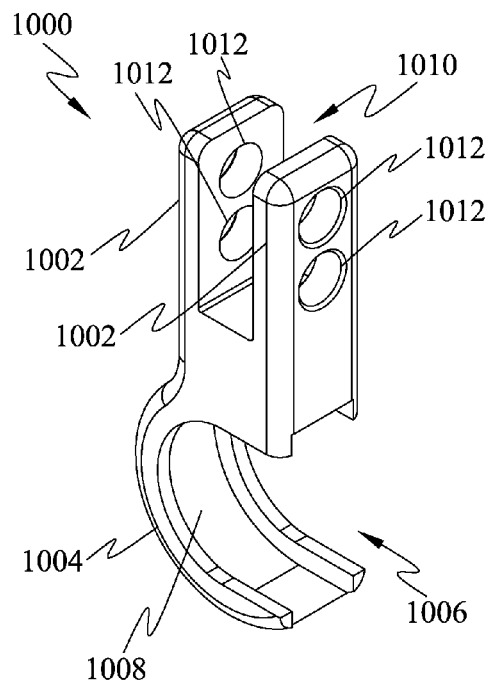
FIG. 10
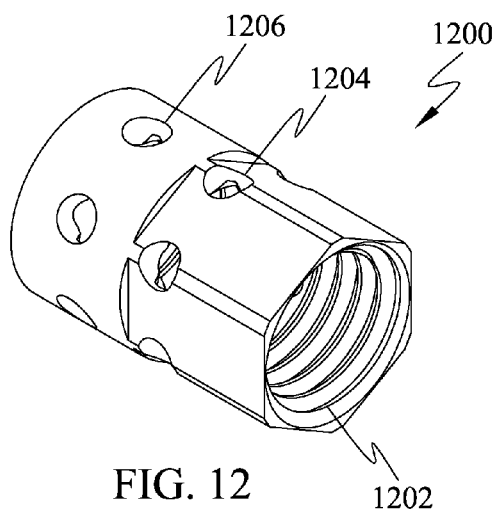
FIG. 12
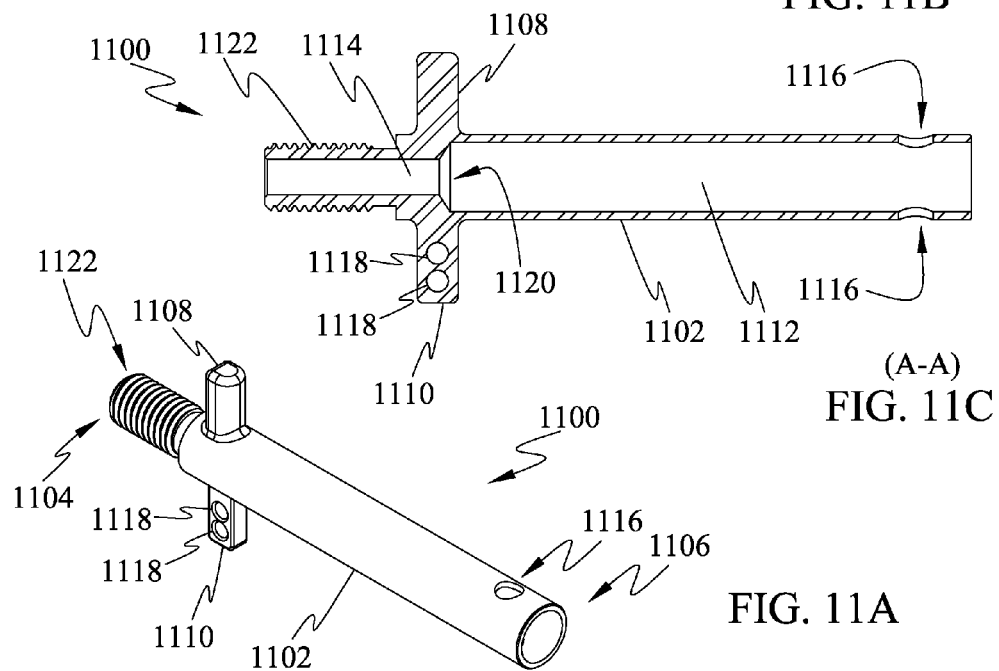
FIG. 11B
FIG. 11C
FIG. 11A (A-A)

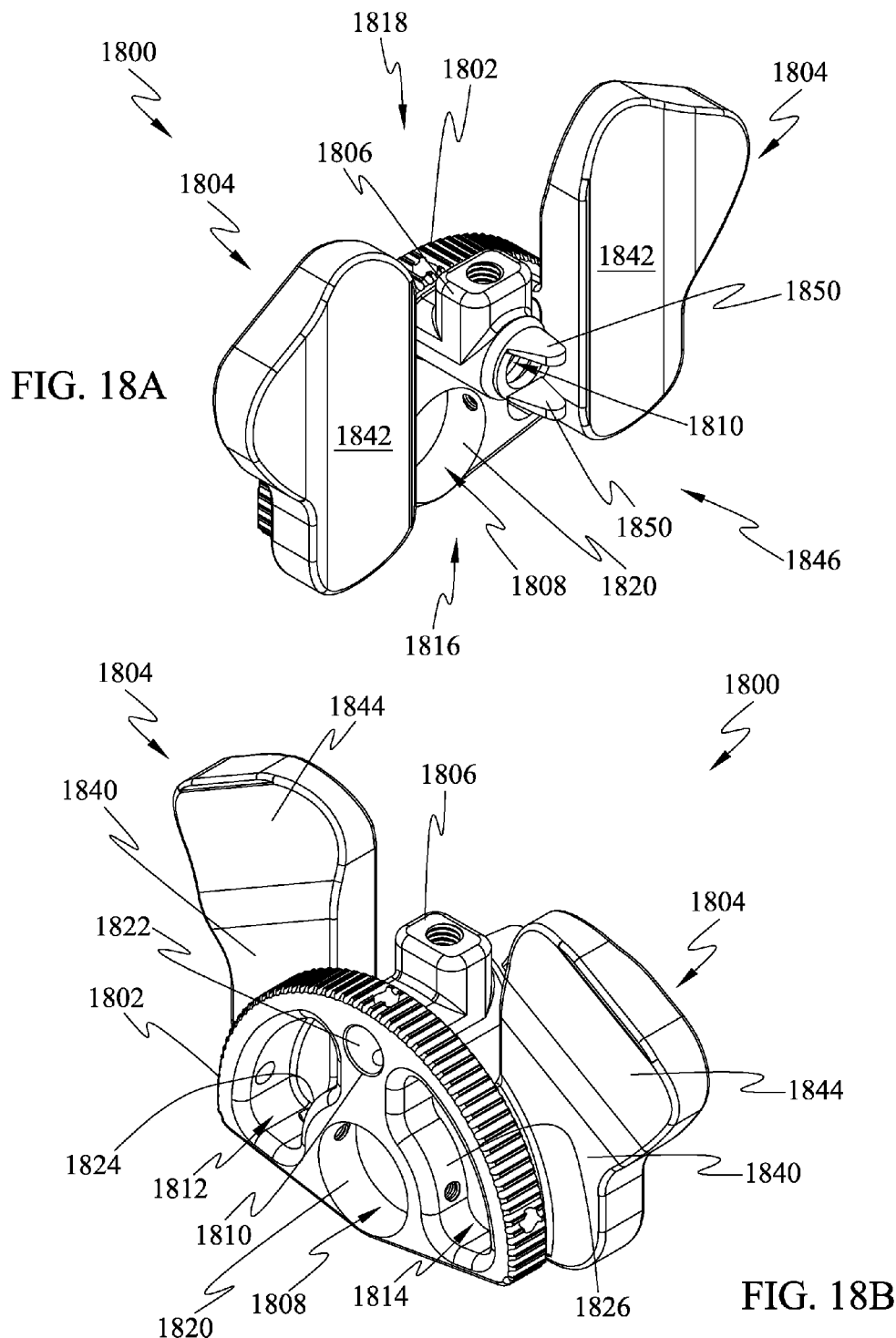

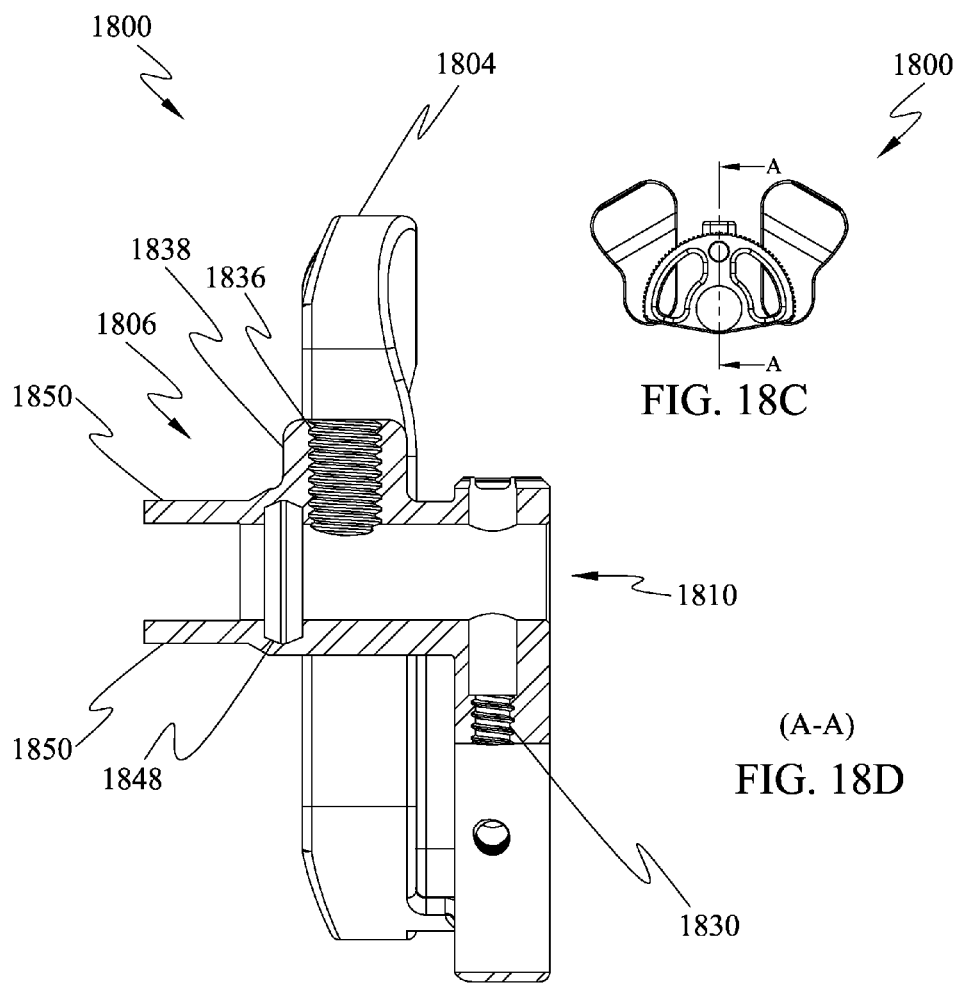
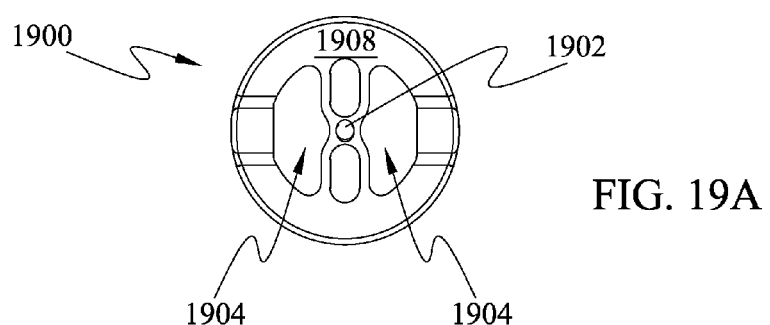

(A-A)

(A-A)

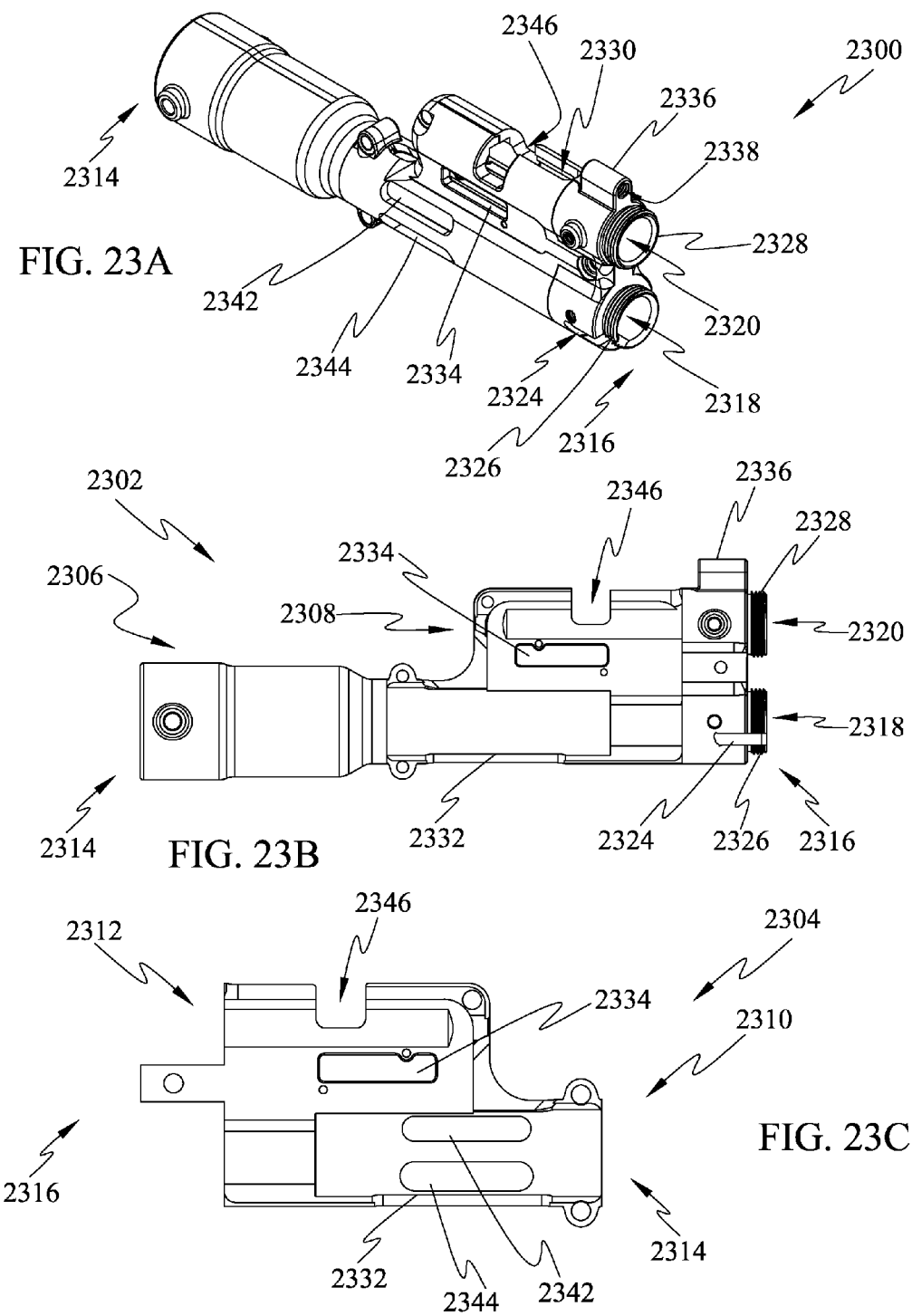

FIG. 24B (A-A)

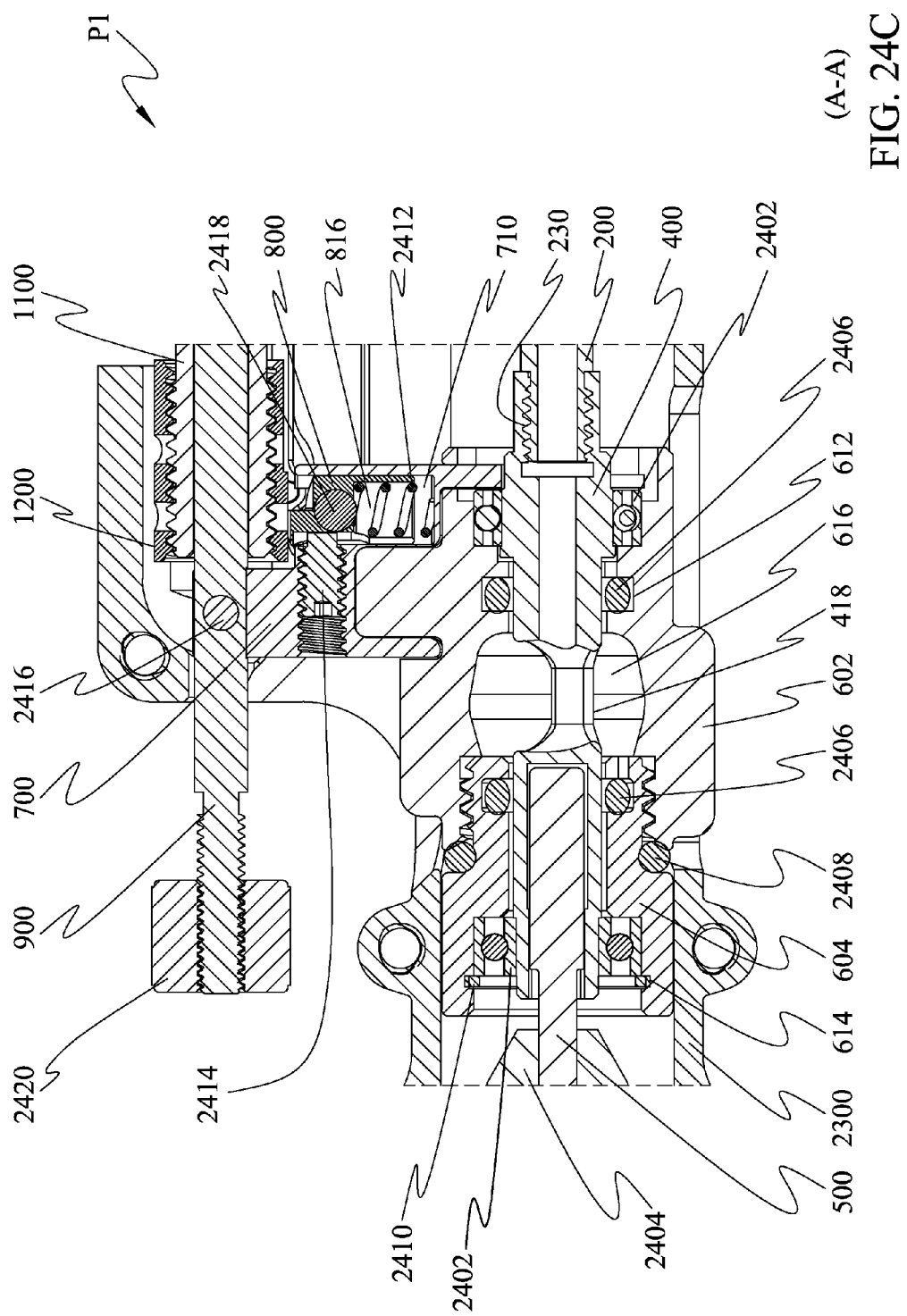
FIG. 24C (A-A)

(A-A)

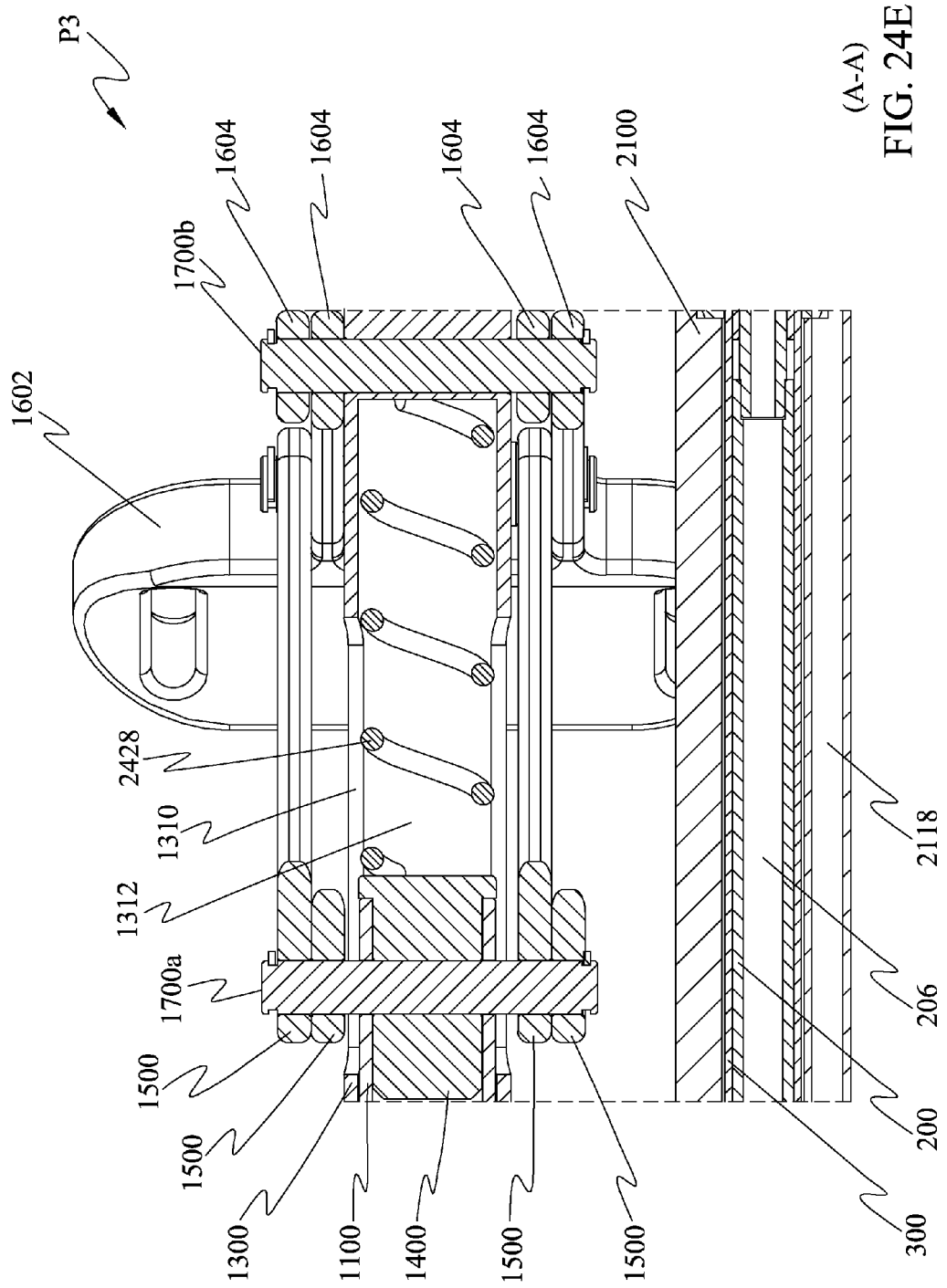

(A-A)

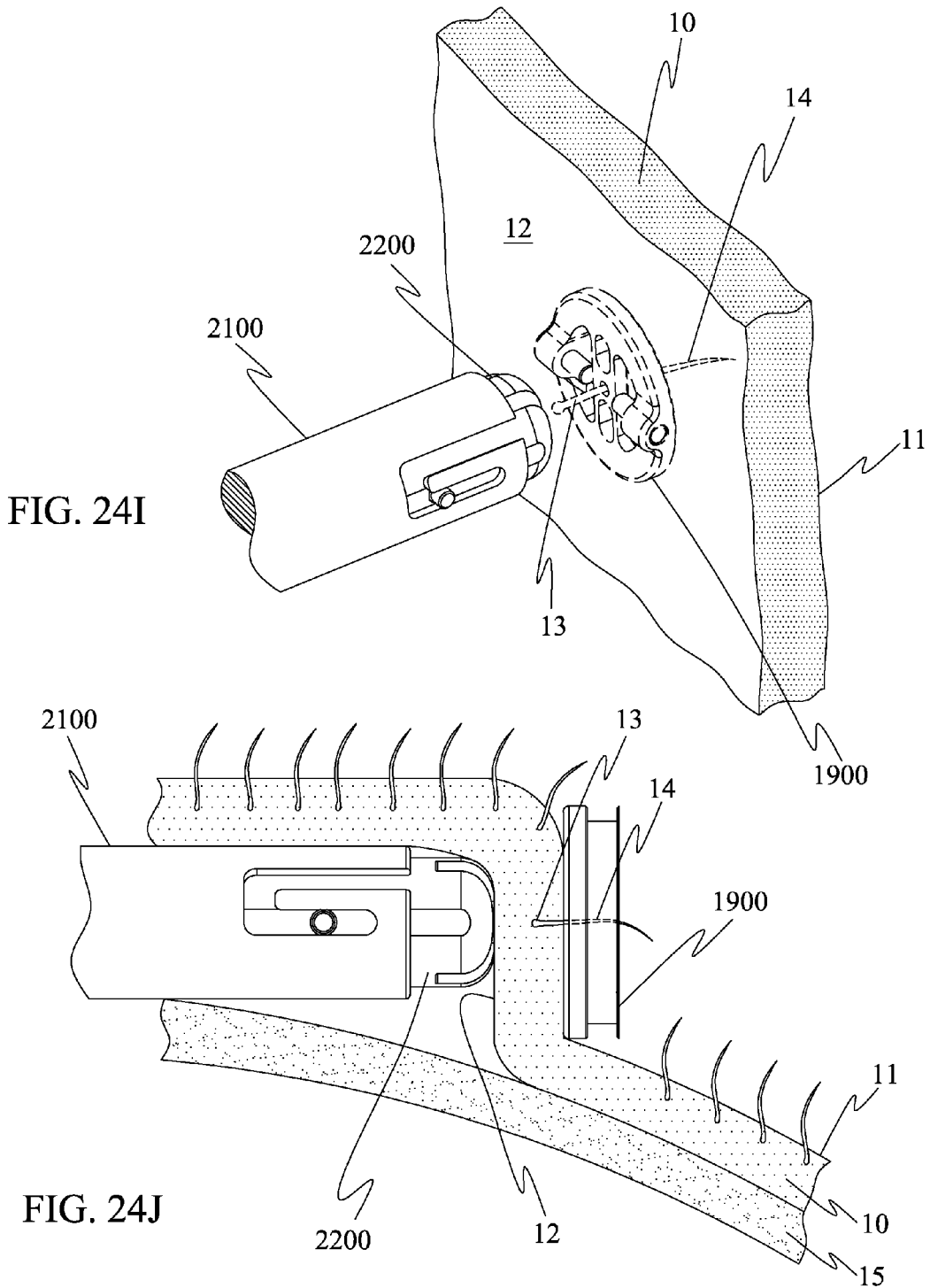

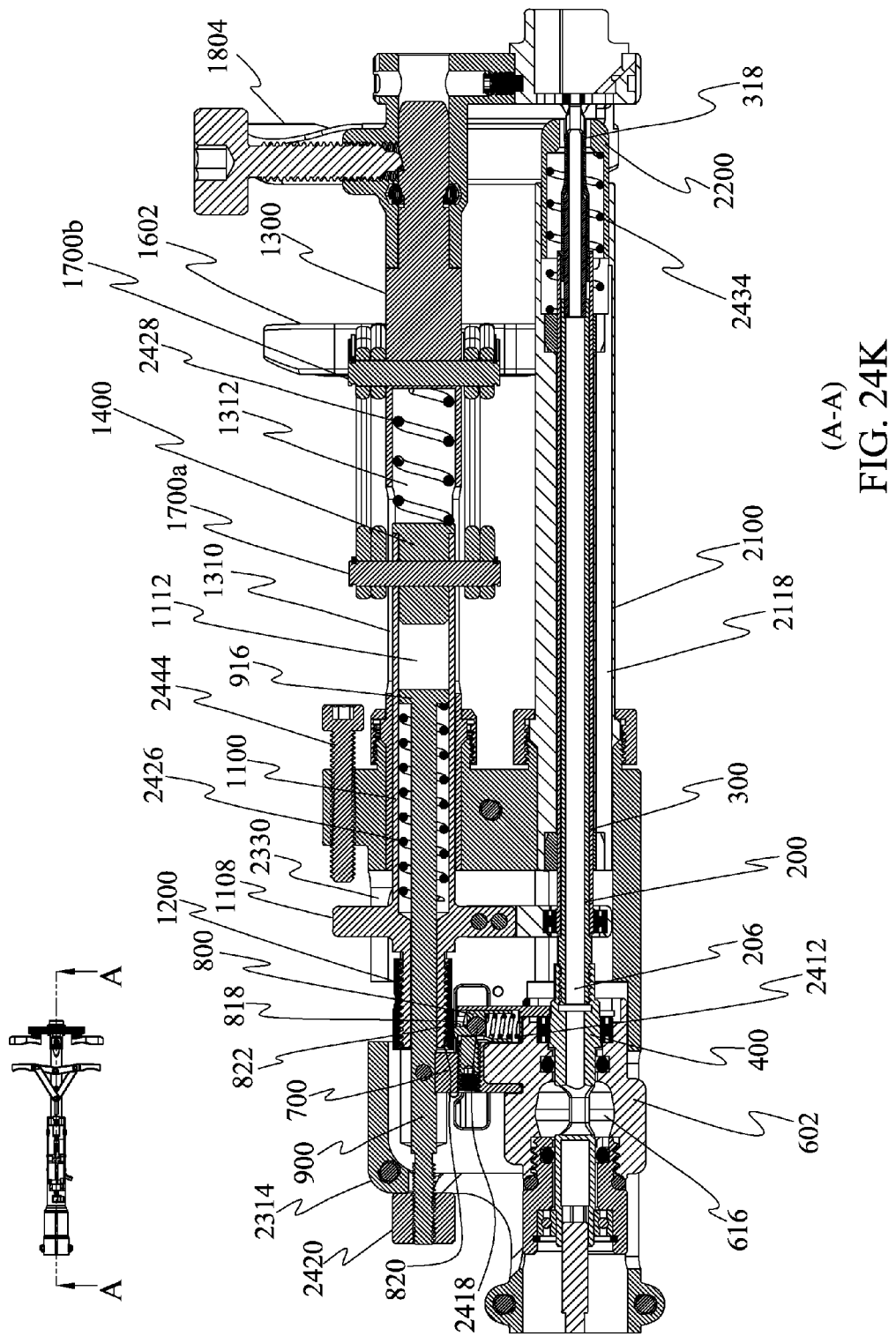
FIG. 24K (A-A)

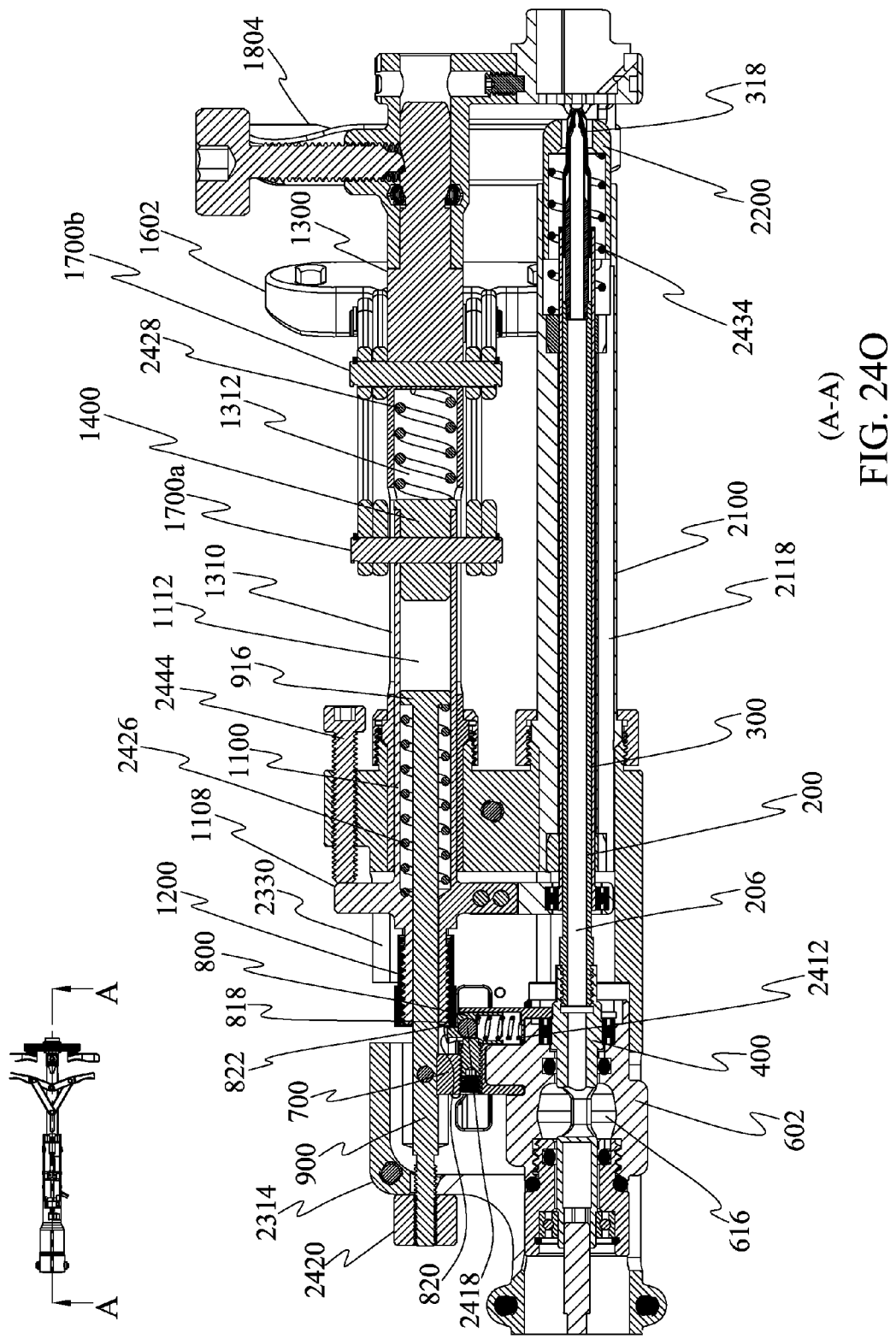
FIG. 24O (A-A)

(A-A)

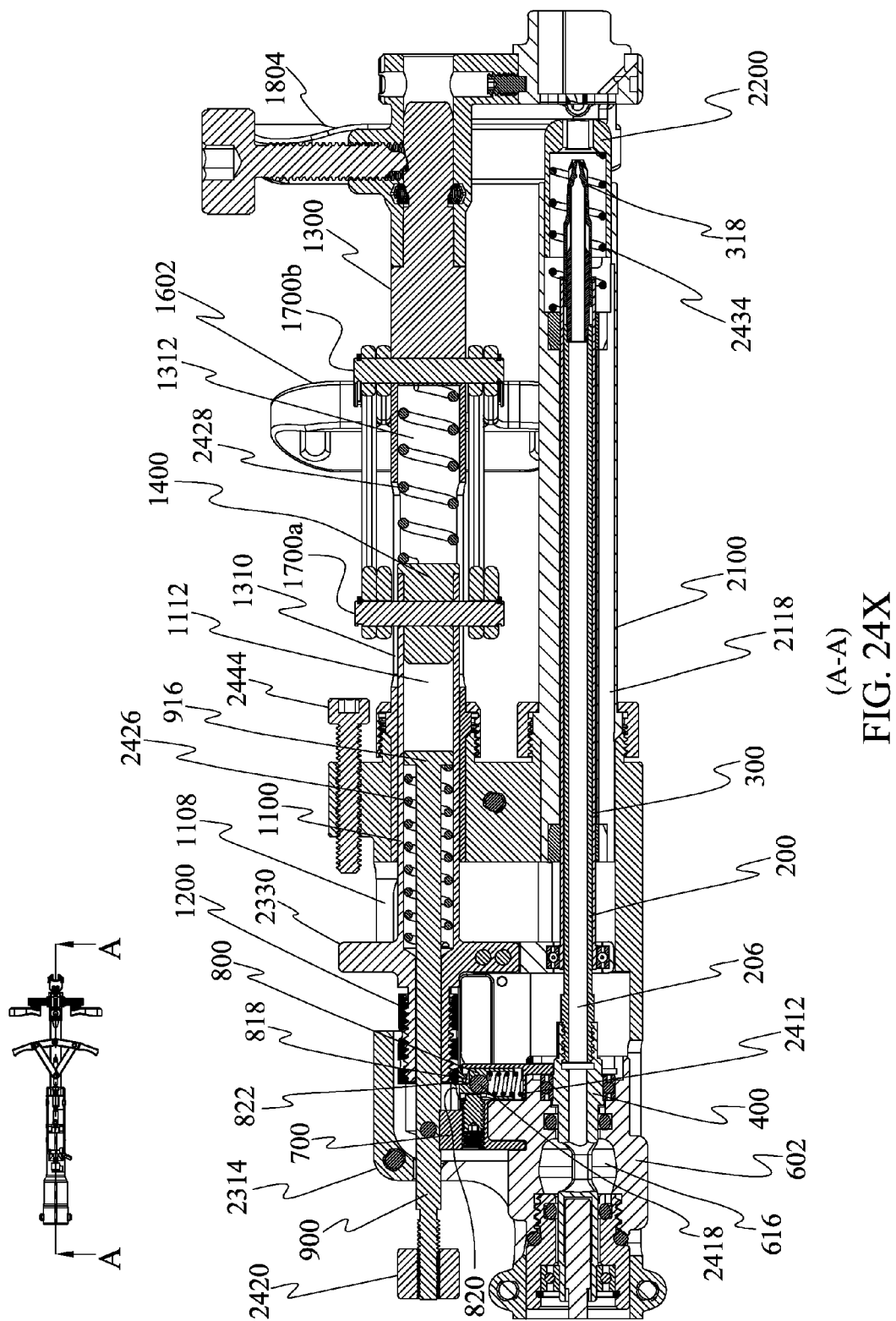
FIG. 24X (A-A)

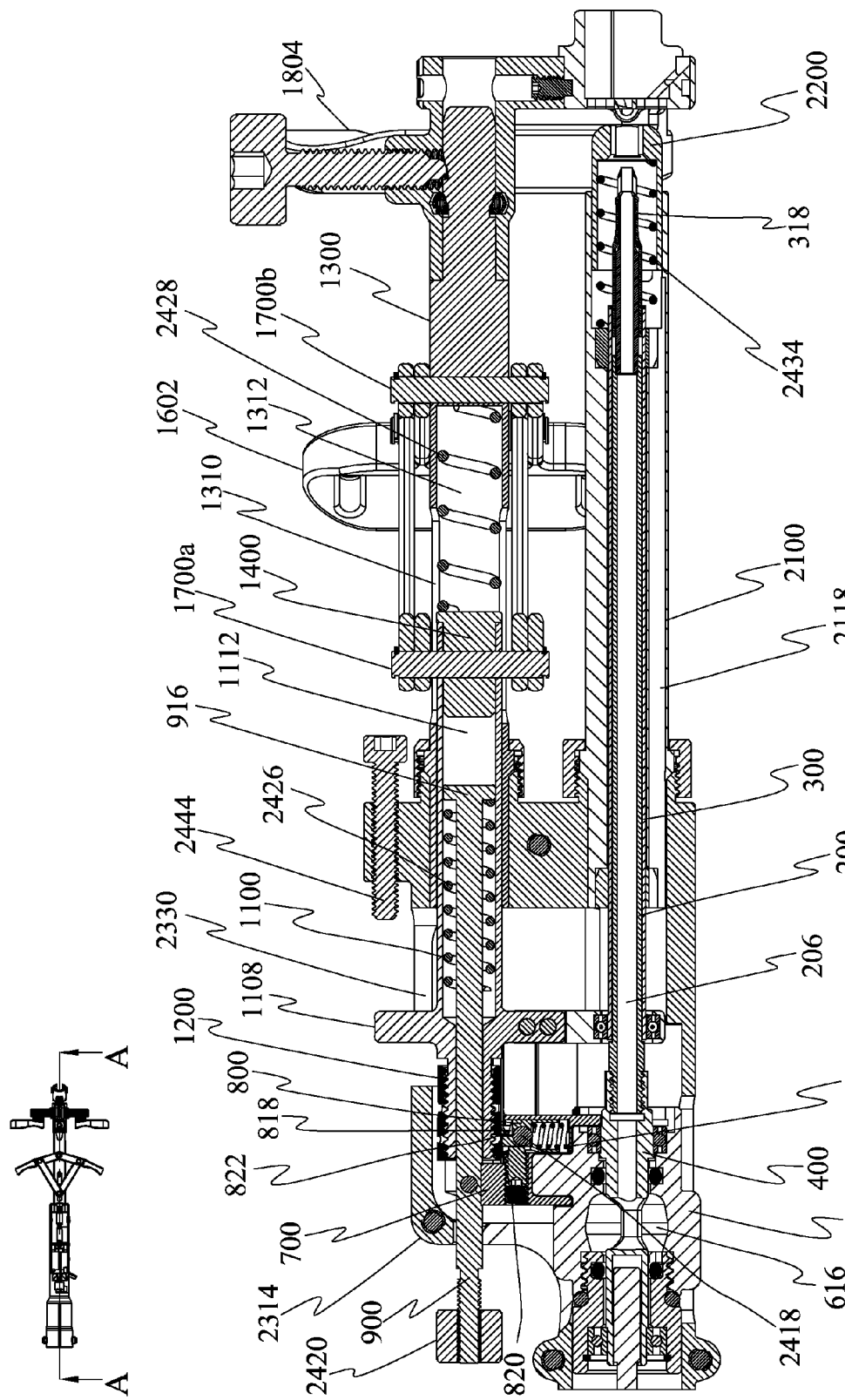
FIG. 24Z (A-A)

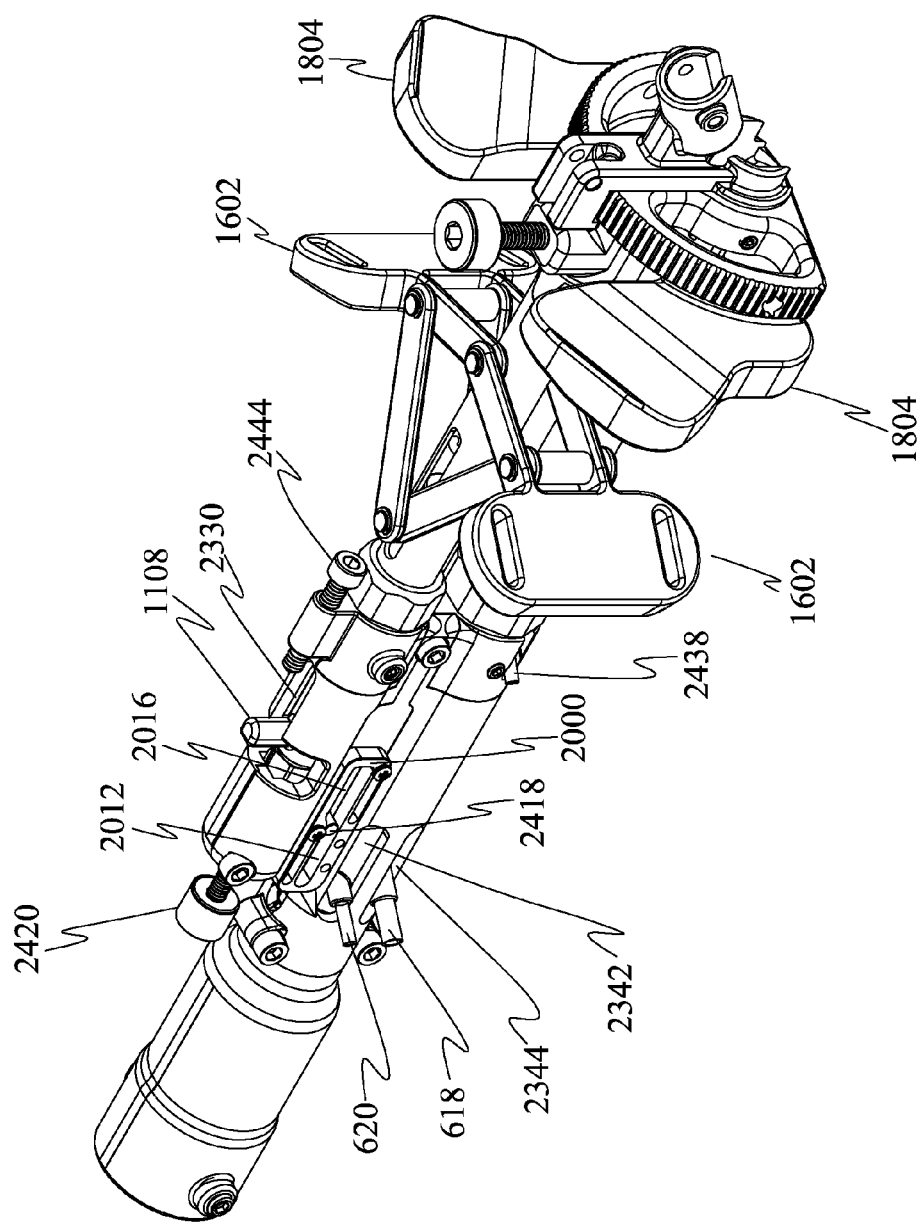
FIG. 24Z1

SYSTEM AND METHOD FOR EXTRACTION OF HAIR FOLLICLE

CROSS-REFERENCE TO RELATED APPLICATIONS

This application claims the benefit of prior U.S. Provisional Patent Application No. 61/821,098 filed May 8, 2013, and is entitled HAIR RESTORATION.

This application is a Continuation-in-part of pending prior U.S. patent application Ser. No. 13/654,252, filed Oct. 17, 2012, bearing publication number 2013/0096600, and is entitled HAIR RESTORATION, which claims priority to and the benefit of U.S. Provisional Patent Application No. 61/673,143 filed Jul. 18, 2012, and is entitled HAIR RESTORATION.

This application is a Continuation-in-part of pending prior U.S. patent application Ser. No. 13/496,905, filed Sep. 17, 2010, bearing publication number 2012/0215231, and is entitled HAIR RESTORATION SURGERY, which claims priority to and the benefit of U.S. Provisional Application No. 61/243,271, filed Sep. 17, 2009.

The above-identified documents are incorporated herein by reference.

BACKGROUND

1. Technical Field

The present disclosure relates to technique for extracting a target hair follicle from a donor site. More particularly, but not exclusively, the present disclosure relates to extracting the hair follicle from underneath an external surface of the skin.

2. Discussion of Related Art

Hair restoration may be carried out by extracting hair follicular units from the patient's donor area and transplanting them in the patient's recipient area, which may be a thinning area. Generally, the donor area is at the back and sides of the scalp.

Conventionally, a strip of tissues may be removed from the donor area. The strip may be then dissected into individual follicular units. The units may then be transplanted into the recipient area. It has been observed that application of this technique results in a linear scar formed at the donor area.

In another conventional technique, a hair follicle is extracted by punching a hole around the hair follicle, and then extracting the hair follicle. The hole is punched through the external surface of the skin. It has been observed that application of this technique may result in dotted scars formed at the donor area. Further, in this technique, the hair follicle may be transected, as the punch may not be aligned with the alignment of the hair follicle.

In light of the foregoing discussion, there may be a need to reduce scarring in the donor site, and reduce transection or denuding of hair follicle during extraction.

After the preparation of follicular unit grafts doctors make tiny holes in the patient's scalp at the recipient area where grafts are placed. The positioning and arrangement of follicular units depends upon aesthetic qualities of a hair transplant, case-by-case basis, depending on the patients' history of hair loss and likelihood of future hair loss.

Francisco Jimenez, MD, Ander Izeta, PhD, and Enrique Poblet, MD. "Morphometric Analysis of the Human Scalp Hair Follicle: Practical Implications for the Hair Transplant Surgeon and Hair Regeneration Studies" *Dermatol Surg* 4021; 37:58-64. This document is incorporated herein by reference in its entirety.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 3D is a close up perspective view of a distal portion of the second member of FIG. 3A;

FIG. 3E is a top view of the distal portion of FIG. 3D;

FIG. 3F is a sectional view about axis B-B of the distal portion of FIG. 3E;

FIG. 6B is a top view of the carriage of FIG. 6A;

FIG. 6C is a sectional view about axis A-A of the carriage of FIG. 6B;

FIG. 7A is a perspective view of a first connecting member of the system for extracting hair follicles of FIG. 1A;

FIG. 7B is a top view of the first connecting member of FIG. 7A;

FIG. 7C is a sectional view about axis A-A of the first connecting member of FIG. 7B;

FIG. 8A is a perspective view of a stop of the system for extracting hair follicles of FIG. 1A;

FIG. 8B is a top view of the stop of FIG. 8A;

FIG. 8C is a sectional view about axis A-A of the stop of FIG. 8B;

FIG. 9 is a perspective view of a first arm of the system for extracting hair follicles of FIG. 1A;

FIG. 10 is a perspective view of a second connecting member of the system for extracting hair follicles of FIG. 1A;

FIG. 11A is a perspective view of a second arm of the system for extracting hair follicles of FIG. 1A;

FIG. 11B is a top view of the second arm of FIG. 11A;

FIG. 11C is a sectional view about axis A-A of the second arm of FIG. 11B;

FIG. 12 is a perspective view of an adjustment sleeve of the system for extracting hair follicles of FIG. 1A;

FIGS. 18A and 18B are a perspective view of a external supporting member of the system for extracting hair follicles of FIG. 1A;

FIG. 18C is a front view of the external supporting member of FIG. 18A;

FIG. 18D is a sectional view about axis A-A of the external supporting member of FIG. 18C;

FIG. 19A is a front view of a counter pressure device of the system for extracting hair follicles of FIG. 1A;

FIG. 23A is a perspective view of a housing assembly of the system for extracting hair follicles of FIG. 1A;

FIG. 23B is a side view of a first component of the housing assembly of FIG. 23A;

FIG. 23C is a side view of a second component of the housing assembly of FIG. 23A;

FIG. 24B is a sectional view about the axis A-A of the systems of FIG. 24A;

FIG. 24C is a close-up view of a portion "P1" of the sectional view of FIG. 24B;

FIG. 24E is a close-up view of a portion "P3" of the sectional view of FIG. 24B;

FIGS. 24G-24Z1 illustrates working of the system for extracting hair follicles.

DETAILED DESCRIPTION

Figure 1A:
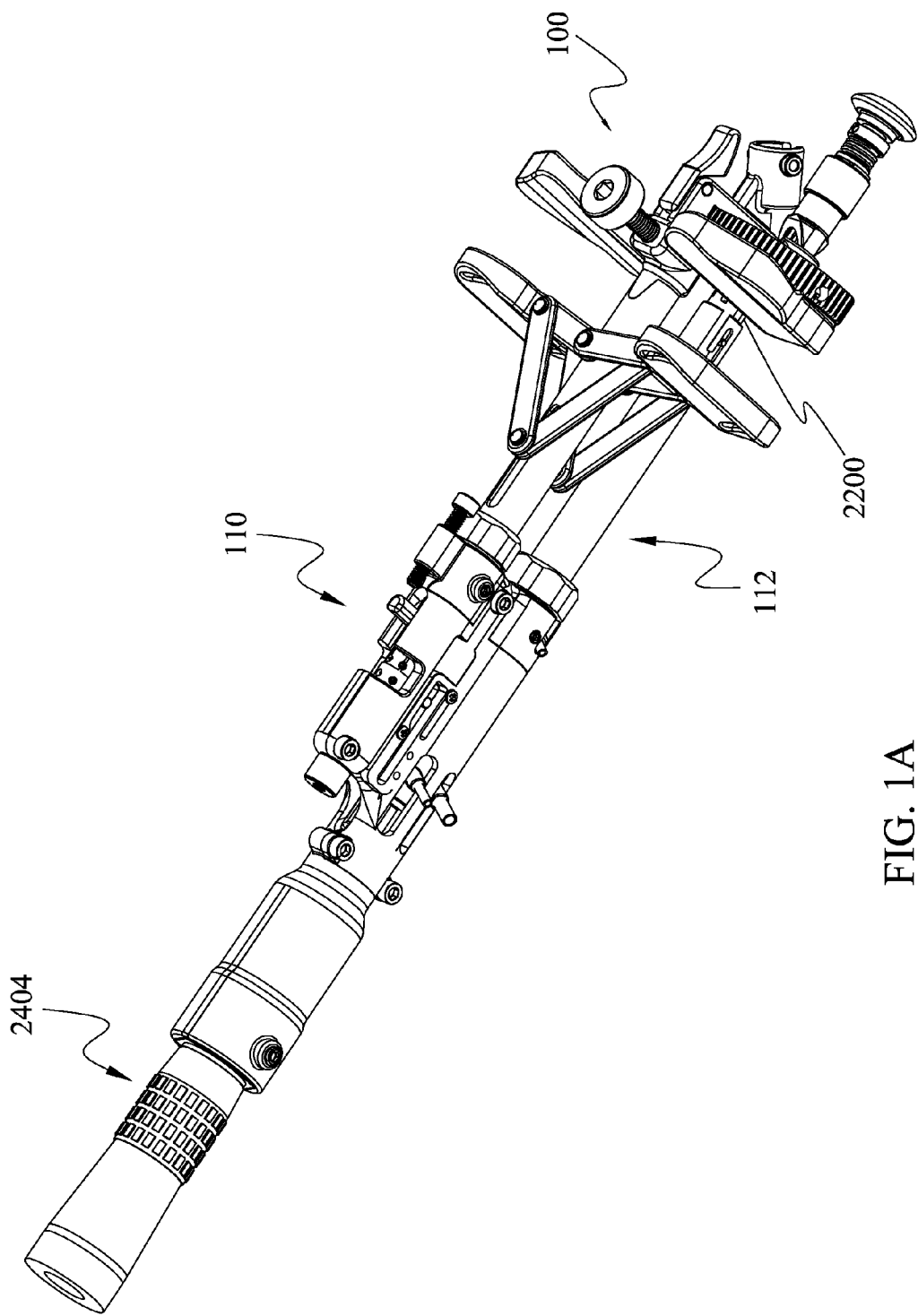
FIG. 1A is a perspective view of a system for extracting hair follicles and another system adapter with the first system to enable extraction of hair follicles.
Figure 1B:
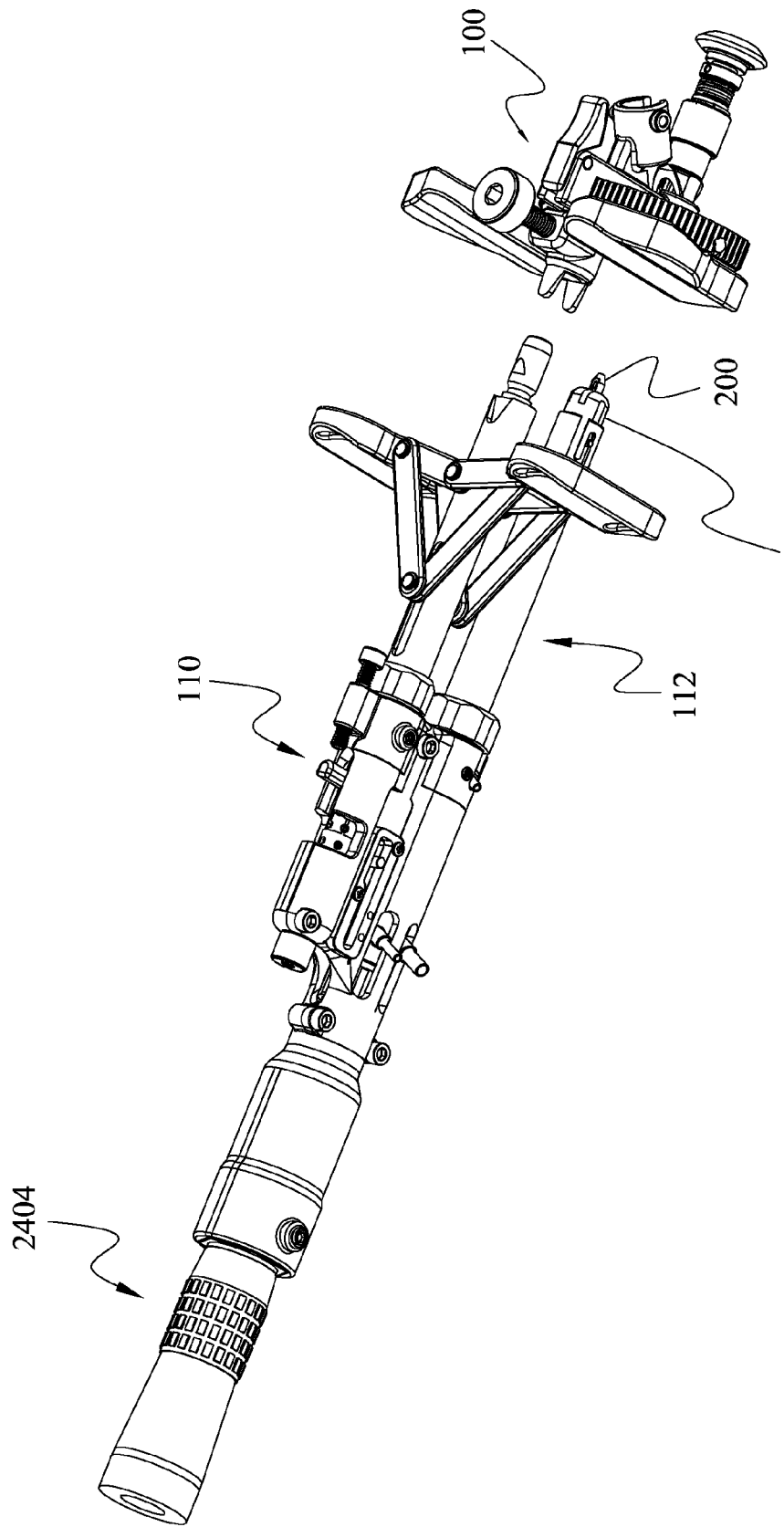
FIG. 1B is another perspective view of the systems of FIG. 1A.
Figure 1C:
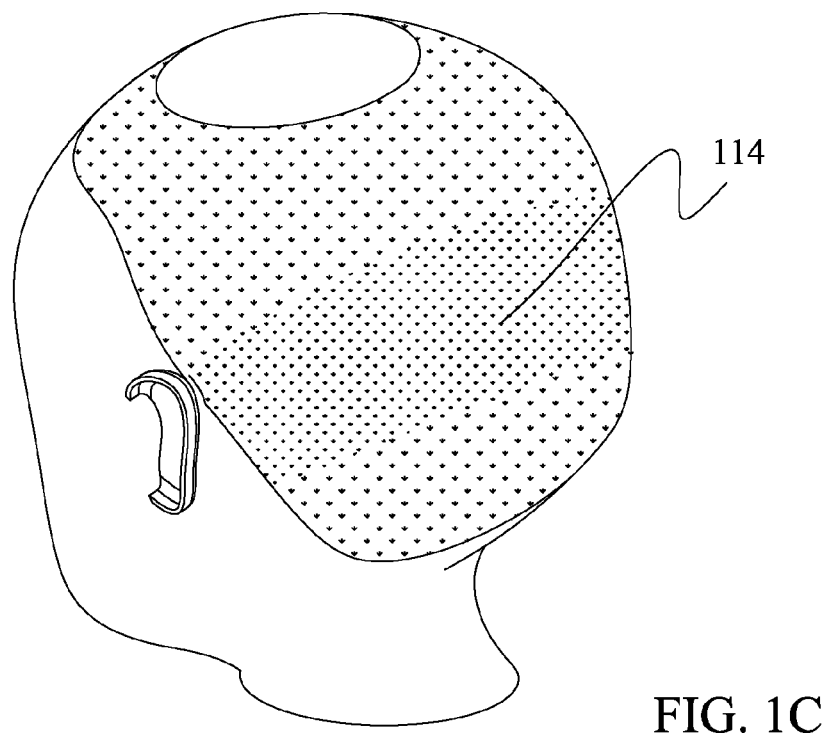
FIG. 1C is a perspective view of a human head.
Figure 1D:
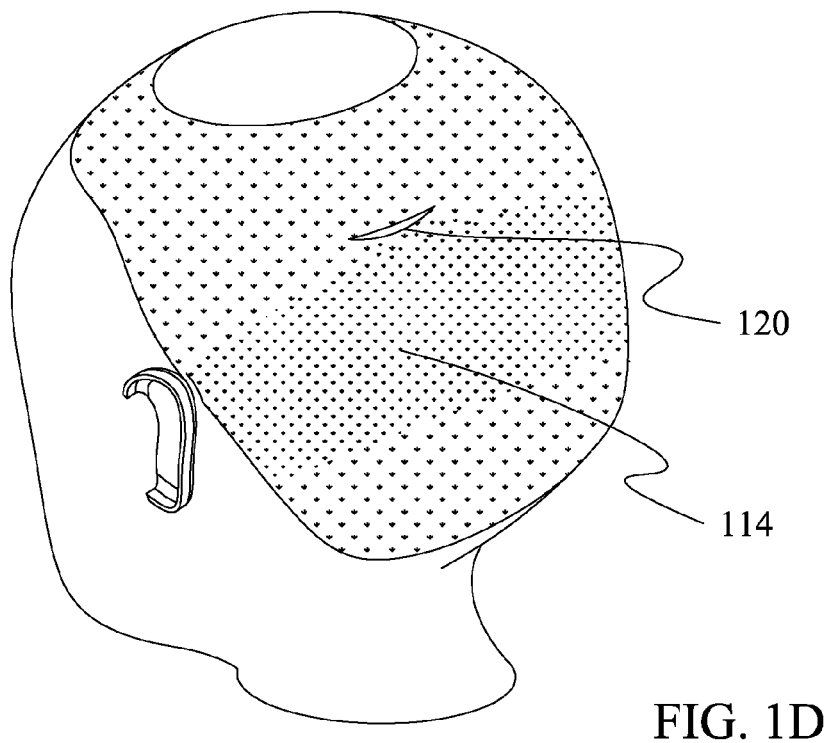
FIG. 1D is another perspective view of the human head of FIG. 1C in which an incision is made into the skin.
Figure 1E:
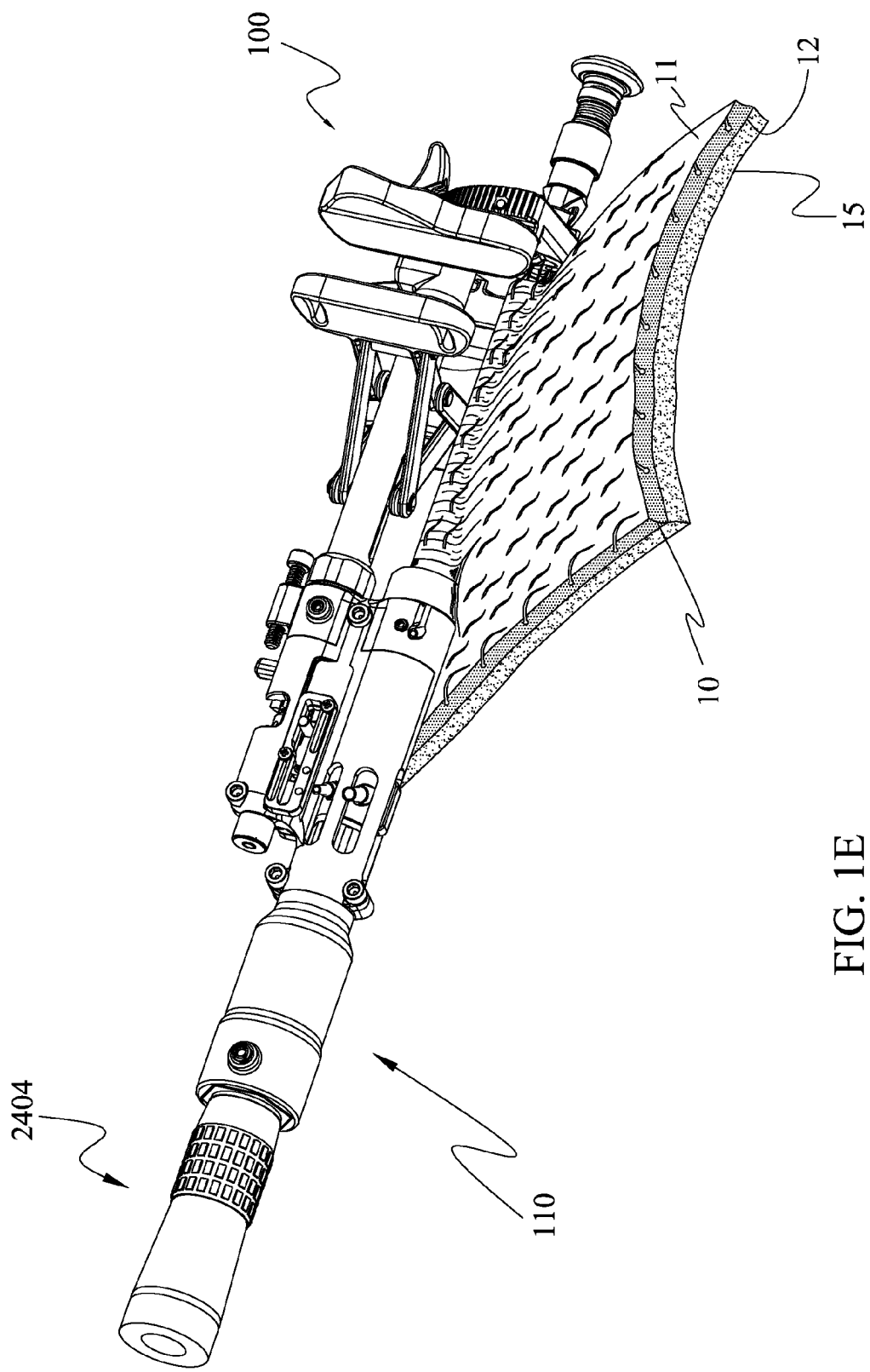
FIG. 1E is yet another perspective view of the system of FIG. 1A.
Figure 2A:
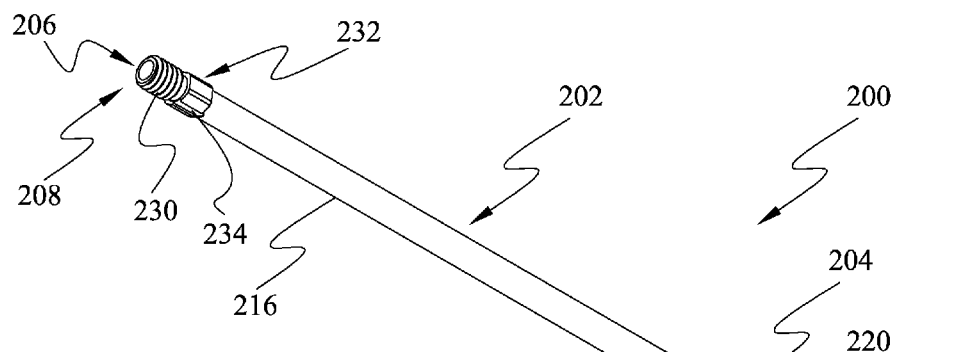
FIG. 2A is a perspective view of a first member of the system for extracting hair follicles of FIG. 1A.
Figures 2B, 2C:
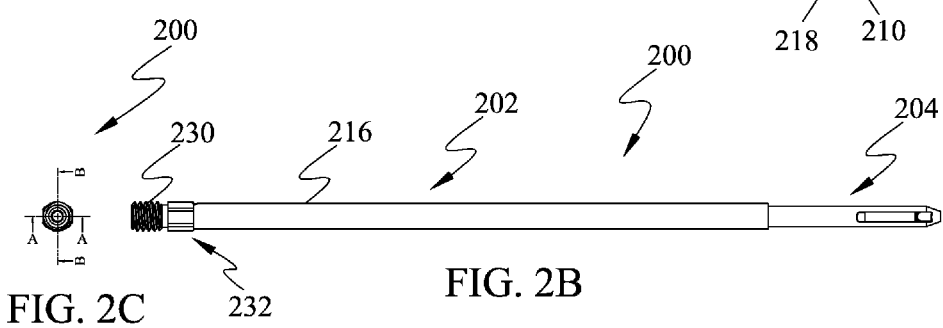
FIG. 2B is a top view of the first member of FIG. 2A.
FIG. 2C is a back view of the first member of FIG. 2A.
Figure 2D:
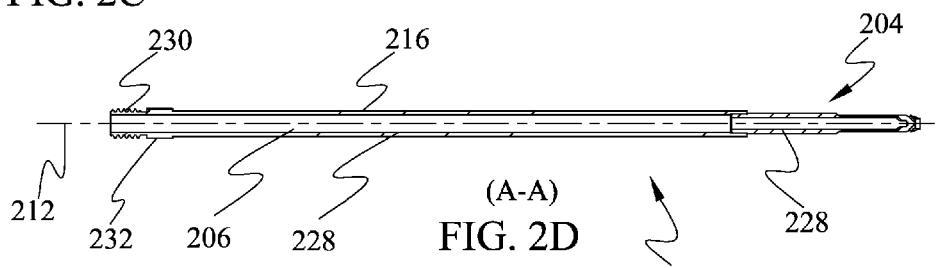
FIG. 2D is a sectional view about axis A-A of the first member of FIG. 2C.
Figure 2E:
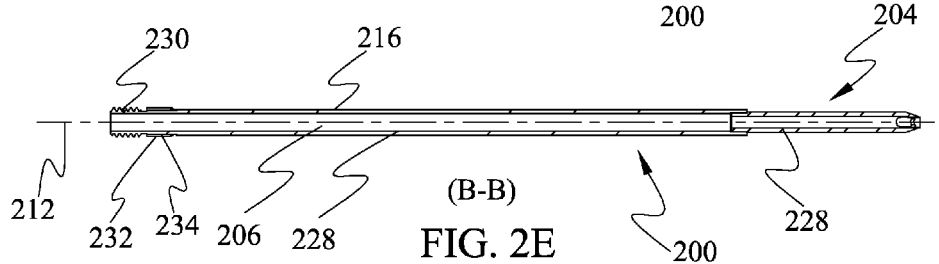
FIG. 2E is another sectional view about axis B-B of the first member of FIG. 2C.
Figure 2G:
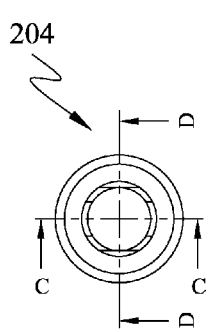
FIG. 2G is a back view of the distal portion of FIG. 2F.
Figure 2F:
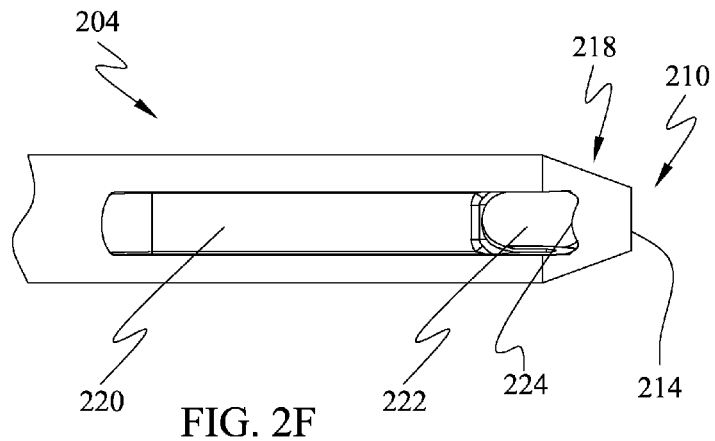
FIG. 2F is a close up top view of a distal portion of the first member of FIG. 2A.
Figure 2H:
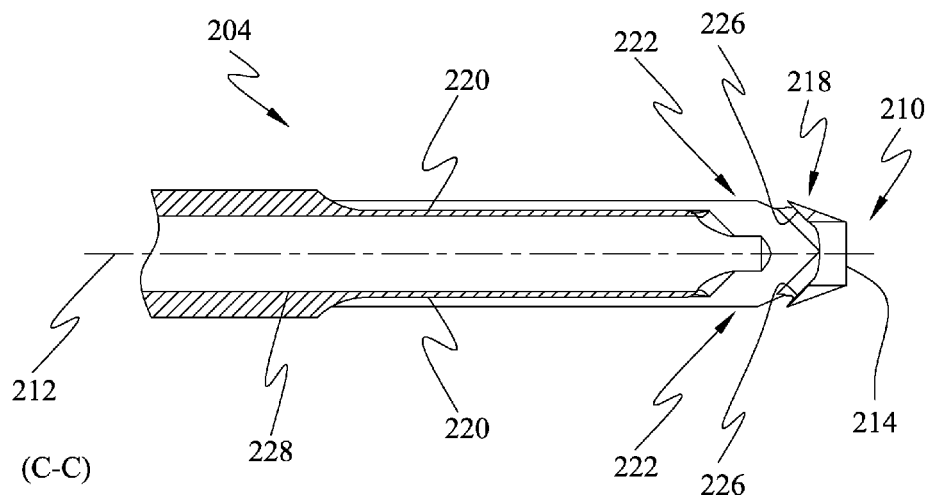
FIG. 2H is a sectional view about axis C-C of the distal portion of FIG. 2G.
Figure 2I:
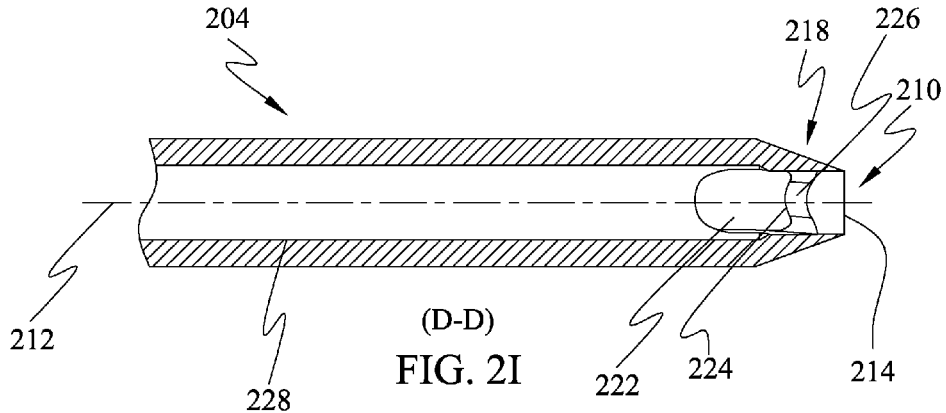
FIG. 2I is another sectional view about axis D-D of the distal portion of FIG. 2G.
Figure 3A:
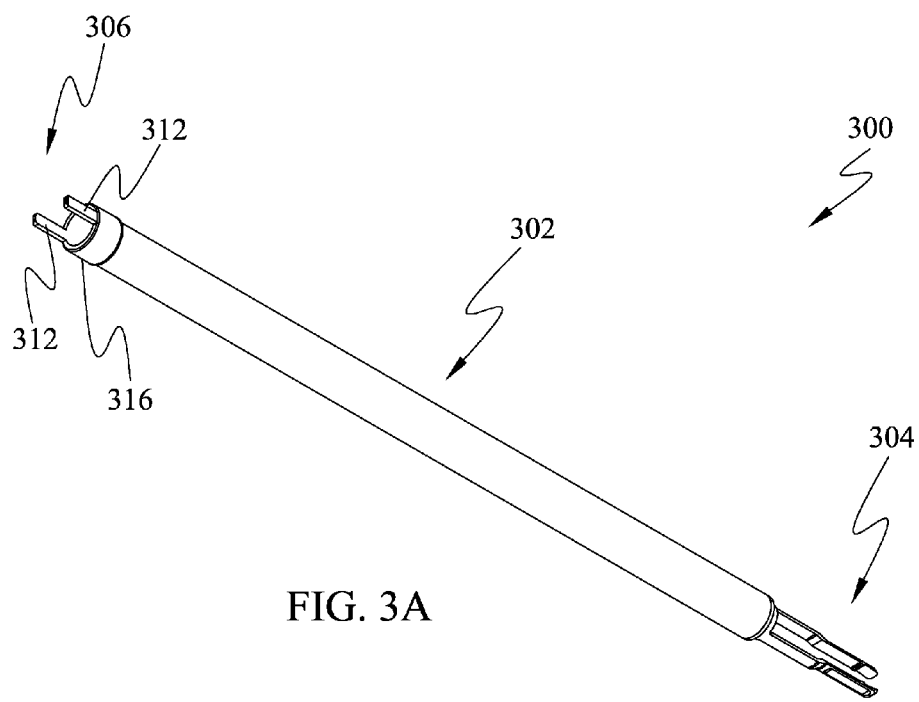
FIG. 3A is a perspective view of a second member of the system for extracting hair follicles of FIG. 1A.
Figure 3B:
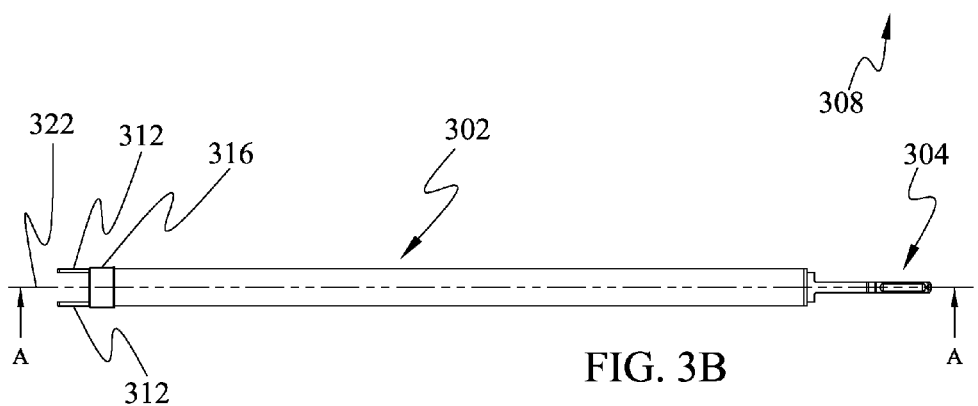
FIG. 3B is a top view of the second member of FIG. 3A.
Figure 3C:
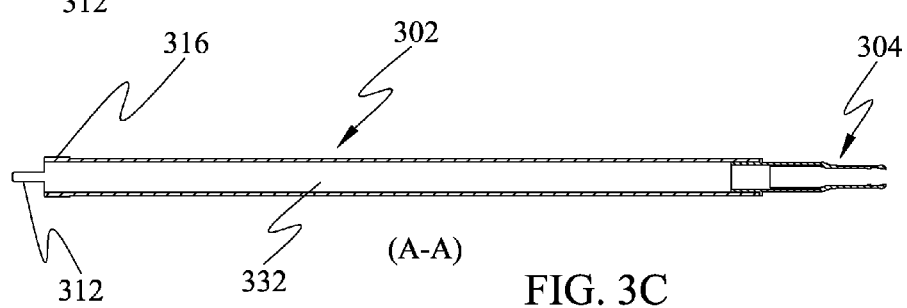
FIG. 3C is a sectional view about axis A-A of the second member of FIG. 3B.
Figure 4A:
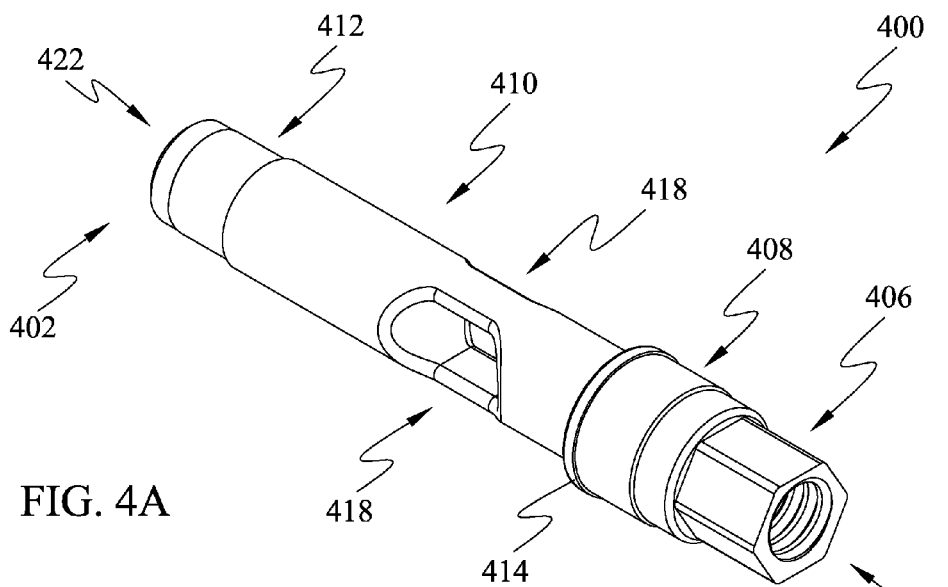
FIG. 4A is a perspective view of an adapter of the system for extracting hair follicles of FIG. 1A.
Figure 4B:
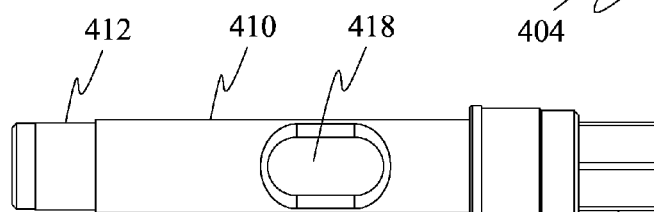
FIG. 4B is a top view of the adapter of FIG. 4A.
Figure 4C:
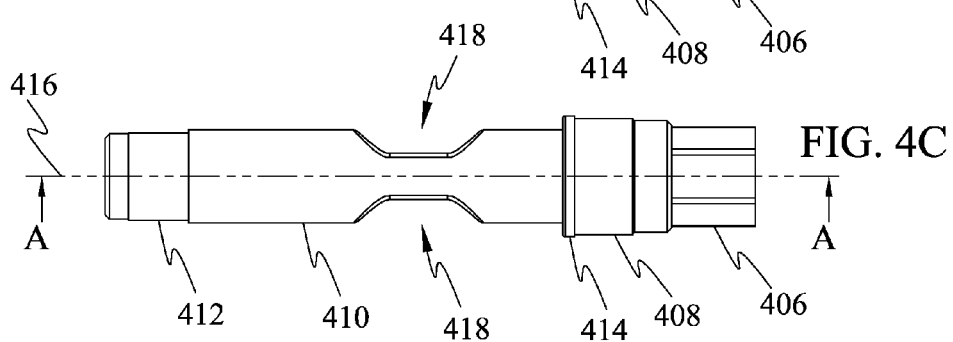
FIG. 4C is a side view of the adapter of FIG. 4A.
Figure 4D:
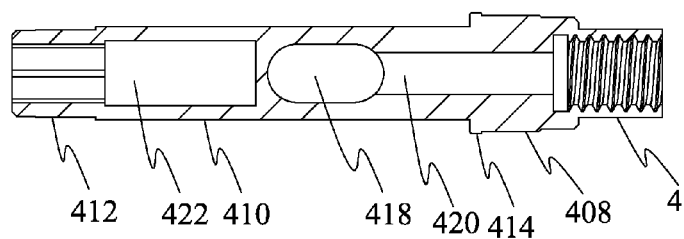
FIG. 4D is a sectional view about axis A-A of the adapter of FIG. 4C.

The disclosure may relate to extracting hair follicles from underneath an external surface of the skin, without punching holes through the external surface of the skin.

The following description illustrates principles, which may be applied in various ways to provide many different alternative embodiments. This description is not meant to limit the inventive concepts in the appended claims. The principles, structures, techniques, and methods disclosed herein may be adapted for use in other situations where a target tissue portion is to be extracted from a tissue region. For example, the present technology may be adapted for use in dermatology, cosmetic surgery, and/or general surgery. Although this disclosure focuses on extraction of head hair for subsequent transplantation, the disclosed technology also applies to extraction of hair follicles from other parts of the human body, such as the arm pit and pelvic regions, for the purpose of permanent hair removal. This technology also applies to extraction of other tissues, such as extraction of pathological tissues in the deeper layers of the skin or other body tissues, biopsy and/or removal of tissue being one example.

While exemplary embodiments of the present technology have been shown and described in detail below, it will be clear to the person skilled in the art that changes and modifications may be made without departing from its scope. As such, that which is set forth in the following description and accompanying drawings is offered by way of illustration only and not as a limitation. In addition, one of ordinary skill in the art will appreciate upon reading and understanding this disclosure that other variations for the technology described herein can be included within the scope of the present technology.

Referring to FIGS. 1A-1E, a device or system 110 may be used for extracting hair follicles from underneath an external surface 11 of the skin 10. The system 110 may be used with a system 100, which may be used for altering the alignment of hair follicles or tissue. The system 110 may be configured such that a portion 112 of the system 110 may be inserted under the skin 10 to access and/or cut through a tissue at a donor region 114 of the head. The system 110 may include a first member 200 which may be used to extract a portion of the hair follicle. The system 110 may further include a tissue stabilizing member 2200 which may be configured to apply pressure against or around a tissue comprising a hair follicle. The system 110 may be inserted into an area underneath the external surface 11 of the skin 10 by making an incision 120 on the external surface 11 of the skin 10 proximal or at the donor region 114. The first member 200 and the tissue stabilizing member 2200 may enter the area underneath the external surface 11 of the skin 10. The first member 200 may include a cutting edge configured to cut through the tissue. The system 100 may be positioned external to the overlying surface of the skin opposite to the first member 200. The system 100 may include a counter pressure device configured to interface with the external surface 11 of the skin 10, such that the tissue having the hair follicle is disposed between the counter pressure device and the tissue stabilizing member 2200, such that the tissue stabilizing member 2200 is disposed underneath the external surface 11 of the skin 10 and the counter pressure device is disposed over the external surface 11 of the skin 10.

The system for extracting hair follicles from underneath an external surface of the skin may include a first member and a second member. The first member and the second member may be configured to be moved underneath the skin. The first member may be a cylindrical shaft defining a first bore and having a cutting edge at its distal end. The second member may also be a cylindrical shaft configured to receive the first member. The second member may include a pair of arms towards its distal end. Both the first member and the second member may be configured to rotate about its longitudinal axis and also translate along its longitudinal axis. The system may include a tissue stabilizing member. The tissue stabilizing member may press around the tissue having the hair follicle from underneath the skin. The first member may translate towards the tissue while being rotated. As the first member translates into the tissue, the tissue is cut or cored by the cutting edge of the first member, and may create a channel in which the cut or cored tissue may be disposed. Subsequently, the second member may be translated relative to the first member. The relative translation of the second member may enable the arms of the second member to extend into the first bore of the first member through apertures provided on the cylindrical body of the first member close to its distal end. The arms of the second member may meet inside the first bore of the first member, thereby clipping the tissue that has been cut or cored by the first member. The tissue or the hair follicle may be aligned, for example by the system 100, with the longitudinal axis of the first member before cutting the tissue.

Referring to FIGS. 2A-2I, the system 110 may include a first member 200. The first member may be a first means for cutting or coring a tissue. The first member 200 may be a coring cannula. The first member 200 may be configured to be moved below an external surface of the skin. The first member 200 may be a cylindrical member formed of two sub parts. The first part may be a coring cannula base 202 and the second part may be a coring cannula 204. The first member 200 may instead be a monolithic part. The coring cannula base 202 and the coring cannula 204 may be engaged, assembled and/or mated to form the first member 200. The first member 200 may define a first bore 206 extending from a distal end 210 to a proximal end 208 of the first member 200 along the longitudinal axis 212 of the first member 200.

A cutting edge 214 may be defined at the distal end 210. The cutting edge 214 may be configured to cut through the tissue. A portion of the external cylindrical surface 216 of the first member 200 towards the distal end 210 may be inclined or may converge towards the longitudinal axis 212 until it reaches the cutting edge 214, to define a conical configuration 218.

The first member 200 may include at least one slot (any number of slots may be provided) or at least one aperture. Alternatively, the first member 200 may include a pair of slots 220 and a pair of apertures 222. The slots 220 may be recessed into the external surface 216 of the first member 200 close to the distal end 210 as compared to the proximal end 208. The slots 220 may be disposed diametrically opposite to each other, or may be placed in any variety of configurations.

Each of the apertures 222 may be defined between the cutting edge 214 and the slots 220. The apertures 222 may be defined diametrically opposite to each other. Each of the apertures 222 may adjoin corresponding slots 220. The aperture 222 may be defined such that an arched edge 224 bulging towards the slot 220 may be defined on the external surface 216. The edge 224 may be arched, non-arched, or may include any other structure or surface profile in order to form the edge 224. The aperture 222 may be defined by an inclined surface 226 disposed between the arched edge 224 and an inside surface 228 of the first member 200.

A threaded surface 230 may be defined at the proximal end 208 of the first member 200. A shoulder 232 may be defined adjacent to the threaded surface 230. The shoulder 232 may define one or more slots 234.

Provision of the coring cannula 204 that may be adapted with the coring cannula base 202 may enable replacement of the coring cannula 204 with an alternate coring cannula which may have a desired cutting diameter.

Referring to FIGS. 3A-3F, the system 110 may include a second member 300. The second member 300 may be a second means for clipping the tissue. The second member 300 may be formed of two components, namely a clipping cannula base 302 and a clipping cannula 304. Alternatively, the second member 300 may be a monolithic part. The second member 300 may have a proximal end 306 and a distal end 308. The clipping cannula 304 and the clipping cannula base 302 may be engaged, for example by friction fit, welding, or other connection, to form the second member 300, such that the clipping cannula 304 is disposed towards the distal end 308. The clipping cannula 304 may define an annular ring 310 over its external surface. The annular ring 310 may interface with the edge of the clipping cannula base 302, thereby restricting the clipping cannula base 302 from sliding further towards the distal end 308 of the second member 300.

At the proximal end 306 of the second member 300 one or more longitudinally extending engagement protrusions 312 may be provided. The engagement protrusions 312 may be received by the slots 234 defined in the shoulder 232 provided in the first member 200, so that the torque from the first member 200 is transferred to the second member 300. The engagement protrusions 312 and slots 234 configuration may enable alignment of the arms 318 with the slots 220. An annular protrusion 316 may be provided adjacent to the engagement protrusions.

At the distal end 308 of the second member 300, one or more arms 318 may be provided. In the figures a pair of arms 318 is illustrated. The pair of arms 318 may define a tip 320 at the distal end 308. The pair of arms 318 may be disposed diametrically opposite to each other. Each arm 318 may have a first portion 324 that may be parallel to the longitudinal axis 322 of the second member 300. Further, the arm 318 may include a second portion 326, which may also be parallel to the longitudinal axis 322. However, the second portion 326 may be closer to the longitudinal axis 322, as compared to the first portion 324. The arm 318 may include an intermediate portion, which may be inclined, and may be present between the first portion 324 and the second portion 326. An inner surface of the second portion 326 may define one or more protrusions 328 extending towards the longitudinal axis 322. The protrusions 328 may reduce friction while sliding the second member 300 or the arm 318 over the slot 222 provided in the first member 200. The protrusions 328 may facilitate bending of the arms 318 towards the longitudinal axis 322, when the second member 300 is slid over the first member 200.

The tip 320 may define a slanted surface 330. The slanted surface 330 may compliment the slanted or inclined surface 226 defining the aperture 222 in the first member 200. The slanted surface 330 of the tip 320 may interface and slide against the inclined surface 226 of the first member 200 when the second member 300 is slid. The interface between the slanted surfaces 330, 226 may enable the arms to translate in to the first bore 206 towards the longitudinal axis 212.

Referring to FIGS. 4A-4D, the system 110 may include an adapter 400. The adapter 400 may have a proximal end 402 and a distal end 404. The adapter 400 may include a first portion 406, a second portion 408, a third portion 410 and a fourth portion 412. The first portion 406 may be provided towards the distal end 404, and may define a hexagonal cross-section. The second portion 408 may adjoin the first portion 406, and may define a circular cross-section. An annular shoulder 414 may be provided in the second portion 408 towards the third portion 410, and may have a diameter greater than the diameter of rest of the second portion 408. The third portion 410 may be adjacent to the annular shoulder 414, and may define a circular cross-section. The fourth portion 412 may be adjacent to the third portion 410, and may define a circular cross-section.

The radial distance of external surface of each of the first portion 406, the second portion 408, a third portion 410 and a fourth portion 412 from a longitudinal axis 416 of the adapter 400 may be different from each of the portions, such that a step is formed between two adjacent external surfaces.

The third portion 410 may define one or more apertures 418. A pair of apertures 418 is illustrated in the figures. The apertures 418 may be defined diametrically opposite to each other. The aperture 418 may be in the form of an opening provided through the external surface of the adapter 400, such that the aperture 418 defines an oblong or oval configuration from a top view. The opening may define a "U" shaped configuration from a side view, such that the arms of the "U" shaped configuration diverge as they extend away from the horizontal portion of the "U" shaped configuration. The edges of the aperture 418 may be curved, without defining hard angles, thereby preventing damage to hair follicles that may pass through the aperture 418.

The adapter 400 may define a bore 420 extending from the distal end 404 until the aperture 418. The bore 420 may have a threaded surface at the distal end to facilitate engagement with the threads 230 of the first member 200.

The adapter 400 may further define another bore 422 extending from the proximal end 402 towards the aperture 418, however, the bore 422 may terminate before reaching aperture 418, such that, the bore 422 has only one opening at the proximal end 402. A portion of the inner surface defining the bore 422 may define a polygonal cross section. A power shaft 500 (illustrated in FIG. 5) may be received in the bore 422 such that the power shaft is capable of translating in the bore 422, while transferring torque to the adapter 400, owing to the polygonal cross section of the portion of the hole 422.

Figure 5:
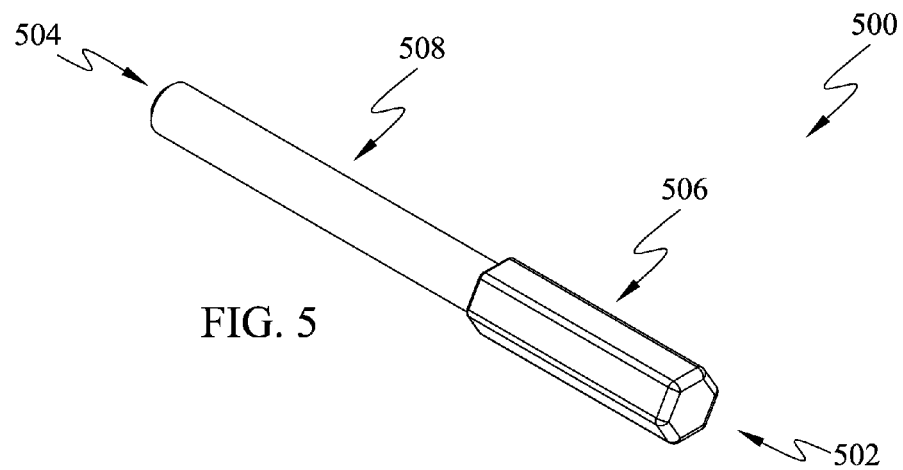
FIG. 5 is a perspective view of a power shaft of the system for extracting hair follicles of FIG. 1A.

Referring to FIG. 5, the system 110 may include a power shaft 500. The power shaft 500 may have a distal end 502 and a proximal end 504. A first portion 506 may be provided towards the distal end 502. A second portion 508 may be defined, such that it starts from one end of the first portion 506 and extends until the proximal end 504.

The first portion 506 may define a hexagonal cross-section or polygonal cross section. The first portion may be received by the bore 422 defined in the adapter 400. The polygonal cross section of the first portion 506 may enable transferring of the torque to the adapter 400, when the power shaft 500 is rotated. The second portion 508 may define a circular cross-section, and may be engaged to a power tool that is capable of rotating the power shaft 500. The power shaft 500 may be a part of a power tool.

Figure 6A:
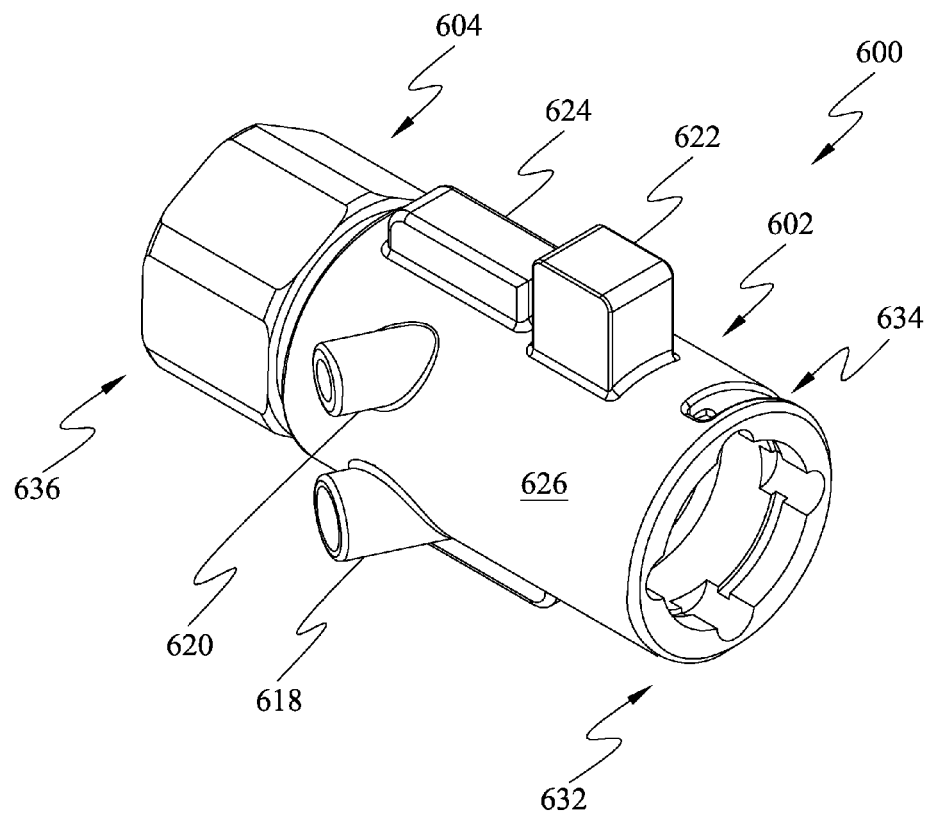
FIG. 6A is a perspective view of a carriage of the system for extracting hair follicles of FIG. 1A.

Referring to FIGS. 6A-6C, the system 110 may include a carriage 600. The carriage 600 may include two sub parts, namely a first part 602 and a second part 604. Alternatively, the carriage may be made as a single unit. The carriage 600 may have a longitudinal axis 606, and a bore 608 may be defined along the longitudinal axis 606. The bore 608 may define a first bearing engagement surface 610, a plurality of o-ring engagement surfaces 612, a retention ring engagement surface 614. The bore 608 may define a chamber 616 between the plurality of o-ring engagement surfaces 612, such that, the third portion 410 having the aperture 418 of the adapter 400 may be encompassed in the chamber 616. An outlet port 618 and a flush port 620 may be defined such that the outlet port 618 and the flush port 620 are in fluidic communication with the chamber 616. Each of the outlet port 618 and the flush port 620 may include a protrusion extending from an outer surface 626 of the carriage 600.

A first pillar 622 and a second pillar 624 may extend laterally from a cylindrical outer surface 626 of the carriage 600. The first pillar 622 and the second pillar 624 may be configured such that a gap 628 may be defined between the first pillar 622 and the second pillar 624. The first part 602 may have a proximal end 630 and a distal end 632. Near the distal end 632 of the first part 602, a slot 634 may be provided, which may extend from the outer surface 626 towards the bore 608.

The first part 602 may have an internally threaded surface 640 at the proximal end 630. The threaded configuration 640 may terminate before extending into the chamber 616. The second part 604 may include an external threaded surface 642 towards the distal end 638. The external surface of rest of the second part 604 may define a polygonal cross section.

When the first part 602 and the second part 604 are assembled, an annular groove 644 may be defined, which may receive an O-ring.

Referring to FIGS. 7A-7C, the system 110 may include a first connecting member 700. The first connecting member 700 may have a superior end 702, an inferior end 704, a distal end 706 and a proximal end 708.

The first connecting member 700 may include a cavity 710, a threaded hole 712, a first slot 714, a pair of second slots 716, a third slot 718 and a pair of pin holes 720.

The cavity 710 may be defined in the superior-inferior direction. The pair of second slots 716 may be through slots that are open towards the superior side, and may be disposed opposite to each other. The surface of the first connecting member 700 that may define the cavity, may also define the pair of second slots 716. A post 724 may extend from a portion of the first connecting member 700 that defines the cavity, in the inferior direction. The third slot 718 may be defined between the portion of the first connecting member 700 that defines the cavity 710 and a protrusion 728 extending in the inferior direction. The third slot 718 may be open on the inferior side and on one of the lateral sides. A portion of the first connecting member 700 disposed over the third slot 718 may define a threaded bore 712. The threaded bore 712 may extend from the proximal end 708 towards the distal end 706 such that an end of the bore 712 is exposed to the cavity 710. A portion of the first connecting member 700 disposed over the threaded bore 712 may include a pair of arms 726. The pair of arms 726 may be parallel to each other and may be spaced apart to define the first slot 714. The pair of arms 726 may extend in the superior direction. Each of the arms 726 may define a pin hole 720, such that the pin holes 720 defined in the arms 726 may oppose each other. The first connecting member 700 may form a part of a locking assembly.

Referring to FIGS. 8A-8C, the system 110 may include a stop 800, which may be received by the cavity 710 defined in the first connecting member 700. The stop 800 may have a proximal end 802, a distal end 804, a superior end 806 and an inferior end 808. A through hole 810 may be defined laterally extending across a longitudinal axis of the stop 800. A first slot 812 may be defined by a recessed surface disposed towards the proximal end 802. The first slot 812 may terminate before it reaches the hole 810, such that, a first supporting wall 814 may be formed. A cavity 816 may be defined from the inferior end 808 towards the superior end 806, and may terminate before reaching the through hole 810. The longitudinal axis of the cavity 816 may be perpendicular to the longitudinal axis of the through hole 810.

A portion of the stop 800 towards its superior side may include a first seat 818, a second seat 820 and a block wall 822. The first seat 818 and the second seat 820 may define a concave configuration, which may be configured to interface with a component defining a complimentary configuration. The second seat 820 and the first seat 818 may be generally horizontal, while the block wall 822 may be vertically disposed. The second seat 820, the block wall 822 and the first seat 818 may define a cascade configuration. The stop 800 may form a part of the locking assembly.

Referring to FIG. 9, the system 110 may include a first arm 900 that may be connected to the first member 200 through the first connecting member 700. The first arm 900 may have a proximal end 902, a distal end 904 and a longitudinal axis 906. The first arm 900 may be cylindrical shaft. A pair of slots 908 may be defined on either sides of the longitudinal axis 906, which may define a pair of adapting surfaces 910 on either sides of the longitudinal axis 906. A through hole 912 may be defined, having a longitudinal axis which may be perpendicular to the longitudinal axis 906. The through hole 912 may extend between the slots 908. The first arm 900 may have a threaded portion 914 towards its proximal end 902. The region near the distal end 904 of the first arm 900 may define a cylindrical shoulder 916. The cylindrical shoulder 916 may define an engaging surface 918. The engaging surface 918 may face the proximal end 902.

Referring to FIG. 10, the system 110 may include a second connecting member 1000 configured to connect the second member 300 with the second arm 1100. The second connecting member 1000 may include one or more handles 1002 and an arm 1004.

The arm 1004 may define a "C" shaped configuration. The arm 1004 may have an inner surface 1006 which may be recessed to define a groove 1008. The groove 1008 may be configured to receive a bearing.

The handle 1002 may be disposed towards the superior side of the second connecting member 1000. A through slot 1010 extending through opposing surfaces of the handle 1002 may be defined in the handle 1002. A plurality of holes 1012 may be defined in the handle 1002, such that the holes 1012 are exposed to the slot 1010.

Referring to FIGS. 11A-11C, the system 110 may include a second arm 1100 configured to be connected to the second member 300 using the second connecting member 1000. The second arm 1100 may be a cylindrical shaft having an external surface 1102, a proximal end 1104, a distal end 1106, a first post 1108, a second post 1110, a first bore 1112, a second bore 1114, a first aperture 1116 and a pair of second apertures 1118. The first post 1108 and the second post 1110 may extend laterally from the external surface 1102, in opposite directions. The first bore 1112 may extend from the distal end 1106 towards the proximal end 1104 along the longitudinal axis of the second arm 1100. The second bore 1114 may extend from the proximal end 1104 towards the distal end 1106 along the longitudinal axis of the second arm 1100 until it meets the first bore 1112. The second bore 1114 may have a diameter that may be smaller than the diameter of the first bore 1112. The difference in diameter of the first bore 1112 and the second 1114 may create a step 1120. The first aperture 1116 may be a through hole extending through the cylindrical external surface 1102 of the second arm 1100. The first aperture 1116 may be closer to the distal end 1106 as compared to the proximal end 1104.

The first post 1108 and the second post 1110 may be closer to the proximal end 1104 as compared to the distal end 1106. The first post 1108 may extend laterally in the superior direction, while the second post 1110 may extend laterally in the inferior direction. One or more second apertures 1118 may be defined in the second post 1110 to facilitate engagement with the second connecting member 1000.

At least a part of the external surface 1102 between the proximal end 1104 and the posts 1108, 1110 may be threaded 1122.

Referring to FIG. 12, an adjustment sleeve 1200 may be provided for engagement with the second arm 1100. The adjustment sleeve 1200 may be internally threaded 1202. The adjustment sleeve 1200 may be engaged with the second arm 1100 having threads. The adjustment sleeve 1200 may include a first set of apertures 1206 extending from the external surface of the adjustment sleeve 1200 towards the internal surface of the adjustment sleeve 1200. The apertures 1206 may be defined around the diameter of the adjustment sleeve 1200. The adjustment sleeve 1200 may include a second set of apertures 1204 extending from the external surface of the adjustment sleeve 1200 towards the internal surface of the adjustment sleeve 1200. The apertures 1204 may be defined around the diameter of the adjustment sleeve 1200. The first set of apertures 1206 may be offset along the longitudinal axis of the adjustment sleeve 1200, with respect to the second set of apertures 1204. The apertures 1204, 1206 may enable operating the adjustment sleeve 1200 to adjust the placement of the adjustment sleeve 1200 relative to the a second arm 1100. The adjustment sleeve 1200 may form a part of the locking assembly.

Figure 13A:
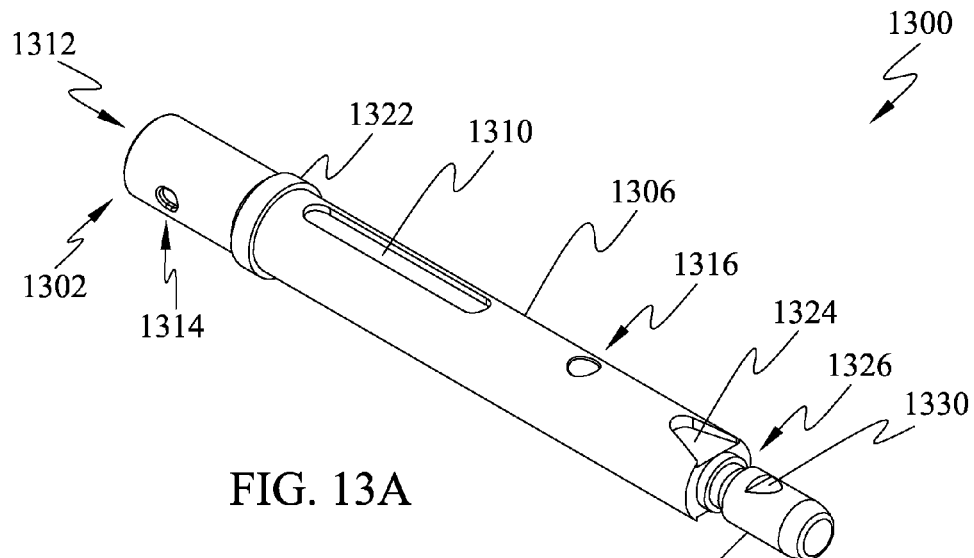
FIG. 13A is a perspective view of a stationary member of the system for extracting hair follicles of FIG. 1A.
Figure 13B:
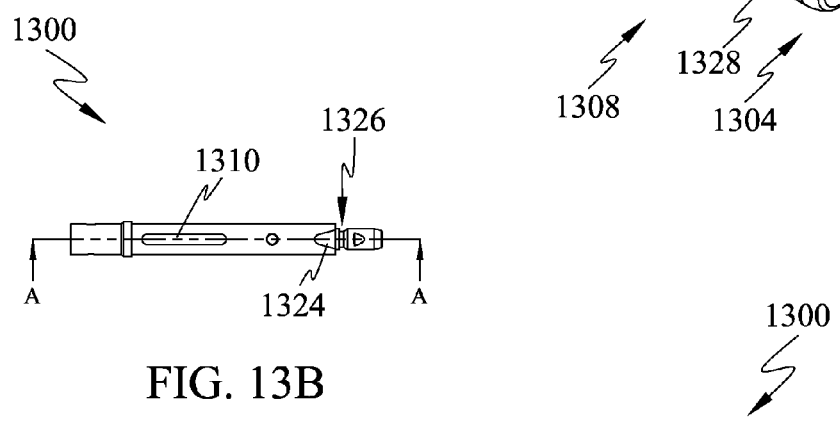
FIG. 13B is a top view of the stationary member of FIG. 13A.
Figure 13C:
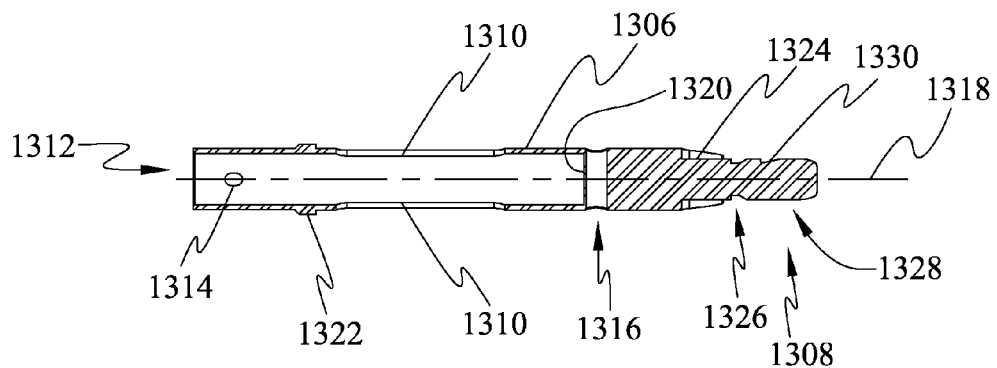
FIG. 13C is a sectional view about axis A-A of the stationary member of FIG. 13B.

Referring to FIGS. 13A-13C, a stationary arm 1300 may be configured to receive the second arm 1100. The stationary arm 1300 may be a cylindrical member having a proximal end 1302, a distal end 1304, an external surface 1306, an engagement feature 1308, a pair of slots 1310, a first bore 1312, a pair of opposing through holes 1314 and a second bore 1316. The first bore 1312 may extend from the proximal end 1302 towards the distal end 1304, along a longitudinal axis 1318 of the stationary arm 1300. The first bore 1312 may have an opening at the proximal end 1302 and may terminate before reaching the distal end 1304. The termination of the first aperture 1312 before reaching the distal end 1304 may result in the formation of a supporting wall 1320. The internal diameter of the first bore 1312 may be larger than the external diameter of the second arm 1100, thereby enabling the second arm 1100 to be received within the first bore 1312, and allowing the second arm 1100 to translate along the first bore 1312. The pair of slots 1310 may be defined to oppose each other, and may extend from the external surface 1306 into the first bore 1312. A flange 1322 may be defined on the external surface 1306, and may be provided between the slots 1310 and the proximal end 1302. The pair of opposing through holes 1314 may extend from the external surface 1306 into the first bore 1312. The pair of holes 1314 may be defined between the flange 1322 and the proximal end 1302. The second bore 1316 may be defined between the slots 1310 and the distal end 1304. The engagement feature 1308 may be provided towards the distal end 1304. The engagement feature 1308 may include a pair of recessed portions 1324, a neck portion 1326, a head portion 1328 and a second recessed portion 1330. The head portion 1328 may be a cylindrical shaped body provided towards the distal end 1304. The neck portion 1326 may be provided between a portion of the arm 1300 that defines the recess 1324 and the head portion 1328. The neck portion 1326 may have a diameter that is smaller than the diameter of the head portion 1328. The pair of recessed portions 1324 may be disposed on opposite sides of the external surface 1306. The recess 1324 may define a "V" or "U" shaped configuration. The second recessed portion 1330 may be defined on the cylindrical surface of the head portion 1328. The second recessed portion 1330 may be defined a "D" shaped configuration. The engagement feature 1308 may enable the stationary arm 1300 to be engaged with a component or system that may include a pair of paddles.

Figure 14:
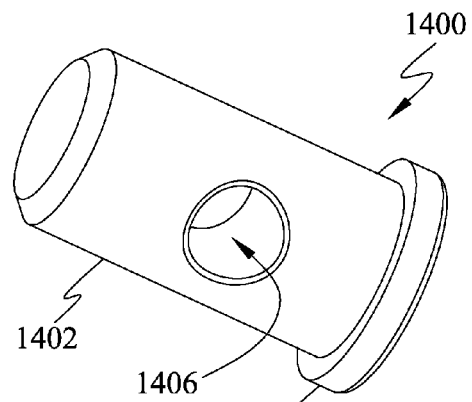
FIG. 14 is a perspective view of a second arm cap of the system for extracting hair follicles of FIG. 1A.

Referring to FIG. 14, the system 110 may include a second arm cap 1400. The second arm cap 1400 may be engaged with the second arm 1100. The second arm cap 1400 may include a shaft 1402 and a head 1404. A through hole 1406 may be defined in the shaft 1402. The through hole 1406 may be defined perpendicularly to the longitudinal axis of the shaft 1402. The head 1404 may have a diameter that is larger than the diameter of the first bore 1112 defined in the second arm 1100 at its distal end 1106. The shaft 1402 may be received into the second arm 1100 through an opening at it distal end 1106. The head 1404 may rest against or disposed outside the opening at the distal end 1106 of the second arm 1100.

Figure 15A:
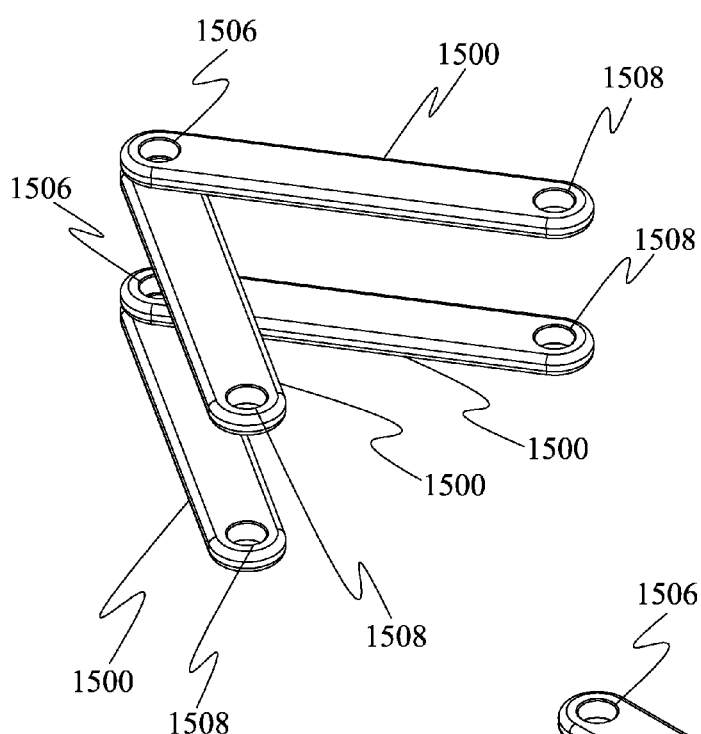
FIG. 15A is a perspective view of four paddle link members of the system for extracting hair follicles of FIG. 1A.
Figure 15B:
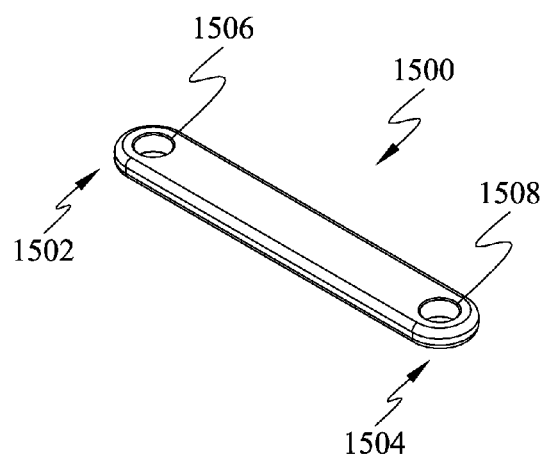
FIG. 15B is a perspective view of one of the four paddle link members of FIG. 15A.

Referring to FIG. 15, the system 110 may include two pairs of paddle link members 1500. The paddle link member 1500 may have a proximal end 1502 and a distal end 1504. The link member 1500 may define two through holes. A first through hole 1506 may be defined closer to the proximal end 1502, and may extend through two opposing surfaces of the link member 1500. A second through hole 1508 may be defined closer to the distal end 1504, and may extend through the two opposing surfaces of the link member 1500.

Figure 16A:
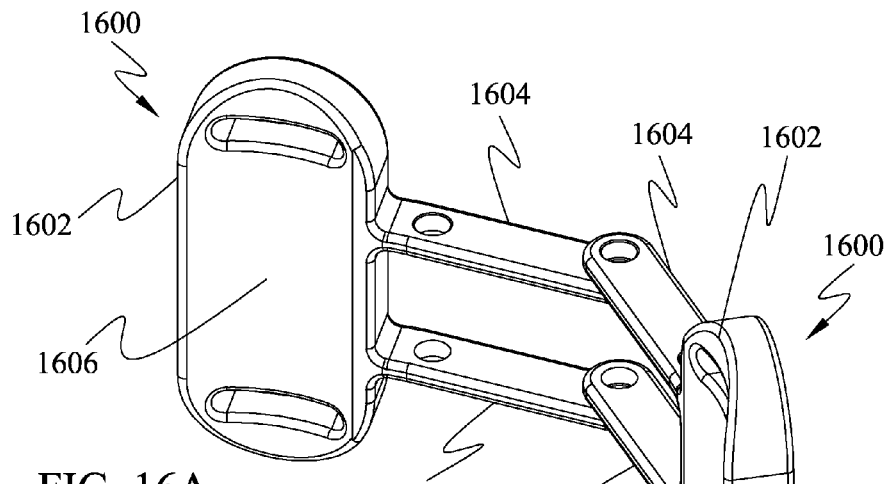
FIG. 16A is a perspective view of a pair of first paddle members of the system for extracting hair follicles of FIG. 1A.
Figure 16B:
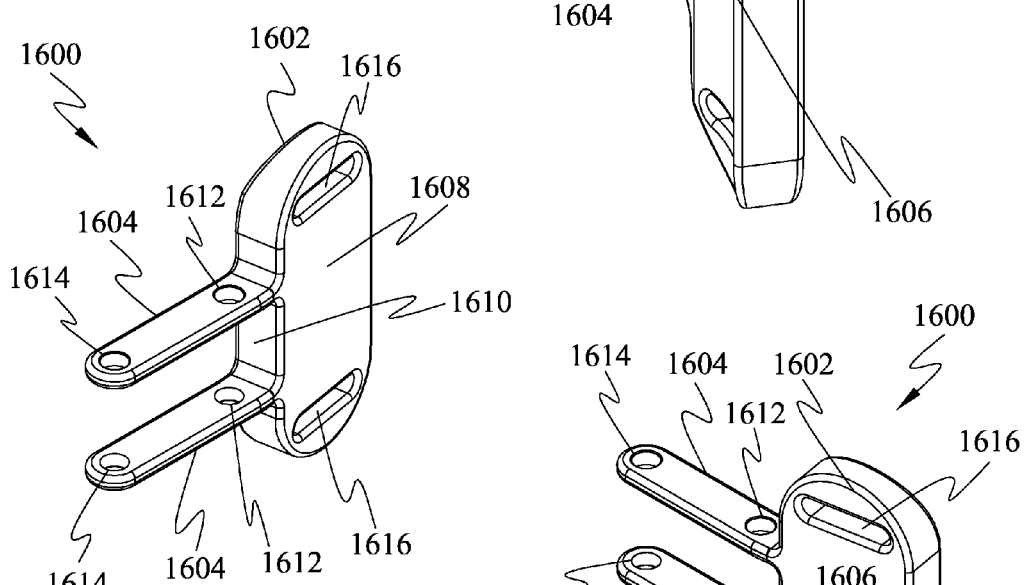
FIG. 16B is a perspective view of one of the pair of first paddle members of FIG. 16A.
Figure 16C:
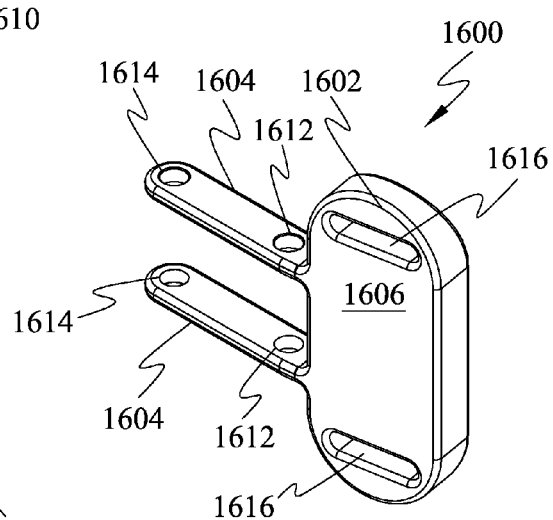
FIG. 16C is another perspective view of one of the pair of first paddle members of FIG. 16A.

Referring to FIGS. 16A-16C, the system 110 may include a pair of first paddle members 1600. The first paddle member 1600 may include a first paddle 1602 and a pair of link members 1604. The first paddle 1602 may be an oblong shaped body having a first surface 1606 and an opposing second surface 1608. A third surface 1610 may extend between the first surface 1606 and the second surface 1608. The first paddle 1602 may be designed to define a shape or topography that may facilitate a user to hold on to the paddles 1602, for example using four fingers (leaving the thumb) of each of his hands, and pull the paddles 1602 towards a pair of second paddles 1804 (illustrated in FIGS. 18A-18D). The first surface 1606 may define a concave curvature that may facilitate a user to hold on to the paddles 1602 and apply the desired force. The link members 1604 may extend from the third surface 1610 laterally on the same side of the third surface 1610. The paddle link members 1604 may be spaced apart. Each pair of link members 1604 may define two through holes. A first through hole 1612 may be defined closer to the intersection between the link member 1604 and the third surface 1610, and may extend through two opposing surfaces of the link member 1604. A second through hole 1614 may be defined closer to the free end of the link member 1604, and may extend through the two opposing surfaces of the link member 1604. Further one or more slots 1616 may be defined on the first surface 1606. The slots 1616 may be configured to facilitate better gripping of the first paddle 1602 by a user. The slots 1616 may receive one or more loops, straps, Velcro, levers, or other structure that may enable advancing and/or retracting (or even omnidirectional control, handling, or manipulation) of the paddles 1602. The slots 1616 may be substantially perpendicular to a longitudinal axis of the first paddle 1602. The slots 1616 may be in line with the direction in which the fingers are held while engaging the paddles 1602. The slots 1616 may extend through the first surface 1606 and the second surface 1608.

Figure 17:
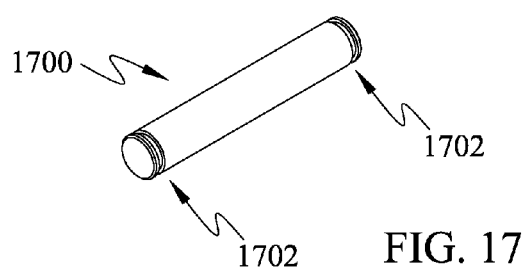
FIG. 17 is a perspective view of a link member pin of the system for extracting hair follicles of FIG. 1A.

Referring to FIG. 17, the system 110 may include multiple link member pins 1700. The link member pin 1700 may be received by through holes 1612, 1614 defined in the paddle link members. Each link member pin 1700 may define an annular groove 1702 closer to each of the ends of the link member pin 1700. Each of the grooves 1702 may be configured to receive a retaining ring, thereby ensuring that the pin 1700 is not disengaged from the link members 1500 and/or 1604.

Referring to FIGS. 18A-18D, the system 110 may include an external supporting member 1800. The external supporting member 1800 may include an arch portion 1802, a pair of second paddles 1804, an elongated housing 1806. The arch 1802 may define a first aperture 1808, a second aperture 1810, a third aperture 1812 and fourth aperture 1814. The first aperture 1808 may be configured to accommodate a counter pressure device 1900 (illustrated in FIGS. 19A-19B). The first aperture 1808 may be provided towards the inferior end 1816 of the external supporting member 1800. The second aperture 1810 may be provided above the first aperture 1808. The second aperture 1810 may be provided towards the superior end 1818 of the external supporting member 1800. The third aperture 1812 and the fourth 1814 may be provided adjacent to the first aperture 1808, and on either sides of the first aperture 1808. As a result of providing the first aperture 1808, the second aperture 1810, the third aperture 1812 and the fourth aperture 1814, a first inner surface 1820, a second inner surface 1822, a third inner surface 1824 and a fourth inner surface 1826, respectively, may be defined. A first threaded hole 1830 may be provided, extending from the first inner surface 1820 to the second inner surface 1822. A second threaded hole may extend from the first inner surface 1820 to the third inner surface 1824. A third threaded hole may be provided extending from the first inner surface 1820 to the fourth inner surface 1826.

A pair of second paddles 1804 may be connected to the arch 1802. Each of the second paddles 1804 may be disposed on either sides of the vertical axis of the arch 1802. The external supporting member 1800 may include an elongated housing 1806. The elongated housing 1806 may be provided between the two paddles 1804.

The second paddle 1804 may be a P-shaped body having a first surface 1840 and an opposing second surface 1842, which may face the first pair of paddle members 1600. The second paddles 1804 may be disposed such that they form a mirror image of each other. The paddle 1804 may be designed to define a shape or topography that may facilitate a user to hold on to the paddles 1804, for example using thumb of each of his hands, and pulling the paddles 1602 of first paddle members 1600 towards the second paddles 1804. The first surface 1840 may define a concave curvature 1844 towards the superior end 1818 of the paddle 10. The longitudinal axis of the concave curvature 1844 may be oblique to the longitudinal axis of the paddle 1804. The concave curvature 1844 may facilitate pressing of the user's thumb against the surface that defines the concave curvature 1844. The length of the concave curvature 1844 may be such that a major portion of the thumb may be supported. The concave curvature 1844 on the first surface 1840 may define a surface having a suitable length, curvature and angle of inclination, to compliment the shape and length of the thumb, and the angle at which the user holds and presses the thumb against the paddle 1804.

The second aperture 1810 may extend from the arch 1802 into and through the elongated housing 1806. Near the proximal end 1846 of the second aperture 1810 an annular slot 1848 may be defined. Near the proximal end of the elongated housing 1806 a pair of protrusions 1850 may be provided. The protrusions 1850 may be in the form of "V" or "U" shaped extensions, which may compliment the recessed portions 1324 provided in the stationary member 1300. On top of the elongated housing 1806, a protrusion 1838 may be provided, such that, it may be perpendicular to the longitudinal axis of the second aperture 1810. The protrusion 1838 may further define a threaded hole 1836 which may meet the second aperture 1810 in the elongated housing 1806.

Figure 19B:
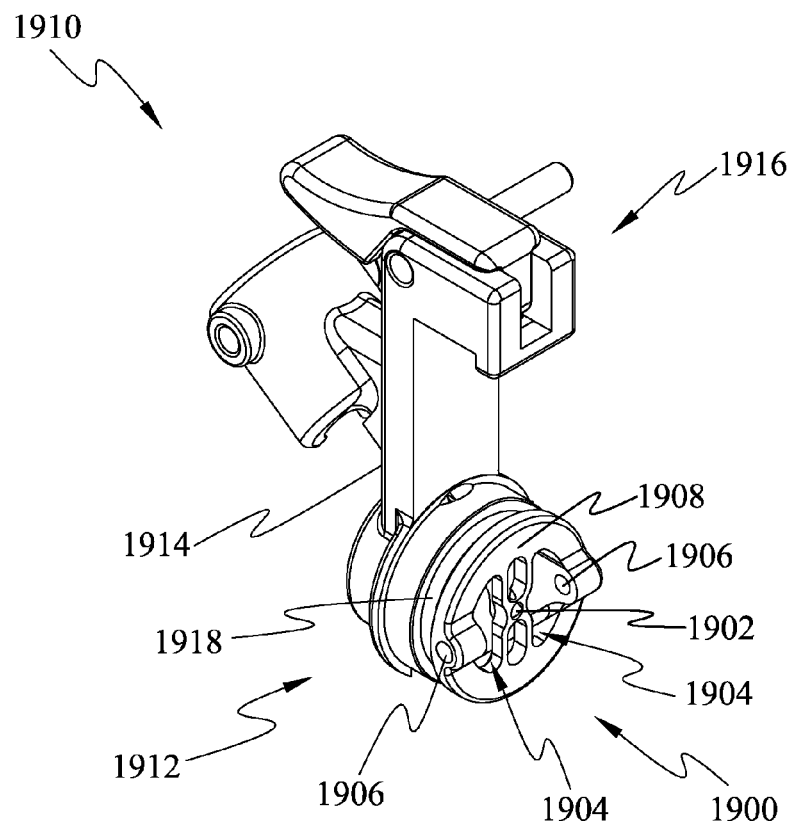
FIG. 19B is a perspective view of the counter pressure device of FIG. 19A.
Figure 19C:
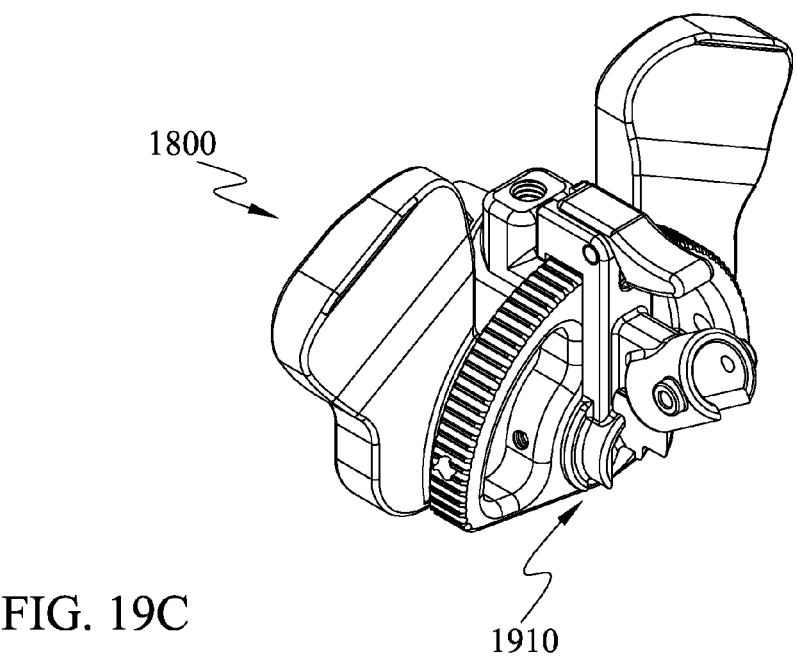
FIG. 19C is a perspective view of the counter pressure device of FIG. 19A engaged with the external supporting member of FIG. 18A.

The external supporting member 1800 may include a counter pressure device 1900. The counter pressure device 1900 may be engaged with the external supporting member 1800 such that a surface of the external supporting member 1800 interfaces with and presses against the external surface of the skin, while in use. Referring to FIGS. 19A-19C, the counter pressure device 1900 may be a circular plate with a targeting aperture 1902, which may be defined at the center of the plate. The counter pressure device 1900 may further define piercing member accommodation opening 1904 defined on both sides of the targeting aperture 1902. The piercing members may translate to-and-fro through the piercing member accommodation opening 1904. Further, the piercing member accommodation opening 1904 may define an oblong shape so that the piercing members may pivot while the piercing members have extended through the piercing member accommodation opening 1904 (counter pressure device 1900).

The counter pressure device 1900 may define a pair of pivot holes 1906. The longitudinal axis of the pivot holes 1906 may be perpendicular to the longitudinal axis of the targeting aperture 1902. The pivot holes 1906 may be defined such that a surface 1908 of the counter pressure device 1900 that interfaces with the skin is flush, without protrusions.

The counter pressure device 1900 may apply pressure to, over or around the tissue comprising hair follicle when it is held against the external surface of the skin.

The counter pressure device 1900 may be connected or engaged or integral to an arm 1910. The arm 1910 and the counter pressure device 1900 may be engaged with the external supporting member 1800. The arm 1910 may include a cylindrical body 1912, a pillar 1914 and an extending member 1916. The arm 1910 may be configured to be operable to at least partially rotate about an axis of the external supporting member 1800.

The cylindrical body 1912 may include a groove 1918 on its external surface, such that the groove 1918 aligns with the holes defined the external supporting member 1800, when assembled. The arm 1910 may be engaged with the external supporting member 1800 by means of engagement screws which may be passed through the holes defined in the external supporting member 1800, such that a part of the engagement screws are received by the groove 1918.

Figure 20:
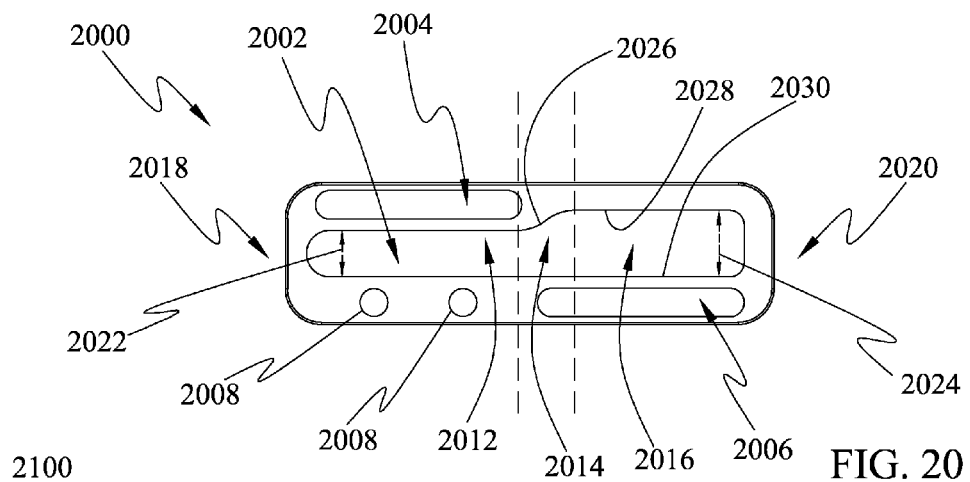
FIG. 20 is a perspective view of a guide plate of the system for extracting hair follicles of FIG. 1A.

Referring to FIG. 20, the system 110 may include a guide plate 2000. The guide plate 2000 may be rectangular in shape whose corners may be filleted. The guide plate 2000 may include a first slot 2002, a second slot 2004, a third slot 2006 and a plurality of holes 2008.

The first slot 2002, second slot 2004 and third slot 2006 may be through slots. The first slot 2002 may be defined between the second slot 2004 and the third slot 2006. The second slot 2004 may be defined near the proximal superior side of the guide plate 2000, while the third slot may be defined near the distal inferior side of the guide plate 2000. The second slot 2004 and the third slot 2006 may have uniform width and length. The plurality of holes 2008 may be defined opposite to the second slot 2004, and may be on the same side of the third slot 2006.

The first slot 2002 may define a first region 2012, a second region 2014 and a third region 2016. The first region 2012 may be close to a proximal end 2018 of the guide plate 2000. The third region 2016 may be close to a distal end 2020 of the guide plate 2000. The second region 2014 may be intermediate the first region 2012 and the third region 2016. The first region 2012 may have the first width 2022, and the third region 2016 may have a third width 2024. The first width 2022 may be smaller than the third width 2024. The second region 2014 may have a width that is same as the first width 2022 at first end, and a width that is same as the third width 2024 at the opposite second end. The width of the second region 2014 may gradually change from first width 2022 to third width 2024. The gradual change in width in the second region 2014 may define a curved surface 2026. The curved surface 2026 may be defined in the superior edge 2028 of the first slot 2002, whereas the inferior edge 2030 of the slot 2002 may define a straight line.

Figure 21A:
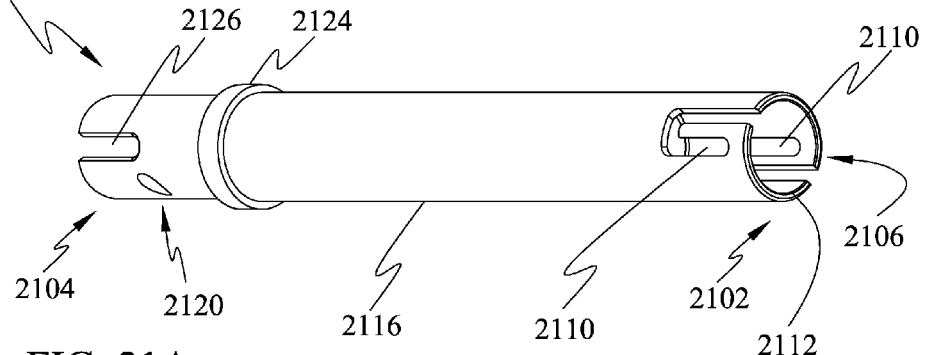
FIG. 21A is a perspective view of a cover member of the system for extracting hair follicles of FIG. 1A.
Figure 21B:
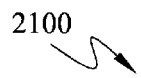
FIG. 21B is a top view of the cover member of FIG. 21A.
Figure 21C:
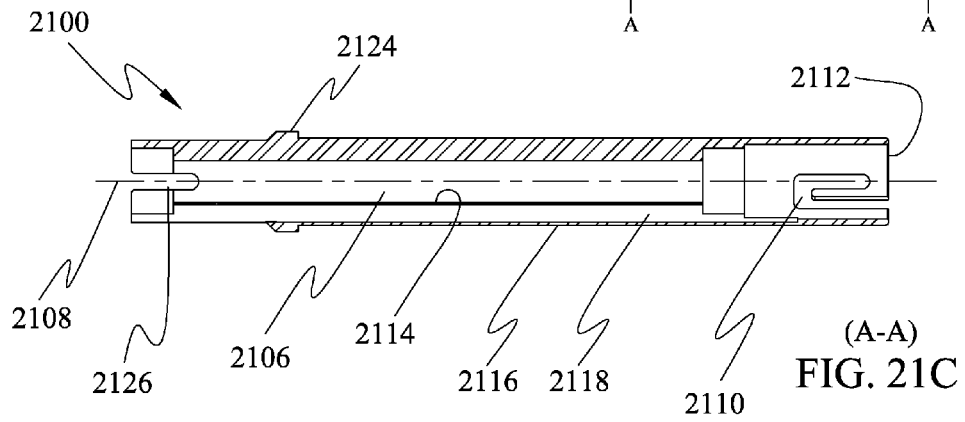
FIG. 21C is a sectional view about axis A-A of the cover member of FIG. 21B.

Referring to FIGS. 21A-21C, the system 110 may include a cover member 2100. The cover member 2100 may be configured to receive the first member 200 and the second member 300. The cover member 2100 may be a cylindrical tube having a proximal end 2104 and a distal end 2102. The cover member 2100 may define a bore 2106 along its longitudinal axis 2108, extending from the proximal end 2104 to the distal end 2102. The distal end 2102 of the cover member 2100 may include a U shaped slot 2110 defined on its cylindrical body. The slot 2110 may extend from the edge 2112 at the distal end 2102 of the cover member 2100 along the longitudinal axis 2108 of the cover member 2100 and thereafter turn towards the distal end 2102 of the cover member 2100 and terminate before reaching the edge 2112 at the distal end 2102, thereby defining the "U" shape. The cover member 2100 may have a pair of such slots 2110 defined on diametrically opposing sides of the cylindrical body.

The cover member 2100 may have an inner surface 2114 and an outer surface 2116. A channel 2118 may be defined between the inner surface 2114 and the outer surface 2116 such that fluid may be passed through the channel 2118. The channel 2118 may be defined between the proximal end 2104 and the distal end 2102. The channel 2118 may extend from the proximal end 2104 until the distal end 2102. An aperture 2120 may be defined in the cover member 2100. The aperture 2120 may extend from the outer surface 2116 into the channel 2118. The fluid may be passed into the channel 2118 through the aperture 2120. The aperture 2120 may be defined closer to the proximal end 2104 than the distal end 2102.

The inner surface 2114 of the cover member 2100 may define a stepped configuration, such that bushing may be accommodated in the stepped configuration. The bushing may define a channel that may be in fluidic communication with the channel 2118.

A flange 2124 may be defined on the outer surface 2116 closer to the proximal end 2104. A pair of opposing slots 2126 may be defined by the cover member 2100. Each of the slots 2126 may be defined on diametrically opposing sides of the cover member 2100. Each slot 2126 may start from the edge of the cover member 2100 at the proximal end 2104 and may terminate before reaching the flange 2124.

Figure 22A:
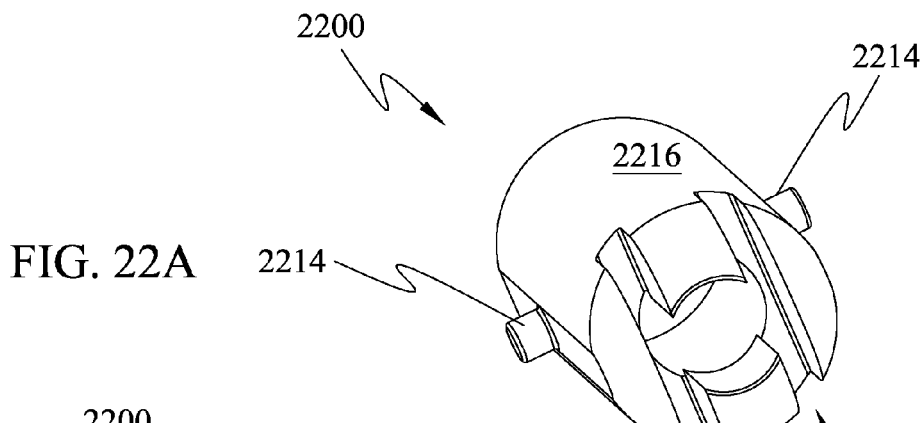
FIG. 22A is a perspective view of a tissue stabilizing member of the system for extracting hair follicles of FIG. 1A.
Figure 22B:
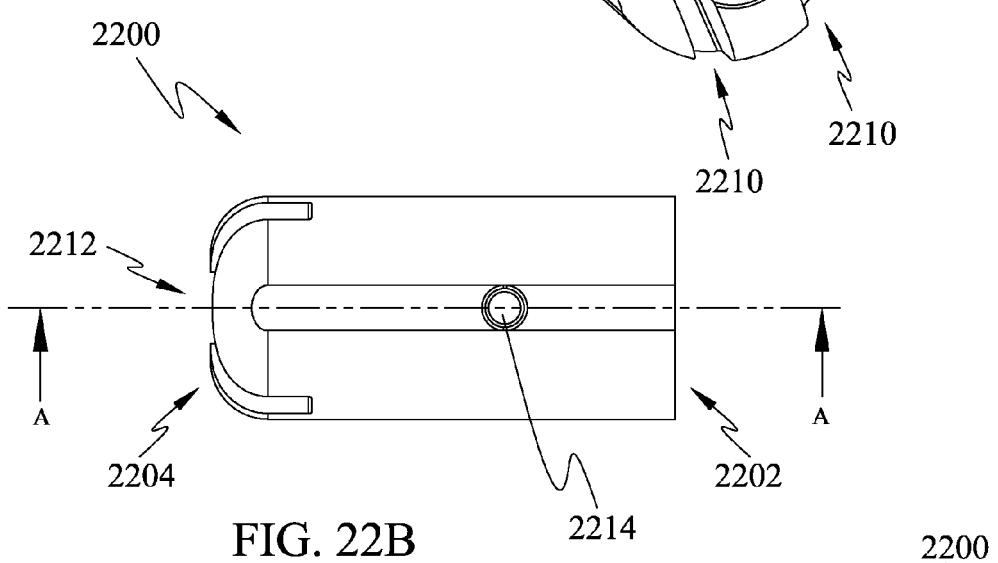
FIG. 22B is a side view of the tissue stabilizing member of FIG. 22A.
Figure 22C:
FIG. 22C is a sectional view about axis A-A of the tissue stabilizing member of FIG. 22B.

Referring to FIGS. 22A-22C, the system 110 may include a tissue stabilizing member 2200. The tissue stabilizing member 2200 may be moved below the external surface of the skin. The tissue stabilizing member 2200 may translate parallel to the longitudinal axis of the first member 200 or the longitudinal axis of a cover member 2100. The tissue stabilizing member 2200 may apply pressure at least around the tissue disposed between the tissue stabilizing member 2200 and the counter pressure device 1900. The tissue stabilizing member 2200 may be engaged with the cover member 2100.

The tissue stabilizing member 2200 may define a substantially cylindrical shape. The tissue stabilizing member 2200 may have a proximal end 2202 and a distal end 2204. The tissue stabilizing member 2200 may define a bore 2206 extending from the proximal end 2202 until the distal end 2204. A flange 2208 may be defined on an inner surface of the tissue stabilizing member 2200, such that the inside diameter of tissue stabilizing member 2200 at the flange and beyond is smaller than the inside diameter of the tissue stabilizing member 2200 at the proximal end 2202. The bore 2206 defined between the proximal end 2202 and the flange 2208 may be configured to receive a compression member, such as a spring. The compression member may press against the flange 2208 when the tissue stabilizing member is pushed in to the cover member 2100. A pair of slots 2210 may be defined on a face 2212 of the tissue stabilizing member 2200. The pair of slots 2210 may enable piercing members, which may have pierced into a tissue through an external surface of the skin, to pivot, even if the piercing members have pierced beyond the distal end of the tissue stabilizing member 2200. The tissue stabilizing member 2200 may include a pair of pins 2214 laterally extending from an outer surface 2216 of the tissue stabilizing member 2200 in opposing directions. The pins 2214 may be received in the "U" shaped slots 2110 defined in the cover member 2100, thereby enabling the tissue stabilizing member 2200 to translate parallel to the longitudinal axis of the first member 200 or the longitudinal axis of the cover member 2100.

Referring to FIGS. 23A-23C, a housing assembly 2300 may be provided. The housing assembly 2300 may include a first component 2302 and a second component 2304. The first component 2302 may include a first portion 2306 and a second portion 2308. The second portion 2308 may be disposed above the first portion 2306. The second component 2304 may include a third portion 2310 and a fourth portion 2312. The fourth portion 2312 may be disposed above the third portion 2310. The first component 2302 and the second component 2304 may be assembled such that the first portion 2306 comes in contact with the third portion 2310, and the second portion 2308 coming in contact with the fourth portion 2312. The housing assembly 2300 may include a proximal end 2314 and a distal end 2316. The housing assembly 2300 may define a first bore 2318 extending from the proximal end 2314 until the distal end 2316, in the region of the first portion 2306 and the third portion 2310. A second bore 2320 may be defined, which may extend through the second portion 2308 and the fourth portion 2312. The bore 2318 may be parallel to the second bore 2320. A hollow region may be defined in between the first bore 2318 and the second bore 2320 extending longitudinally. A first slot 2324 may be defined, such that the first slot 2324 extends longitudinally from the edge of the first bore 2318 at the distal end 2316. The first slot 2324 may extend from an outer surface of the first portion 2306 into the first bore 2318. An outer surface of the first portion 2306 from where the first bore 2318 begins at the distal end 2316 defines an externally threaded portion 2326. An outer surface of the second portion 2308 from where the second bore 2320 begins at the distal end 2316 may define an externally threaded portion 2328. A second slot 2330 may be defined at the superior end of the housing assembly 2300 in the region of second portion 2308 and the fourth portion 2312, such that, the second slot 2330 may extend until it reaches the second through hole 2320. A third slot 2332 may be defined at the inferior end of the housing assembly 2300 in the region of the first portion 2306 and the third portion 2310, such that, the third slot 2332 may be extended until it reaches the first bore 2318. A pair of fourth slots 2334 may be defined on lateral sides of the housing assembly 2300. One of the fourth through slot 2334 may be defined in the second portion 2308, and the other fourth through slot 2334 may be defined in the fourth portion 2312. The fourth slots 2334 may oppose each other, and may be exposed to the hollow region of the housing assembly 2300. The first bore 2318 may include several sections that may vary in dimension and diameter along its length. Similarly, the second bore 2320 may include several sections that may vary in dimension and diameter along its length. A protrusion 2336 may be provided on top of the first component 2302 near the distal end 2316, which may define a threaded hole 2338. Plurality of engagement holes may be provided in housing assembly 2300 to facilitate assembly of at least the first component 2302, the second component 2304 and various other components received in the housing assembly 2300. A fifth through slot 2342 and a sixth through slot 2344 may be defined in the third portion 2310. The first slot 2324, the fifth slot 2342 and the sixth slot 2344 may enable translatory movement of various ports that may be used to establish a fluid pathway in the system 110. A seventh slot 2346 may be provided at the superior side of the housing assembly 2300. The seventh slot 2346 may be defined across the second slot 2330. The seventh slot 2346 may facilitate adjustment of position of the adjustment sleeve 1200 with respect to the second arm 1100.

Now reference may be made to FIGS. 24A-24G. The first member 200 may be engaged with the adapter 400. The threaded surface or threaded portion 230 is engaged with the internal thread provided in the adapter 400. Rotation of the adapter 400 may result in rotation of the first member 200. The translatory movement of the first member 200 may result in translatory movement of the adapter 400.

The adapter 400 may be engaged with the power shaft 500. The first portion 506 of the power shaft 500, which may have a polygonal cross section may be received in the bore 422 defined in the adapter 400. At least a portion of the bore 422 may have a polygonal cross section. The first portion 506 may translate along the bore 422. Rotation of the power shaft 500 may result in rotation of the adapter 400. The second portion 508 of the power shaft 500 may engage with a power tool 2404. The second portion 408 of the adapter 400 may engage with a bearing 2402.

The first part 602 of the carriage 600 may be threadably engaged with the second part 604 of the carriage 600. The assembly of first part 602 and the second part 604 may be referred to as carriage 600. The carriage 600 may house the adapter 400 and a portion of the power shaft 500. The bearing 2402 may be received in the bearing engagement groove 610. O-rings 2406 may be received in the O-ring engagement grooves 612. Another O-ring 2408 may be received in the annular groove 644 defined between the first part 602 and the second part 604. A retention ring 2410 may be received in the retention ring engagement groove 614.

The first connecting member 700 may be accommodated on the carriage 600. The protrusion 728 is received in the gap 628 of the carriage 600. The third slot 718 receives the first pillar 622 of the carriage 600. The post 724 may be received by the slot 634 of the carriage 600. Such an engagement of the first connecting member 700 with the carriage 600 may prevent relative translatory motion.

A spring 2412 may be received in the cavity 710 of the first connecting member 700. The stop 800 may be placed over the spring 2412, such that the spring 2412 is also received by the cavity 816 defined in the stop. This may be part of the locking assembly.

A threaded screw 2414 may engage with the threaded hole 712 of the first connecting member 700. An end of the screw 2414 may interface with the first supporting wall 814 of the stop 800. The first slot 714 of the first connecting member 700 may receive the adapting surface 910 of the first arm 900. A pin 2416 may be received through the through hole 912 provided in the first arm 900 and pin holes 720 provided in the first connecting member 700. The pin 2416 may facilitate engagement of the first arm 900 with the first connecting member 700. A pin 2418 may be received in the through hole 810 of the stop 800, such that the pin 2418 may translate along the first slot 2002 of the guide plates 2000.

A threaded adjustment knob 2420 may be engaged with the first arm 900 at its threaded portion 914. The threaded adjustment knob 2420 may be a depth limiting means for configuring a distance between the distal end of the channel created in the tissue by the first member 200 and the external surface 10 of the skin 11.

The first member 200 may be received by or engaged to the second member 300. A portion of the first member 200 is received inside the second bore 332 defined in the second member 300. The arms 318 of the second member 300 may rest over the slots 220 provided in the first member 200. The protrusions 328 provided in the arms 318 may interface with the surface of the slot 220. The engagement protrusions 312 of the second member 300 may be received in the slots 234 of the first member 200. A bearing 2422 may receive the annular protrusion 316 of the second member 300. The bearing 2422 may adapted with the second connecting member 1000. The bearing 2422 may be received in the groove 1008 defined in the second connecting member 1000.

The second connecting member 1000 may be engaged with the second arm 1100. The through slot 1010 of the second connecting member 1000 may receive the second post 1110 of the second arm 1100. Pins 2424 may be passed through the second apertures 1118 of the second arm 1100 and holes 1012 of the second connecting member 1000.

The adjustment sleeve 1200 may be engaged with the second arm 1100. The adjustment sleeve 1200 may be engaged with the threaded portion 1122 of the second arm 1100.

A portion of the first arm 900 may be accommodated in the first bore 1112 and the second bore 1114 of the second arm 1100. The cylindrical shoulder 916 of the first arm 900 may be accommodated in the first bore 1112 and the proximal end 902 of the first arm 900 may extend out of the second bore 1114 of the second arm 1100. The proximal end 902 of the first arm 900 may even extend out of the proximal end 2314 of the second bore 2320 of the housing 2300.

The second arm cap 1400 may be engaged with the second arm 1100. The shaft 1402 of the second arm cap 1400 may be configured to be adapted in the first bore 1112 of the second arm 1100, such that, the head 1404 of the second arm cap 1400 may fit flush with the edge of the second arm 1100 at the distal end 1106 of the second arm 1100.

A clipping spring 2426 or a first compressible means may be accommodated in the first bore 1112 of the second arm 1100 such that, the clipping spring 2426 may be disposed between the step 1120 or intersection of the first bore 1112 and second bore 1114 of the second arm 1100 and the engaging surface 918 of the cylindrical shoulder 916 of the first arm 900. The clipping spring 2426 may enclose a portion of the cylindrical shaft of the first arm 900.

A portion of the second arm 1100 may be received by the stationary arm 1300. The first aperture 1312 of the stationary arm 1300 may accommodate at least a part of the cylindrical portion of the second arm 1100. The link member pin 1700 may be received by the pair of slots 1310 of the stationary arm 1300. The link member pin 1700 may pass through the through hole 1406 of the second arm cap 1400. Another link member pin 1700 may be received by the second aperture 1316 of the stationary arm 1300. A spring 2428 or second compressible means may be accommodated in the first bore 1312 of the stationary arm 1300 such that the spring 2428 may be disposed between the head 1404 of the second arm cap 1400 and the supporting wall 1320 of the stationary arm 1300.

The stationary arm 1300 may be engaged with the external supporting member 1800. The head portion 1328 of the stationary arm 1300 may be received by the elongated housing 1806. An elastic ring 2430 or garter spring or canted coil spring (such as a Bal Seal Canted Coil Spring®) may be received in the annular slot 1848 of the elongated housing 1806, such that the engage elastic ring 2430 surround the neck portion 1326 of the engagement feature 1308 of the stationary arm 1300. A screw 2432 may be received by the threaded hole 1836 of the external supporting member 1800, and a tip of the screw 2432 may interface with the second recess portion 1330 of the stationary arm 1300, such that, the relative motion of the stationary arm 1300 may be prevented with respect to the external supporting member 1800. The counter pressure device 1900 may be engaged with the external supporting member 1800. The counter pressure device 1900 may be received in the first aperture 1808 defined in the external supporting member 1800.

The first paddles 1600 may be operatively engaged with stationary arm 1300 and the second arm 1100. Each of the first paddles 1600 may be disposed on laterally opposing sides of the stationary arm 1300. A link member pin 1700 may be passed through the second aperture 1316 of the stationary arm 1300. One end of the link member pin 1700 may pass through the second through holes 1614 of the link members 1604 disposed on the superior side of the first paddle members 1600. Another end of the link member pin 1700 may pass through the second through holes 1614 of the link members 1604 disposed on the inferior side of the first paddle members 1600.

Another link member pin 1700 may be received by the pair of slots 1310 of the stationary arm 1300. The link member pin 1700 may pass through the through hole 1406 of the second arm cap 1400. The link member 1700 may be engaged with four link members 1500. Two link members 1500 may be disposed on the superior side of the second arm 1100 and the remaining two link members 1500 may be disposed on the inferior side of the second arm 1100. Each of the two link members 1500 disposed on the superior side may be disposed on laterally opposing sides of the second arm 1100. Likewise, each of the two link members 1500 disposed on the inferior side may be disposed on laterally opposing sides of the second arm 1100. One end of the link member pin 1700 may pass through the first through holes 1506 of the link members 1500 disposed on the superior side. Another end of the link member pin 1700 may pass through the first through holes 1506 of the link members 1500 disposed on the inferior side.

Another link member pin 1700 may engage with link members 1500 and the first paddle member 1600 disposed on one of the lateral sides of the stationary arm 1300 or the second arm 1100. One end of the link member pin 1700 may pass through the second through hole 1508 of the link member 1500 disposed on the superior side and first through hole 1612 provided in link member 1604 disposed on the superior side. Another end of the link member pin 1700 may pass through the second through hole 1508 of the link member 1500 disposed on the inferior side and first through hole 1612 provided in the link member 1604 disposed on the inferior side.

Another link member pin 1700 may engage with link members 1500 and the first paddle 1600 disposed on another lateral side of the stationary arm 1300 or the second arm 1100. One end of the link member pin 1700 may pass through the second through hole 1508 of the link member 1500 disposed on the superior side and first through hole 1612 provided in link member 1604 disposed on the superior side. Another end of the link member pin 1700 may pass through the second through hole 1508 of the link member 1500 disposed on the inferior side and first through hole 1612 provided in the link member 1604 disposed on the inferior side. Each of the four link member pins 1700 may receive retention rings in the annular grooves 1702.

The cover member 2100 may receive the first member 200 and the second member 300. The first member 200 and the second member 300 may pass through the bore 2106 of the cover member 2100.

The cover member 2100 may be engaged with the tissue stabilizing member 2200. At least a part of the tissue stabilizing member 2200 may be received by the cover member near the distal end 2102 of the cover member 2100. The pair of pins 2214 may be received in the "U" shaped slot 2110, such that the tissue stabilizing member 2200 may translate in a portion of the "U" shaped slot 2110 that is closed at the distal end 2102. A spring 2434 may be accommodated in the bore 2206 of the tissue stabilizing member 2200. The spring 2434 may be disposed between the flange 2208 of the tissue stabilizing member 2200 and an inwards projecting step or bushing 2436 provided in the cover member 2100.

The bushing 2436 may be received by a stepped inner portion towards the distal end 2102 of the cover member 2100. Another bushing 2436 may be received by another stepped inner portion towards the proximal end 2104 of the cover member 2100.

The first component 2302 and the second component 2304 of the housing 2300 may be engaged such that, outlet port 618 and the flush port 620 may translate in the sixth through slot 2344 and fifth through slot 2342, respectively. The first post 1108 of the second arm 1100 may translate in the second slot 2330 of the housing assembly 2300. A tube 2438 engaged with the aperture 2120 of the cover member 2100 may be retained in the first slot 2324.

The guide plates 2000 may be engaged over the outer surface of the housing assembly 2300 such that, the guide plate 2000 may cover a portion of the fourth slot 2334, such that the pin 2418 received in the through hole 810 of the stop 800 may translate in the first slot 2002 of the guide plates 2000.

A nut 2440 may be engaged with the externally threaded portion 2328 of the housing assembly 2300. The flange 1322 of the stationary arm 1300 may be pressed against the edge of the threaded portion 2328 by the nut 2400, and may prevent the stationary arm 1300 from disengaging from the housing assembly 2300.

Another nut 2442 may be engaged with the externally threaded portion 2326 of the housing assembly 2300. The flange 2124 of the cover member 2100 may be pressed against the edge of the threaded portion 2326 by the nut 2400, and may prevent the cover member 2100 from disengaging from the housing assembly 2300.

A screw 2444 or motion limiting means may be received by the protrusion 2336 of the housing assembly 2300. The screw 2444 may be received in the threaded hole 2338 defined in the protrusion 2336.

Referring to the figures, and more specifically to FIGS. 1A-1E and FIGS. 24F-24Z1, in order to extract a hair follicle, a portion 112 of the system 110 may be moved underneath the skin 10. The portion 112 may include the cover member 2100, the first member 200, the second member 300 and the tissue stabilizing member 2200. At least a part of the portion 112 may be disposed between an inner surface 12 of the skin 10 and the skull 15. The tissue stabilizing member 2200 may be positioned around the tissue that has the target hair follicle 13,14. The tissue stabilizing member 2200 may press against the inner surface 12 of the skin 10, around the tissue that has to hair follicle 13. The counter pressure device 1900 may be disposed opposite to the tissue stabilizing member 2200, and may interface with the external surface 11 of the skin 10. A part of the hair 14 may extend out of the external surface 11. The aperture or opening 1902 provided in the counter pressure device may enable a user to see the hair follicle that is being targeted for extraction. The alignment of the hair follicle 13 may be altered, for example, using piercing members, to align the hair follicle 13 with the longitudinal axis of the first member 200, to avoid transection of hair follicle 13 while it is being extracted.

In order to extract the hair follicle 13 from underneath the skin 10, the first member 200 may have to be rotated about its longitudinal axis while it is translated into the skin 10. The rotation of the first member 200 may be enabled by the power tool 2404. The power tool 2404 imparts torque to the power shaft 500, thereby enabling the power shaft 500 to rotate. The power shaft 500 transfers the torque to the adapter 400, thereby enabling the adapter 400 to rotate. The power shaft 500 may transfer the torque to the adapter 400 even if the adapter moves linearly with respect to the power shaft 500, owing to the configuration of the power shaft 500 and the adapter 400. The adapter 400 transfers the torque to the first member 200, thereby enabling the first member 200 to rotate. Rotation of the first member 200 may result in rotation of the second member 300, owing to engagement between the first member 200 and the second member 300, in which the engagement protrusions 312 of the second member 300 may be received in the slots 234 of the first member 200.

As recited earlier, the first member 200 may have to be translated into the skin from underneath the skin to enable extraction of the hair follicle. In addition to translation of the first member 200, the second member 300 may have to be translated along the axis of the second member 300 or the first member 200 to enabling clipping of tissue that may have been cut by the first member 200.

An operator may insert a portion 112 of the system 110 underneath the skin 10. The extent to which the portion 112 may be inserted may be limited by the nut 2442. The rest of the system 110 and the system 100, which include the counter pressure device 1900 may be exposed to the external surface 11 of the skin. The tissue stabilizing member 2200 may first enter the incision 120, followed by the other parts. The portion 112 is moved underneath the skin 11 such that the tissue stabilizing member 2200 presses around the tissue that has the target hair follicle, from underneath the skin 11, while the counter pressure device 1900 presses the tissue that has the hair follicle from the external surface 11 of the skin, such that the target hair follicle may be disposed between the tissue stabilizing member 2200 and the counter pressure device 1900. It may be noted that, the extent to which the tissue stabilizing member 2200 extends out of the cover member 2100 owing to the tension applied by the spring 2434 over the tissue stabilizing member 2200 may depend on the thickness of the skin 10. The hair follicle that may be disposed between the tissue stabilizing member 2200 and the counter pressure device 1900 may be aligned with the longitudinal axis of the first member 200 before the operator initiates translatory movement of the first member 200. Once, aligned, the operator may initiate the translatory movement of the first member.

Figure 24A:
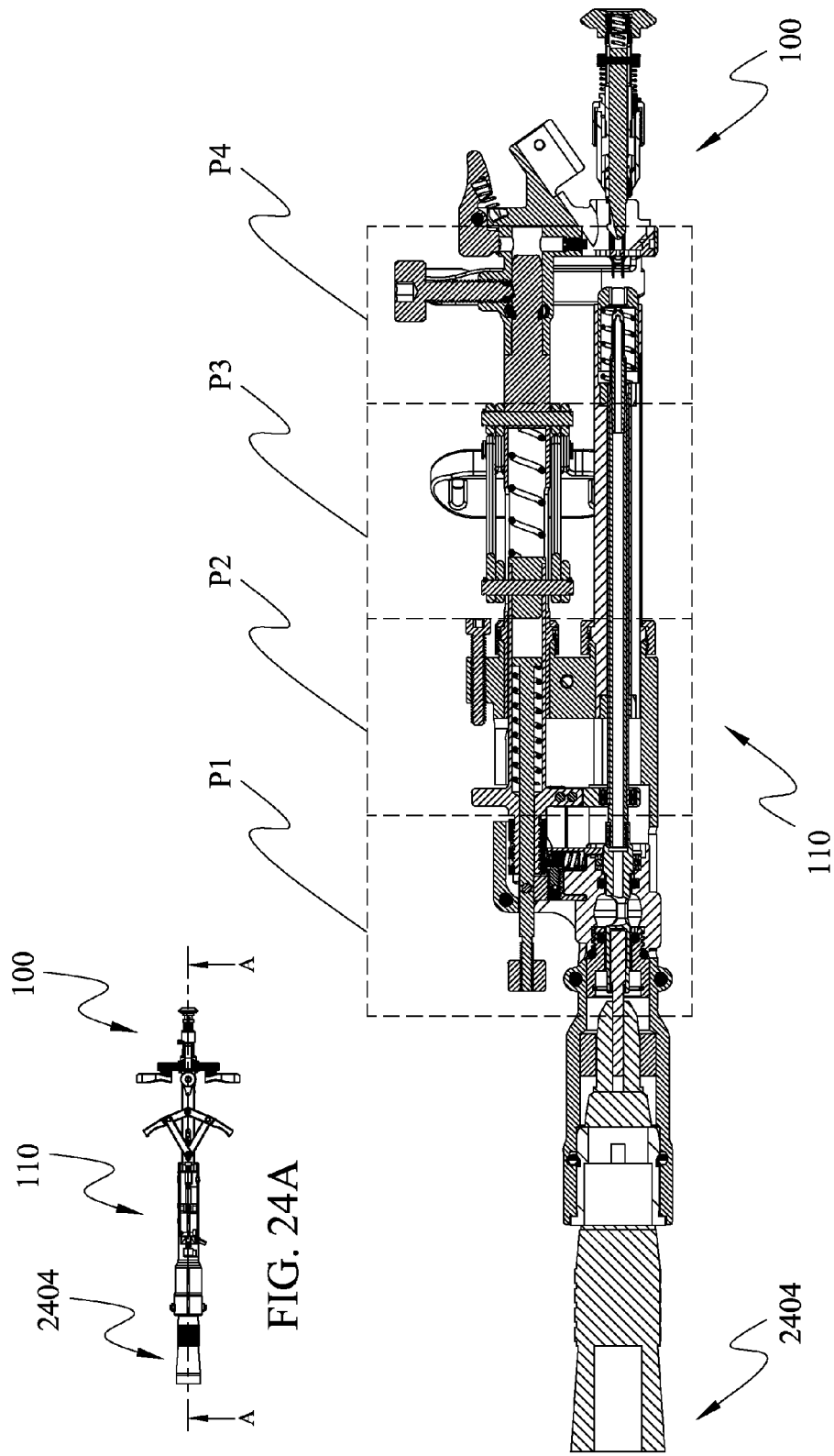
FIG. 24A is a top view of the systems of FIG. 1A.
Figure 24D:
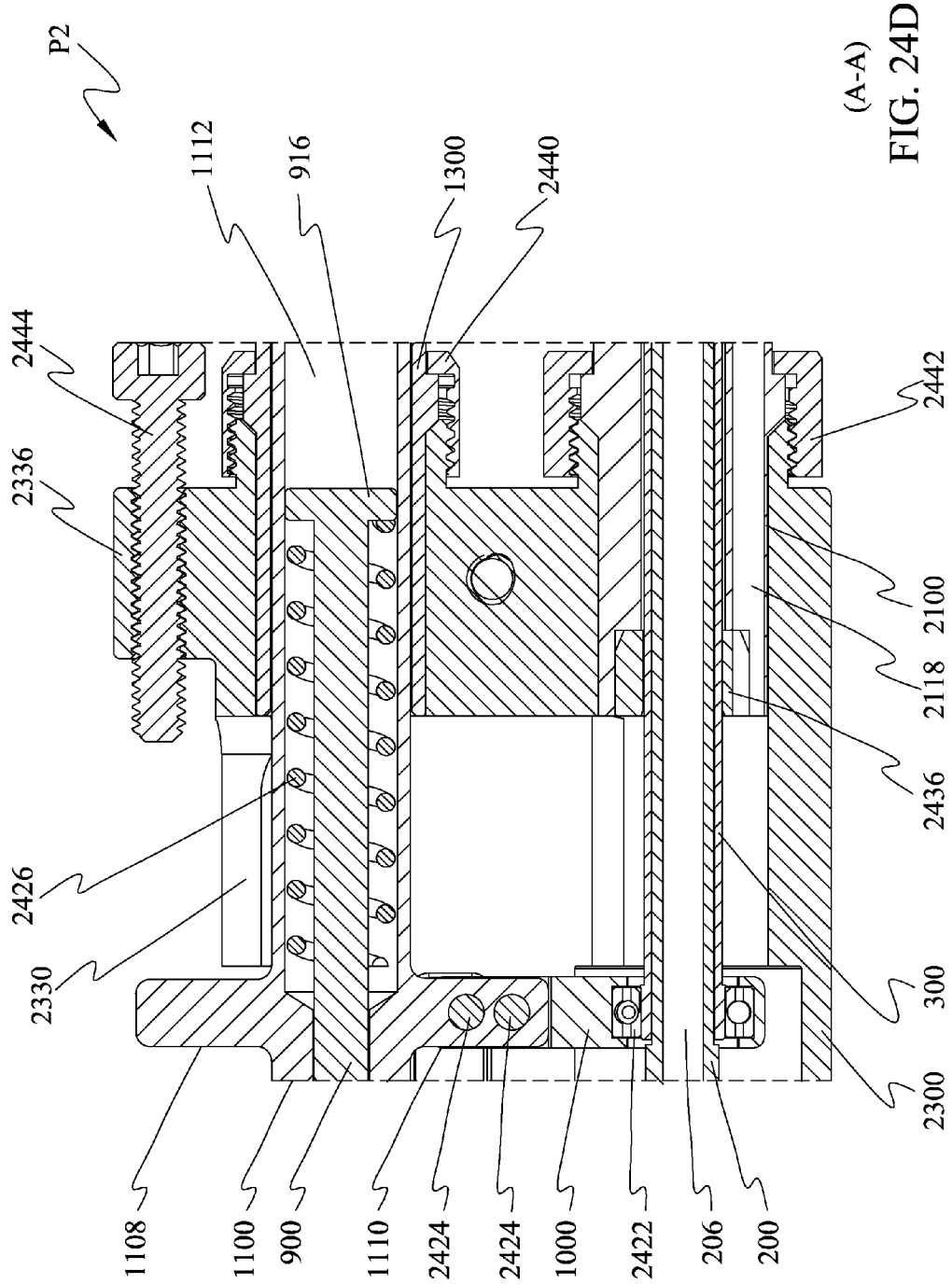
FIG. 24D is a close-up view of a portion "P2" of the sectional view of FIG. 24B.
Figure 24F:
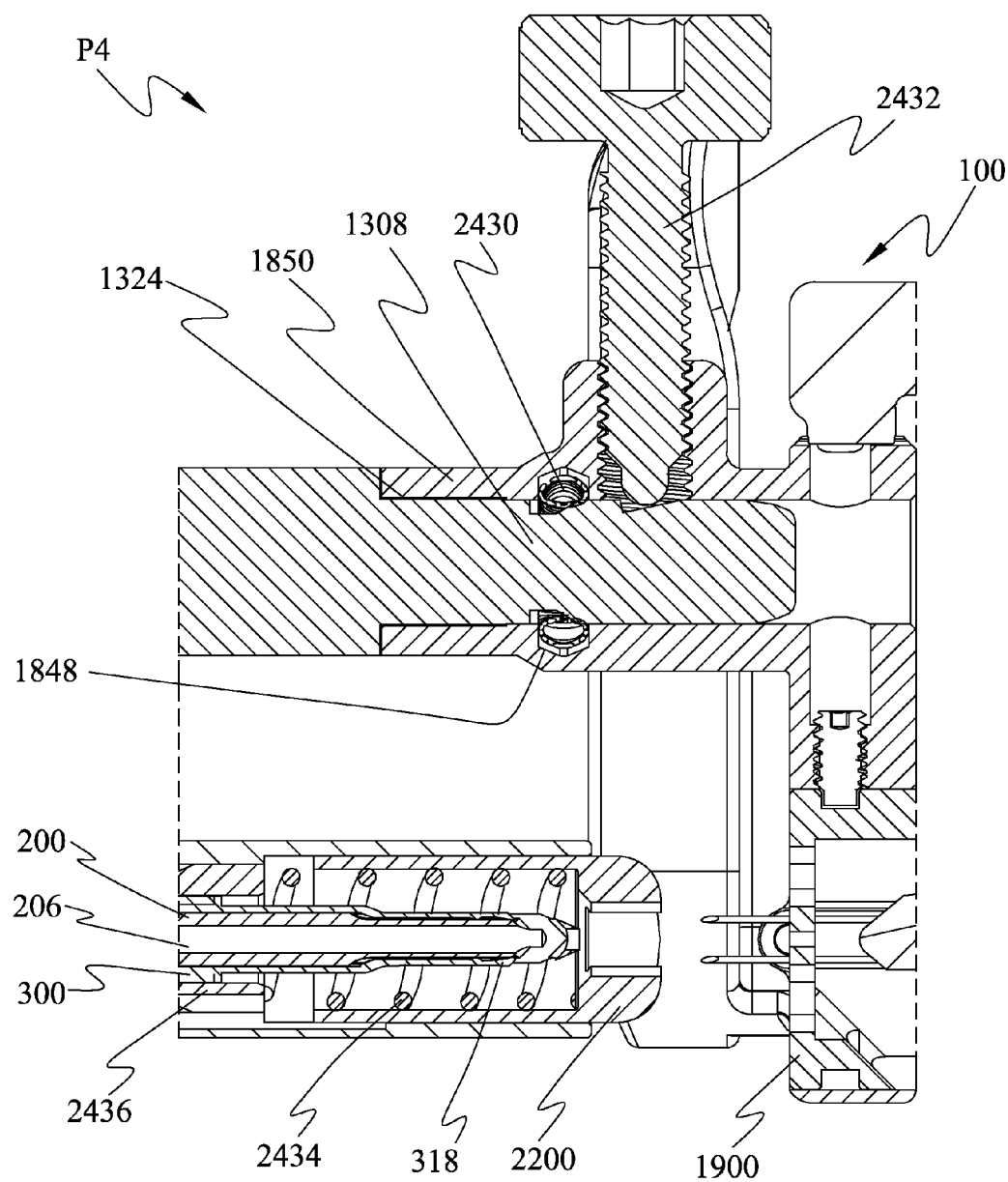
FIG. 24F is a close-up view of a portion "P4" of the sectional view of FIG. 24B.
Figure 24G:
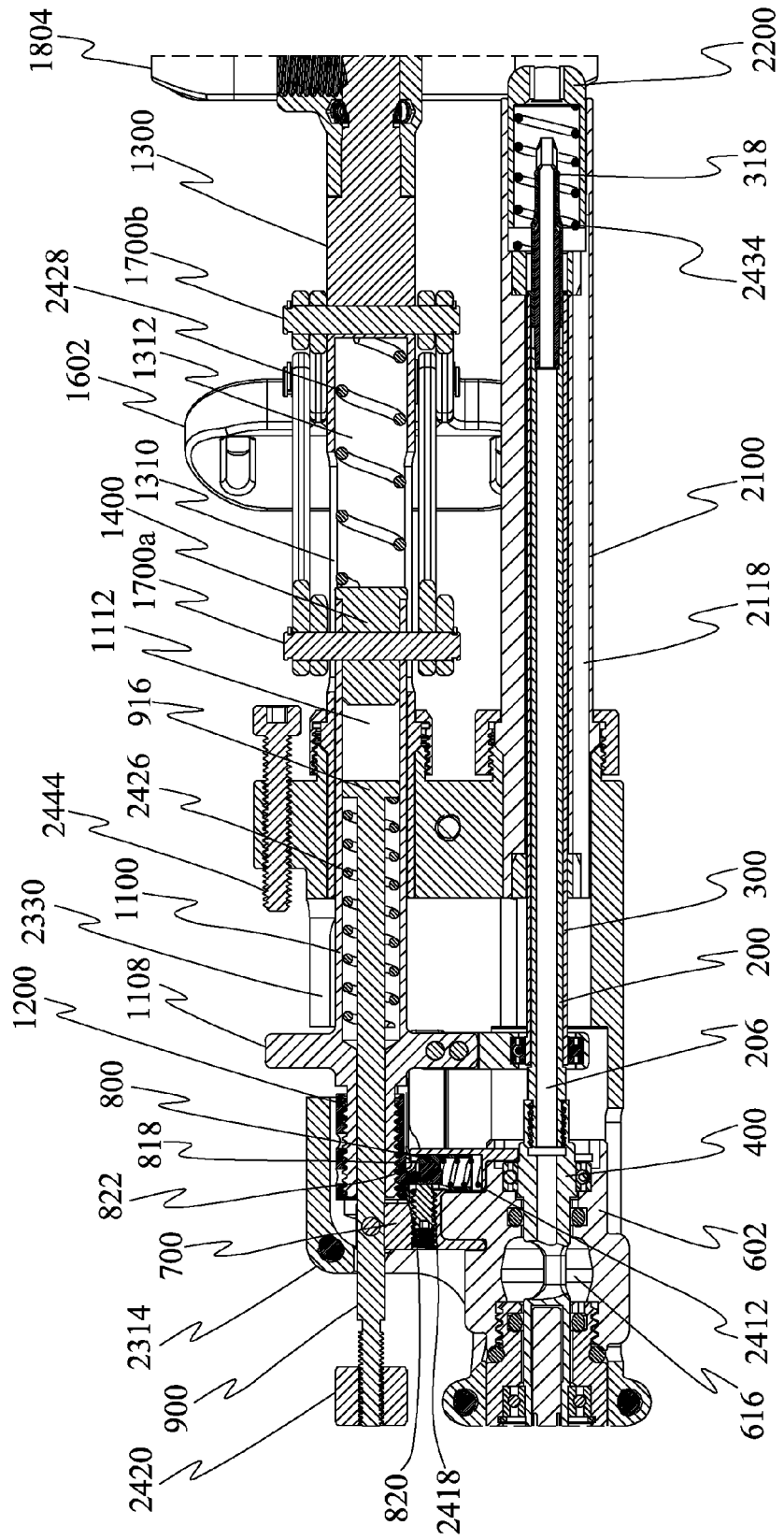
Figure 24H:
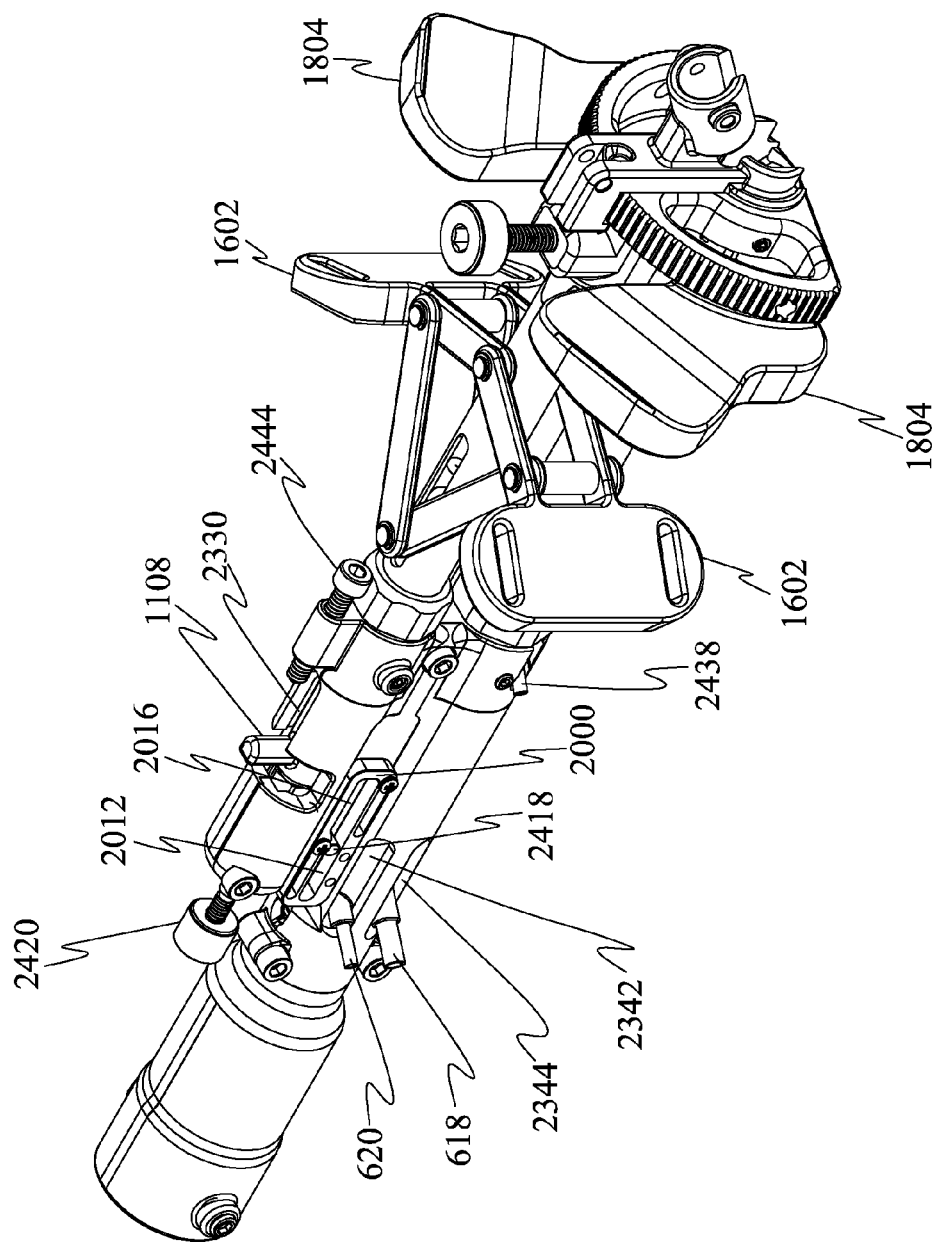
Figure 24L:
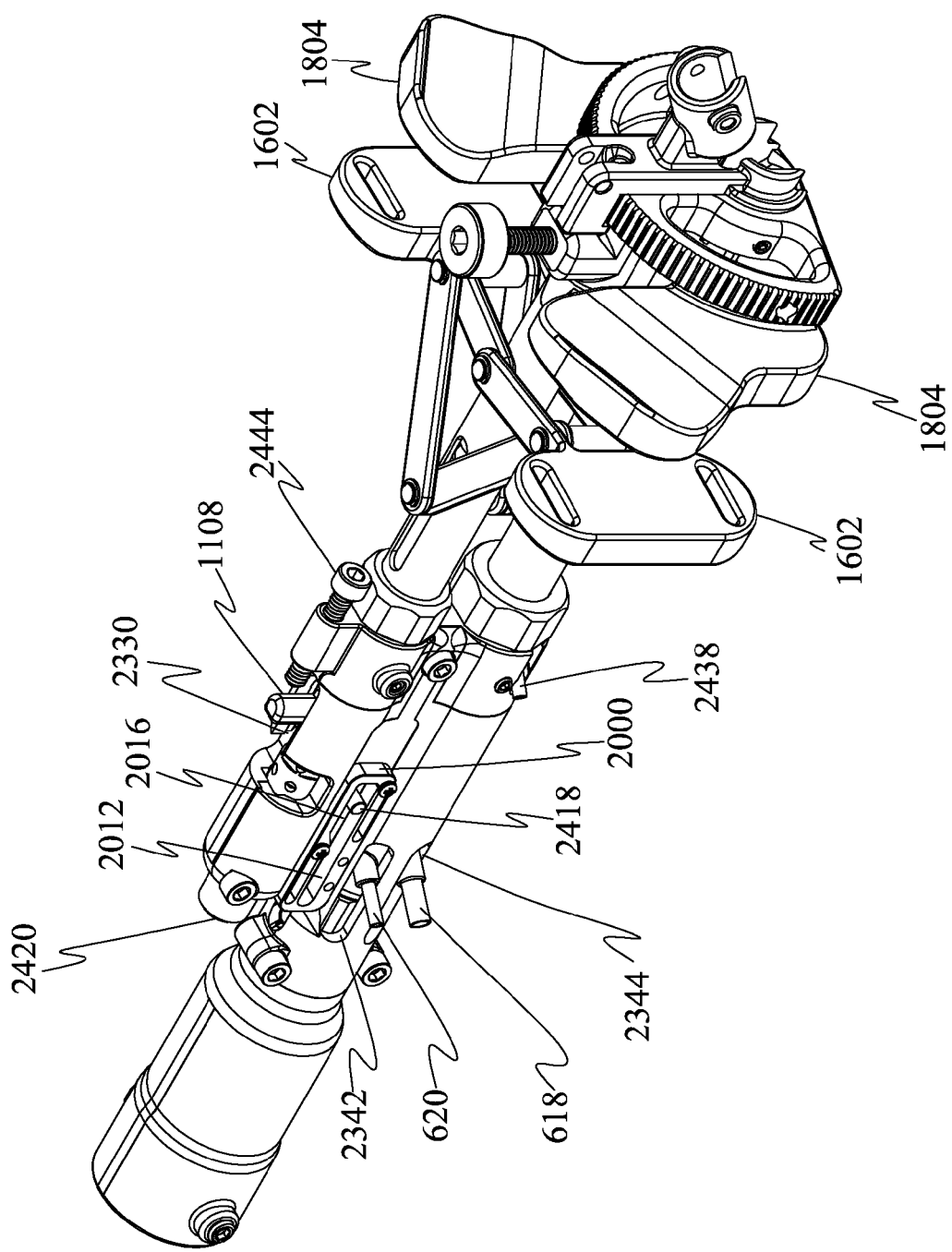

The operator may place his thumbs on the concave curvature 1844 defined in the pair of second paddles 1804. The remaining four fingers in each of his hands may be pressed against the first surface 1606 of the first paddles 1602. The operator may begin to apply pressure over the first surface 1606 of the first paddles 1602, so as to move the first paddles 1602 from its initial position towards the second paddles 1804. Movement of the first paddles 1602 may result in movement of the link member pin 1700a (may be referred to as 1700) engaged with the second arm cap 1400 towards another link member pin 1700b (may also be referred to as 1700), while the second arm cap 1400 compresses the spring 2428. The movement of the link member pin 1700a may result in movement or translation of the second arm 1100 in the first direction along its longitudinal axis towards the link member pin 1700b, which may be stationary. The movement of the second arm 1100 may result in the movement of the spring 2426. The movement of the spring 2426 may be achieved as one end of the spring 2426 may be interfacing with the step 1120 of the second arm 1100. The other end of the spring 2426 may in turn apply force over the first engaging surface 918 of the first arm 900, thereby enabling movement of the first arm 900 in the first direction. The first arm 900 may continue moving in the first direction until the threaded adjustment knob 2420 interfaces the surface of the housing assembly 2300 at the housing assembly's 2300 proximal end 2314 (refer FIGS. 24K-24L).

Movement of the first arm 900 may result in movement of the first connecting member 700 in the first direction, since it may be connected to the first arm 900 by the pin 2416. Movement of the first connecting member 700 may result in movement of the stop 800, which is received in the first connecting member 700. The pin 2418 received by the stop 800 may translate in the first slot 2002 defined in the guide plate 2000.

Movement of the first arm 900 may also result in movement of the carriage 600 and the adapter 400 in the first direction.

The adapter 400 which may be connected to the first member 200 may result in movement of the first member 200 in the first direction.

The second connecting member 1000 may move in the first direction as a result of the movement of the second arm 1100 in the first direction. The bearing 2422 and the second member 300 connected to the second connecting member 1000 also moves in the first direction.

Figure 24M:
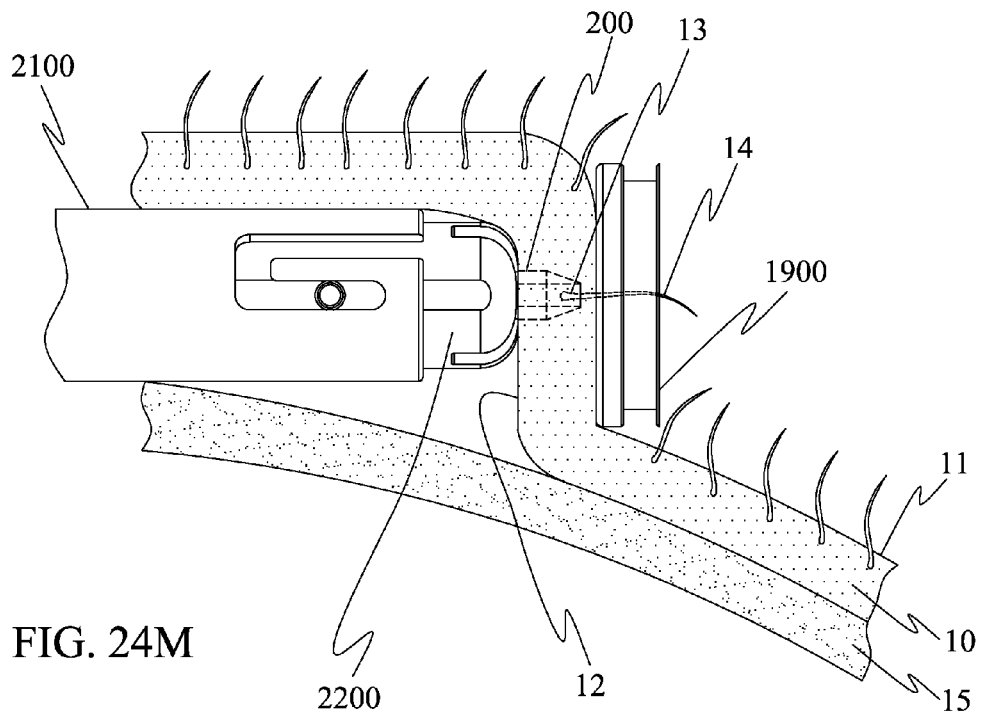
Figure 24N:
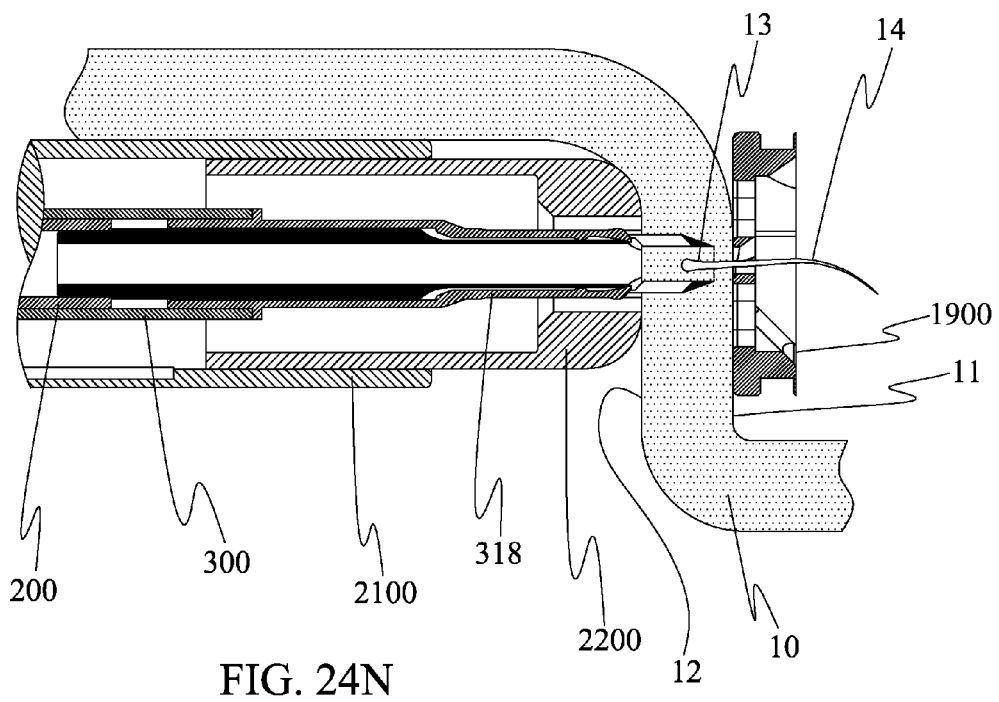

As recited earlier, the first arm 900 may continue moving in the first direction until the threaded adjustment knob 2420 interfaces the surface of the housing assembly 2300 at the housing assembly's 2300 proximal end 2314. Once the translatory movement of the first arm 900 stops, the components, such as, the first connecting member 700, carriage 600, adapter 400 and the first member 200, which may have translated as a result of translatory movement of the first arm 900 may also stop. The position of the paddles 1602, 1804 at which the first member 200 stops translating in the first direction may be referred to as intermediate position. At this position, the first member 200 may have cut through the tissue that may have the target hair follicle, thereby creating a channel or circular circumferential cut or punch in the tissue, such that at least a portion of the target hair follicle is within the channel (refer FIGS. 24M-24N). Further, at this position, pin 2418 may have moved towards the third region 2016 of the first slot 2002 of the guide plate 2000. The second seat 820 of the stop 800 may interface with the cylindrical surface of the adjustment sleeve 1200.

Figure 24P:
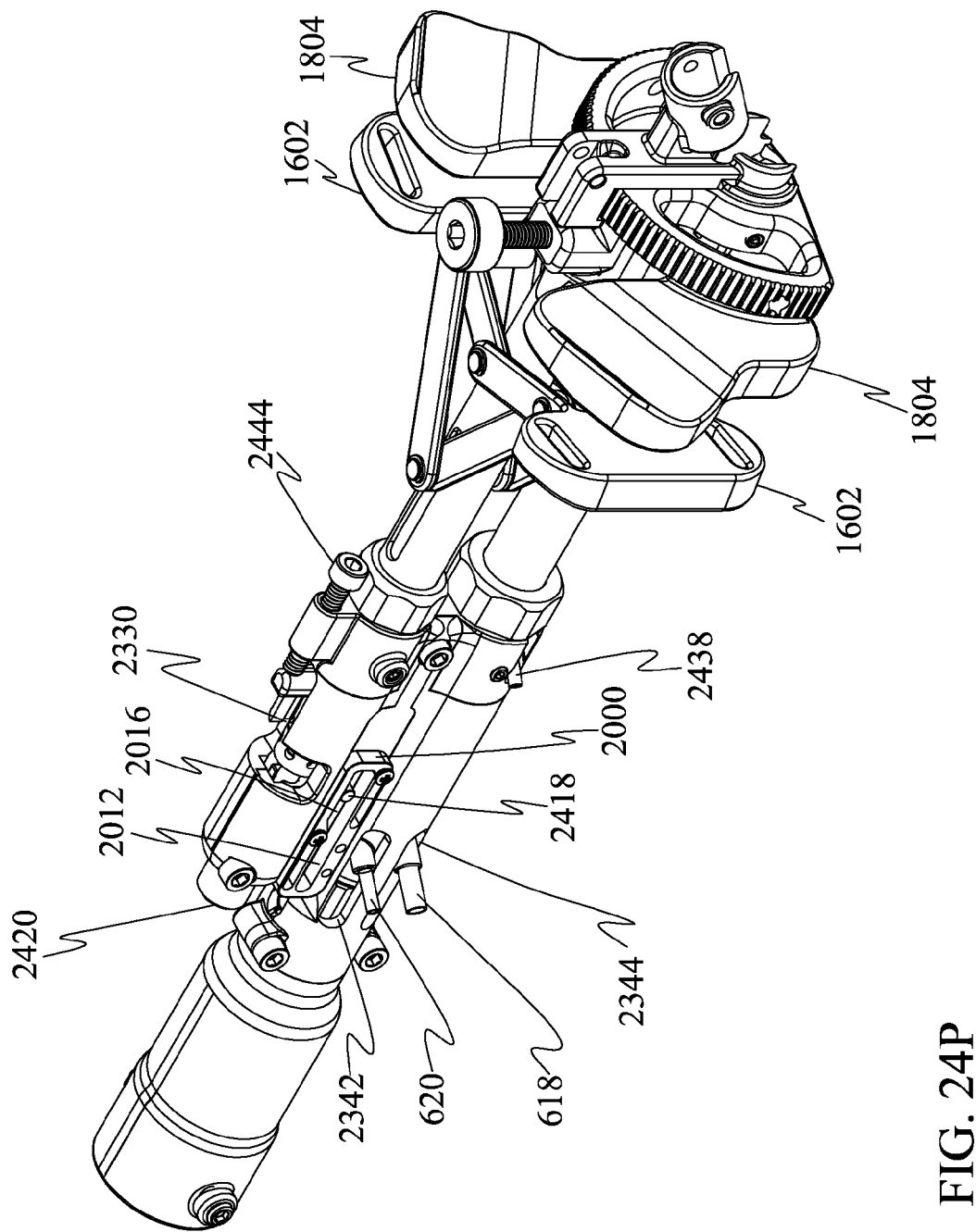
Figure 24Q:
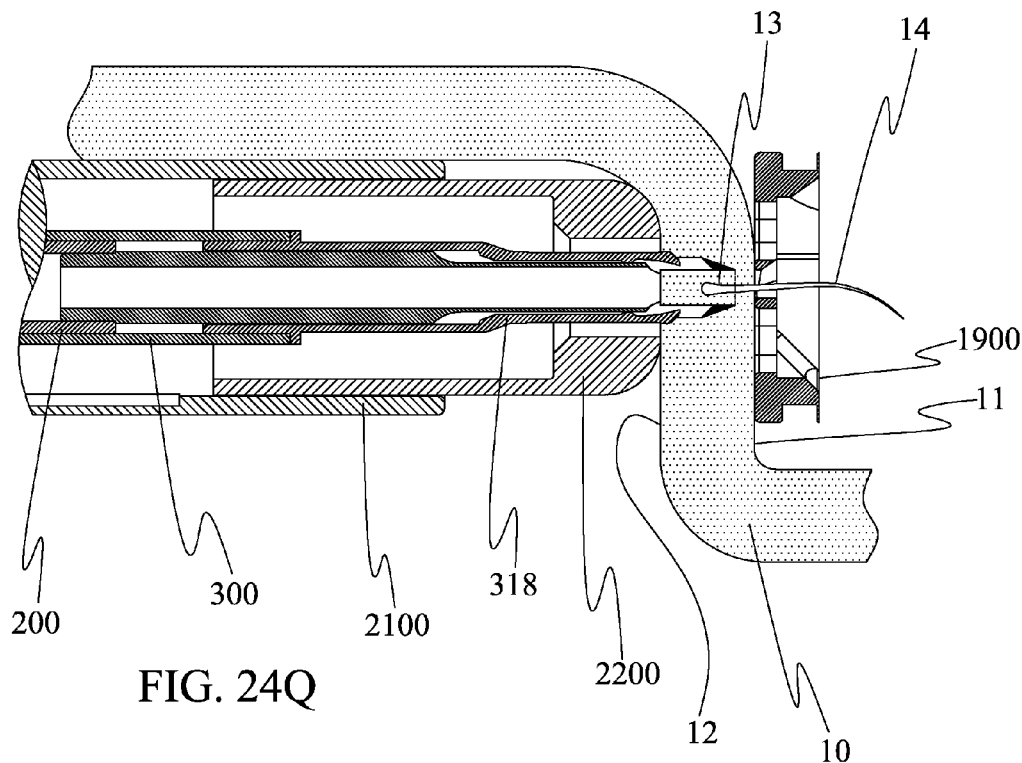
Figure 24R:
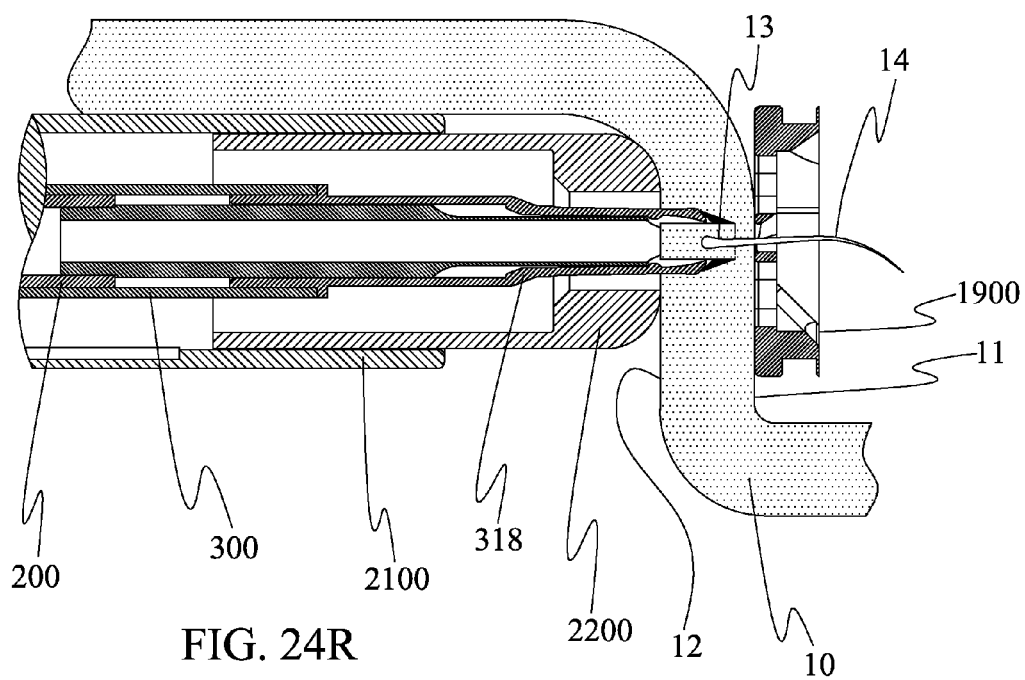
Figure 24S:
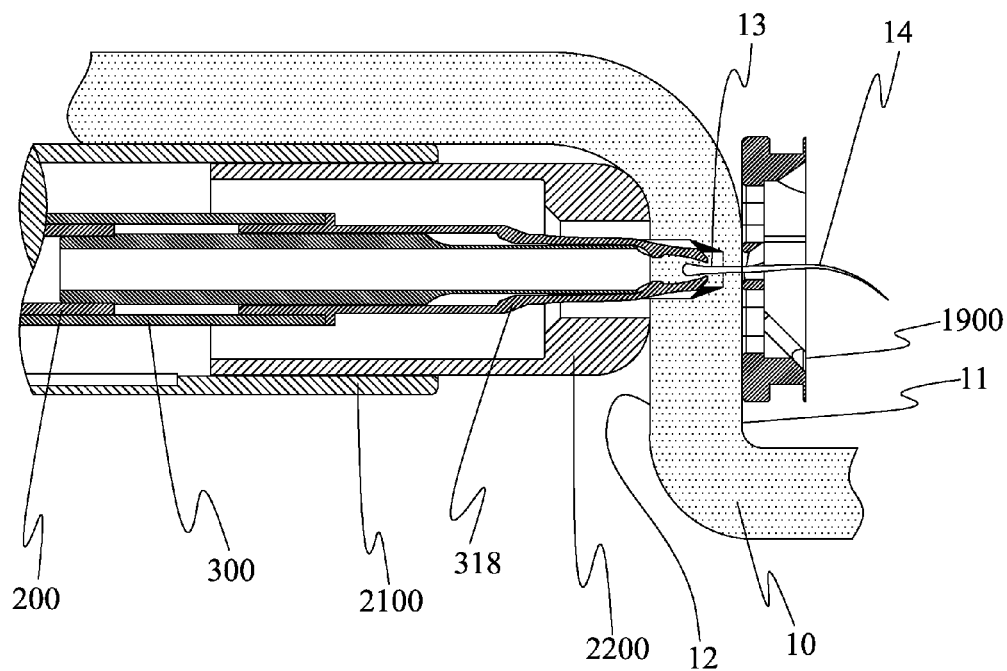
Figure 24T:
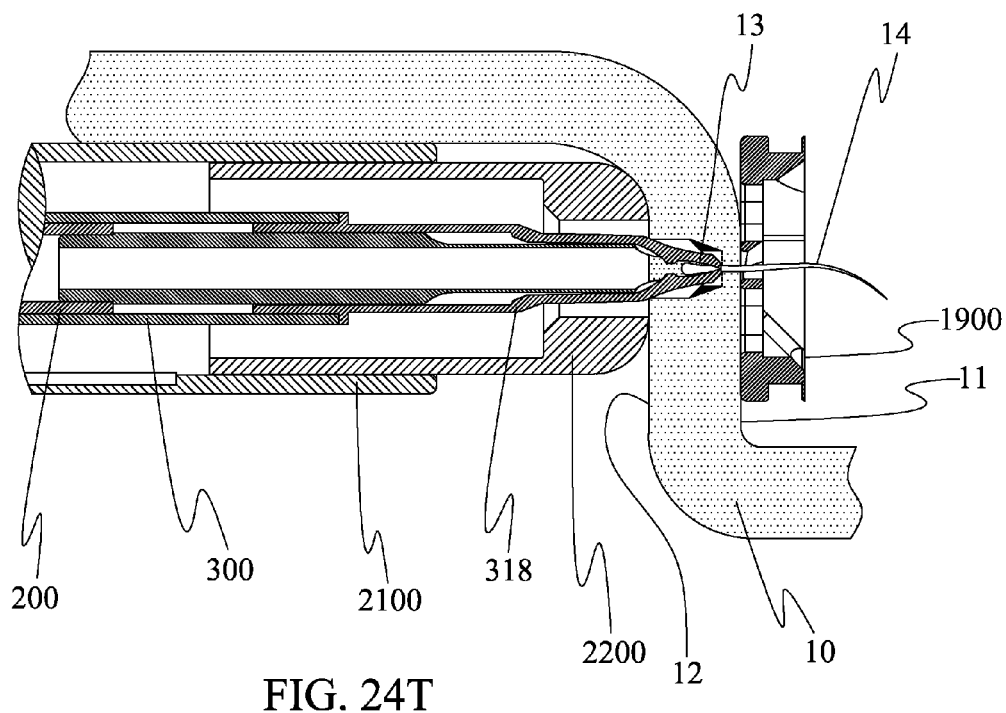

The operator may operate the paddles 1602, 1804 to move beyond the intermediate position to reach a final position. The operator may continue to pull the first paddles 1602 towards second paddles 1804. Movement of the first paddles 1602 may result in further movement of the link member pin 1700 engaged with the second arm cap 1400 towards the other link member pin 1700, while the second arm cap 1400 further compresses the spring 2428. The movement of the link member pin 1700 may result in further movement or translation of the second arm 1100 in the first direction along its longitudinal axis towards the other link member pin 1700. The second connecting member 1000 may further move in the first direction as a result of the movement of the second arm 1100 in the first direction. The bearing 2422 and the second member 300 connected to the second connecting member 1000 also may also move in the first direction. The spring 2426 disposed in the first bore 1112 of the second arm 1100 may be compressed due to the movement of the second arm 1100, while the first arm 900 is restricted from moving further. The movement of the second arm 1100 may result in sliding of the adjustment sleeve 1200 over the second seat 820 of the stop 800 which is being pushed against the adjustment sleeve 1200 by the spring 2412. As the adjustment sleeve 1200 slides past the second seat 820, the spring 2412 expands such that the first seat 818 align or interfaces with the cylindrical surface of the adjustment sleeve 1200 (refer FIG. 24O). The instant position may be referred to as locking member extended position. The pin 2418 may interface with a superior edge 2028 of the first slot 2002 in the third region 2016 of the guide plate 2000. The movement of the second arm 1100 and the second member 300 in the first direction may be stopped by a movement restricting feature, such as the screw 2444 engaged in the protrusion 2336 of the housing assembly 2300 (refer FIGS. 24O-24P). The positions of the paddles 1602 and 1804 at which the movement of the second member 300 in the first direction stops may be referred to as final position.

The translatory movement of the second member 300 while the first member 200 is restricted from moving in the first direction may result in the arms 318 moving into the first bore 206 of the first member 200 through the apertures 222, such that the tips 320 of the arms meet inside the first bore 206, thereby clipping the tissue that may be have the target hair follicle, which may have been cut by the first member (refer FIGS. 24Q-24T).

The operator may stop applying force over the paddles 1602, 1804, so that the paddles 1602, 1804 retract from the final position to the initial position.

Figure 24U:
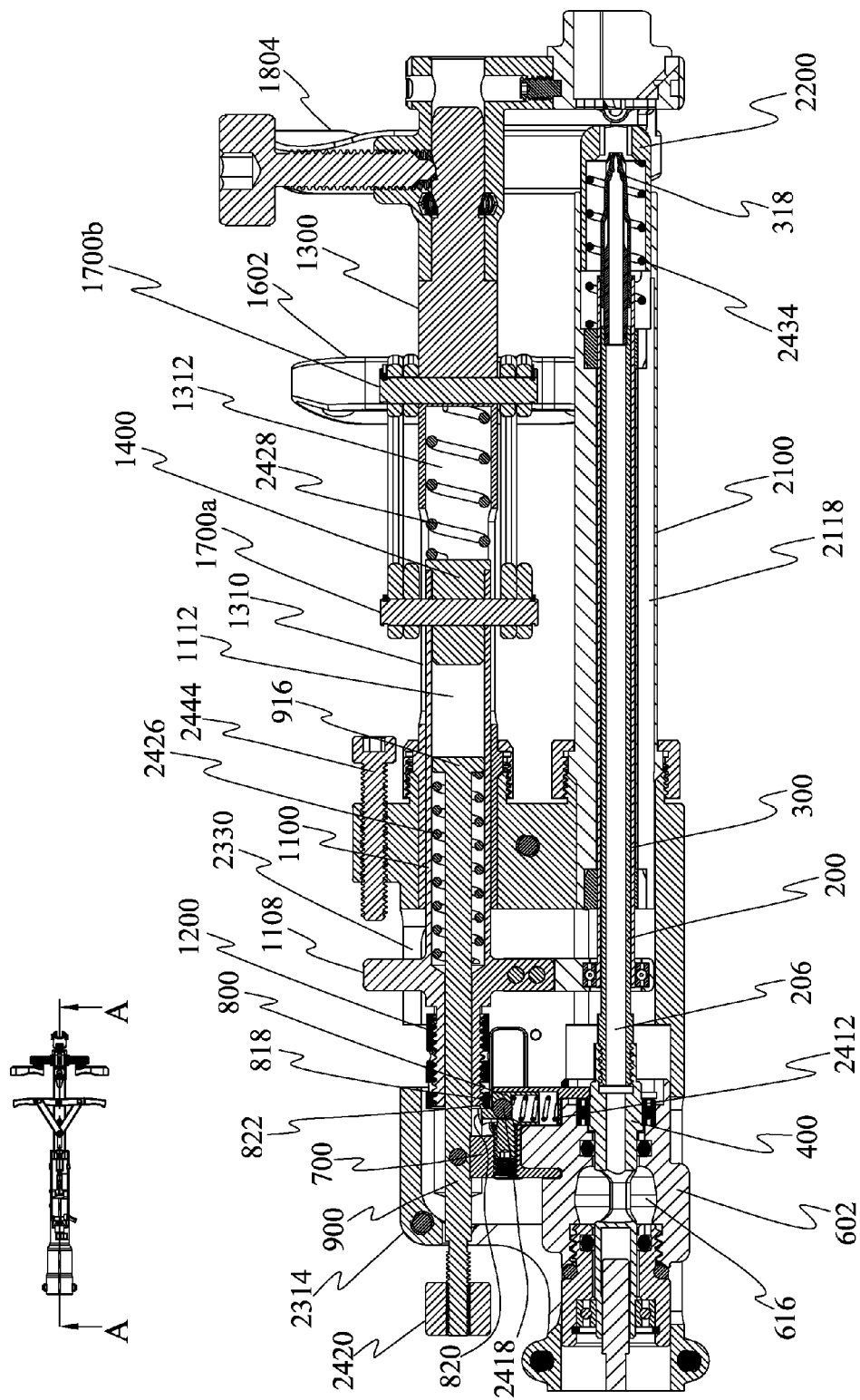
Figure 24V:
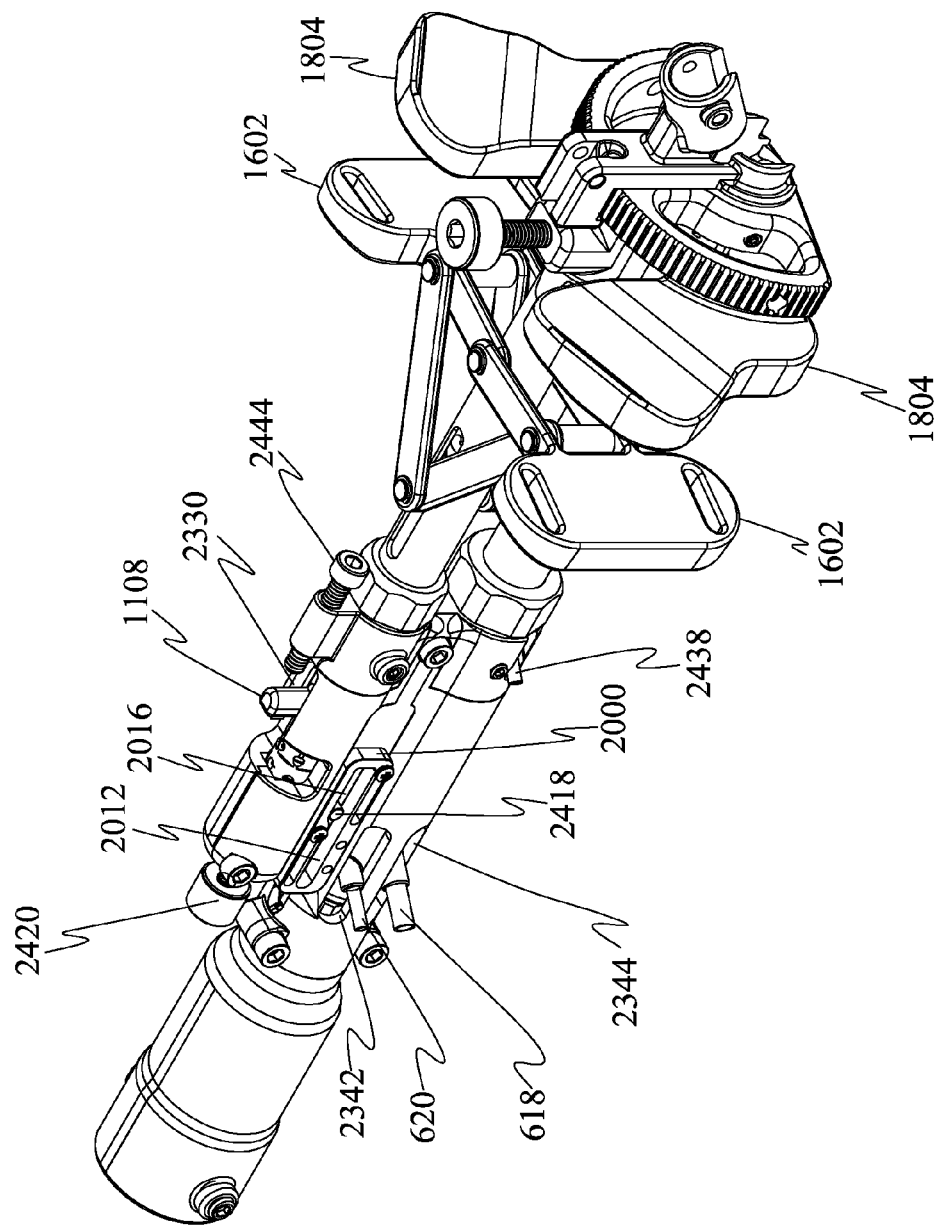
Figure 24W:
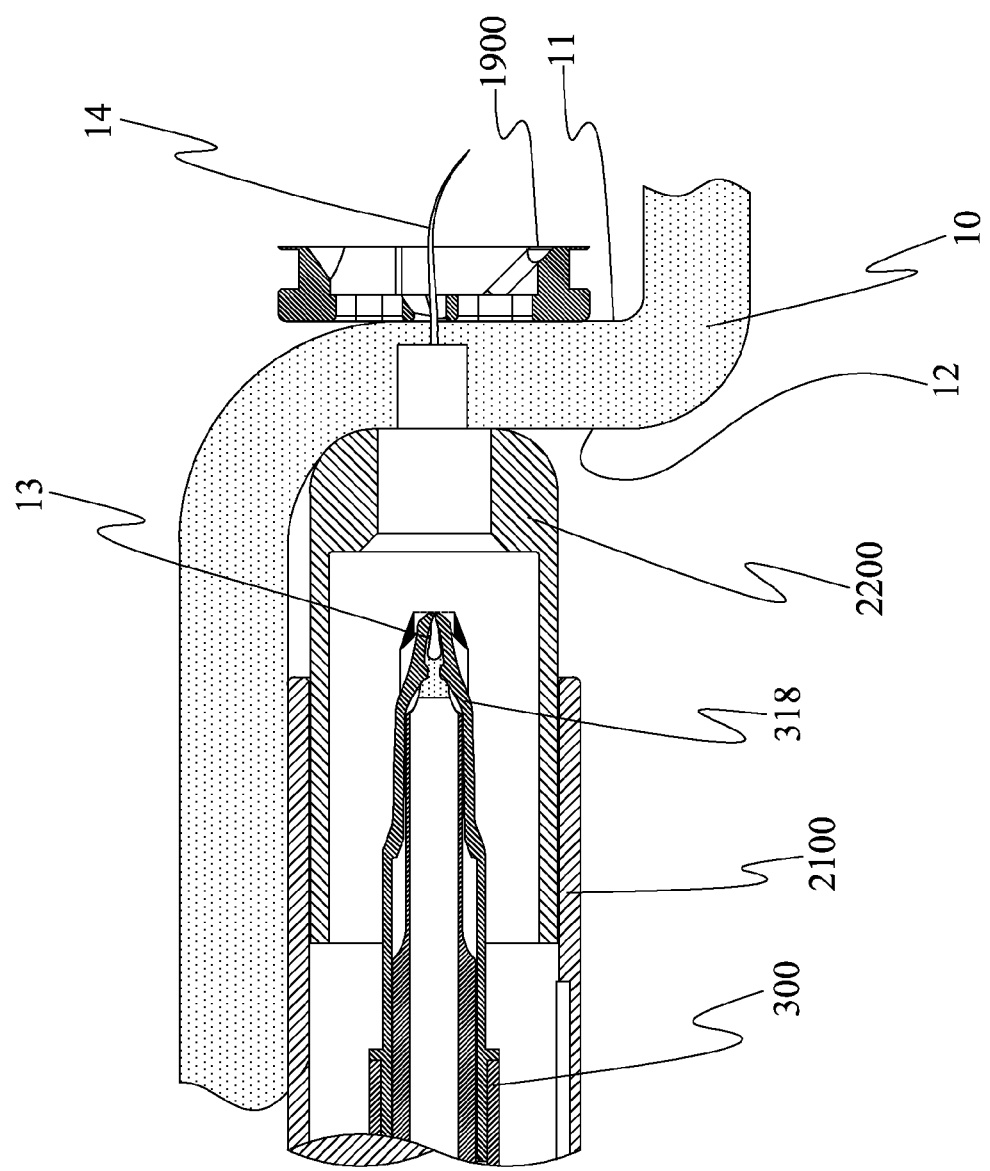

Upon stopping the application of force over the paddles 1602 and 1804, the spring 2428 may expand, and may apply expansion force on the head 1404 of the second arm cap 1400. As a result of spring 2428 applying expansion force on the second arm cap 1400, the second arm cap 1400 may move in a second direction opposite to the first direction. The second arm cap 1400 may in-turn move the second arm 1100 in the second direction. The adjustment sleeve 1200 may in-turn move in the second direction as a result of the second arm 1100 movement in the second direction. The proximal end of the adjustment sleeve 1200 which may be interfacing the block wall 822 of the stop 800, may move in the second direction such that, the stop 800 may cause the pin 2418 to slide in the third region 2016. The movement of the stop 800 may cause the first connecting member 700, the first arm 900 and the first member 200 to translate or move in the second direction. Hence, the first member 200 and the second member 300 may move simultaneously in the second direction (refer FIGS. 24U-24W).

Figure 24Y:
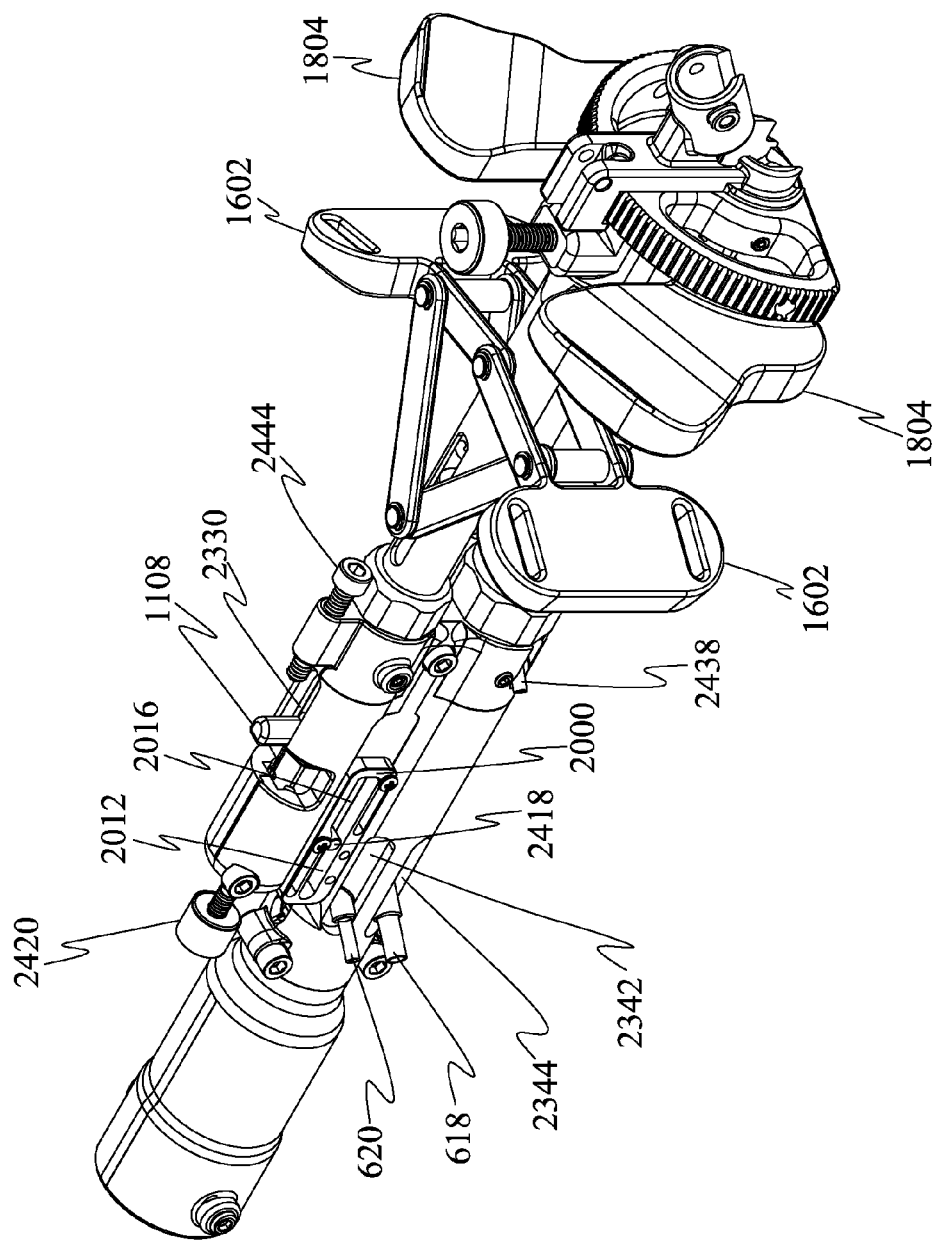

Subsequent movement of the second arm 1100 may cause the pin 2418 to slide into the second region 2014, which has the curved surface 2026 in the guide plate 2000, thereby causing the stop 800 to move downwards or move in an inferior direction. Subsequently, the pin 2118 may slide into the first region 2012, thereby releasing the interface between the proximal end of the adjustment sleeve 1200 and the block wall 822 of the stop 800 (refer FIGS. 24X-24Y). The instant position in which various parts of the system 110 that form the locking assembly are in a position that allows second member 300 to translate in the second direction at least relative to the first member 200 may be referred to as locking member retracted position. The position of the first member 200 at this stage may be referred to as first member intermediate position.

Subsequent movement of the adjustment sleeve 1200 may not result in movement of the first connecting member 700, first arm 900 or the first member 200 in the second direction, as the adjustment sleeve 1200 may not be able to push the first connecting member 700 in the second direction. Hence, the first member 200 may not translate in the second direction, while the second member 300 translates in the second direction. This may cause the arms 318 to retract out of the first bore 206, and the arms 318 or the protrusions 328 of the arms 318 may rest on the slots 220 of the first member 200. The second member 300 may translate in the second direction, while the first arm 200 is stationary, with respect to the translatory movement, until the adjustment sleeve 1200 interfaces with the pair of arms 726 of the first connecting member 700. The position of the second member 300 at this stage may be referred to as second member retracted position (refer FIGS. 24Z-24Z1). Once the interface is established, the first arm 900 and the first member 200 may begins to translate along with the second arm 1100 and the second member 300, until the paddles 1602 and 1804 reaches the initial position.

The components, such as, guide plate 2000, first connecting member 700, stop 800, spring 2412, pin 2418 and adjustment sleeve 1200, which may enable locking so as to enable simultaneous translatory movement of the first member 200 and the second member 300 in the second direction after the movement in the first direction is terminated, may be referred to as locking assembly. The position of the locking assembly when the adjustment sleeve 1200 interfaces with the block wall 822 may be referred to as locking member or locking assembly extended position. The position of the locking assembly when the adjustment sleeve 1200 interfaces with the second seat 820 may be referred to as locking member or locking assembly retracted position.

A depth limiting means or the knob 2420 may be adjusted to either be position closer to the proximal end 2314 of the housing assembly 2300 to control the extent to which the first member 200 translates in the first direction. Controlling the extent to which the first member 200 translates in the first direction may in turn enable controlling the depth of cut made by the first member 200 into the tissue. Hence, the distance between the distal end of the channel cut into the tissue and the external surface of the skin may be controlled. The operator may make such adjustment based on the desired depth of cut or thickness of the skin.

A motion limiting means or the screw 2444 received by the protrusion 2336 of the housing assembly 2300 may be adjusted to configure the extent to which the second member 300 or second means may be translated in the first direction.

The rotation of the first member 200 may be terminated, operably or automatically, after the first member 200 has terminated its movement in the first direction.

Alternatively, the rotation of the first member 200 and the second member 300 may be terminated, operably or automatically, before initiating the translatory movement of the first member 200 and the second member 300 in the second direction.

Alternatively, the rotation of the first member 200 may be terminated, operably or automatically, after the first member 200 has terminated its movement in the first direction. The rotation of the first member 200 and the second member 300 may be initiated after the second member 300 has terminated its movement in the first direction.

Alternatively, the first member 200 and the second member 300 may be rotated throughout the process of extracting the tissue from underneath the skin.

Alternatively, the first member 200 and the second member 300 may not be rotated, and the first member 200 and second member 300 may only be translated to enable cutting and clipping, or to enable extracting of the target tissue.

The flush port 620 may be generally closed. The flush port 620 may be opened to receive fluid into the chamber 616. Generally, while extracting the hair follicle, fluid may be passed into the inlet port 2438, while suction may be applied at the outlet port 618. The fluid received through the inlet port 2438 may pass through the channel 2118 provided in the cover member 2100, and through the channel provided in the bushing 2436 to enter the first bore 206 provided in the first member 200. The fluid may enter the first bore 206 through one or more openings 222 or opening of the first bore 206 at the distal end 210. The fluid may enter the first bore 206 due to suction applied at the outlet port 618. The fluid may carry the hair follicle that may be disposed in the first bore 206 after it has been cored and clipped, towards the exit port. The hair follicle along with fluid may travel through the first bore 206 and enter the adapter 400. The hair follicle along with fluid may exit the adapter 400 and enter the chamber 616 through apertures 418. Eventually the hair follicle along with fluid may exit the system 110 through the outlet port 618.

The invention claimed is:

1. A system configured to extract a tissue from underneath an external surface of a skin, the system comprising:
   a first system configured to extract the tissue, the first system extending along a first longitudinal axis, the first system including:
      a first member defining a first bore extending along a longitudinal axis, wherein,
         at least a portion of the first member is configured to approach the tissue from beneath the external surface of the skin;
         the first member is configured to translate at least in a first direction along the longitudinal axis of the first member through the tissue and to rotate about the longitudinal axis of the first member so as to cut at least a portion of the tissue; and
   a second system configured to alter an alignment of the tissue, the second system being coupled to the first system and extending along a second longitudinal axis parallel to and spaced apart in a superior direction from the first longitudinal axis of the first system, the second system including:
      a counter pressure device configured to extend from the second longitudinal axis towards the longitudinal axis of the first member so as to interface with at least the external surface of the skin when the tissue is disposed between the first member and the counter pressure device.

2. The system of claim 1, wherein the first system further comprises a second member defining a second bore configured to receive at least a portion of the first member, and wherein the second member is configured to translate at least in the first direction along the longitudinal axis of the first member and to clip at least a portion of the tissue that is cut by the first member.

3. The system of claim 2, wherein the first member includes a coring cannula configured to receive the tissue within the bore of the first member and the second member includes a clipping cannula configured to clip the tissue that is received within the first bore.

4. The system of claim 3, wherein the clipping cannula of the second member further comprises at least one arm provided at a distal end of the second member;
the first member further comprises at least one aperture extending from an external surface of the first member into the first bore of the first member; and,
wherein the arm of the clipping cannula is configured to translate into the aperture and towards the longitudinal axis of the first member as the second member translates in the first direction along the longitudinal axis of the first member.

5. The system of claim 2, wherein the first member and the second member are configured such that relative translatory motion between the first member and the second member is restricted at least after the second member has traversed a maximum distance in the first direction until the second member has traversed a preconfigured distance in a second direction opposite to the first direction.

6. The system of claim 2, further comprising a first arm, a second arm, a first connecting member, a second connecting member and at least one paddle, wherein,
the first connecting member connects the first arm with the first member;
the second connecting member connects the second arm with the second member; and
the paddle is engaged with at least one of the first arm and the second arm; and,
wherein the first member and the second member are configured such that as the paddle moves from an initial position to an intermediate position, which thereby results in a translatory motion of the first arm, the first member, the first connecting member, the second arm, the second member and the second connecting member in the first direction towards the tissue, whereupon the paddle reaches the intermediate position the first member is restricted from moving further in the first direction; and whereupon as the paddle moves past the intermediate position towards a final position results in a further translatory motion of the second arm, the second member and the second connecting member in the first direction.

7. The system of claim 6, wherein the first member and the second member are further configured such that as the paddle moves from the final position to the initial position results in a simultaneous translatory motion of the first member and the second member in a second direction opposite to the first direction until the first member reaches a first member intermediate position, whereupon the second member continues to translate in the second direction to assume a second member retracted position while the first member is retained in the first member intermediate position; and upon the second member reaching the second member retracted position the first member and the second member translate in the second direction.

8. The system of claim 7, further comprising a locking assembly wherein, the locking assembly is configured to assume a locking member retracted position and a locking member extended position, wherein,
the locking assembly is configured to allow relative translatory motion between the first member and the second member in the second direction when the locking assembly is in the locking member retracted position; and
the locking assembly is configured to restrict relative translatory motion between the first member and the second member in the second direction when the locking assembly is in the locking member extended position.

9. The system of claim 1, wherein the first system further comprises a tissue stabilizing member configured to be moved below the external surface of the skin, to translate parallel to the longitudinal axis of the first member, and to apply pressure at least around the tissue when the tissue is disposed between the tissue stabilizing member and the counter pressure device.

10. The system of claim 1, wherein the first system further comprises a power shaft and an adapter, wherein one of the power shaft and the adapter comprises a first portion having a polygonal cross section, and the other of the power shaft and the adapter defines a bore, wherein at least a part of the bore defines a corresponding polygonal cross section, wherein the first portion is configured to translate in the bore, wherein the power shaft is configured to rotate, and wherein the adapter is engaged with the first member.

11. A system configured to extract a tissue that includes at least one hair follicle from underneath an external surface of a skin, the system comprising:
a first system configured to extract the at least one hair follicle, the first system extending along a first longitudinal axis, the first system including:
a first means for making a channel, the channel comprising a proximal end and a distal end, such that at least a part of the tissue comprising the at least one hair follicle is within the channel, and the proximal end and the distal end are configured to approach the tissue from underneath an external surface of the skin;
a second means for clipping at least a part of the tissue within the channel
a second system coupled to the first system, the second system extending along a second longitudinal axis parallel to and spaced apart in a superior direction from the first longitudinal axis of the first system, the second system including: a depth limiting means for configuring a distance between the distal end of the channel and the external surface of the skin.

12. The system of claim 11, further comprising a first compressible means adapted with the first means and the second means, the first compressible means for enabling the second means to translate with respect to the first means in at least a first direction towards the external surface of the skin.

13. The system of claim 11, further comprising at least one paddle and a second compressible means, wherein the second compressible means is adapted with the paddle, the first means, and the second means for enabling an application of a force on the paddle to move the paddle from an initial position to a final position, wherein a distal end of the first means and a distal end of the second means are closest to the external surface of the skin, and for releasing of the force applied on the paddle, which results in the paddle retracting from the final position to the initial position.

14. The system of claim 11, further comprising a motion limiting means for enabling operably setting of a maximum distance the second means translates in a first direction towards the external surface of the skin.

\* \* \* \* \*